(12) United States Patent
Roth et al.

(10) Patent No.: US 12,234,461 B2
(45) Date of Patent: Feb. 25, 2025

(54) TARGETED NON-VIRAL DNA INSERTIONS

(71) Applicant: The Regents of the University of California, Oakland, CA (US)

(72) Inventors: Theodore Lee Roth, San Francisco, CA (US); Alexander Marson, San Francisco, CA (US)

(73) Assignee: THE REGENTS OF THE UNIVERSITY OF CALIFORNIA, A CALIFORNIA CORPORATION

(*) Notice: Subject to any disclaimer, the term of this patent is extended or adjusted under 35 U.S.C. 154(b) by 0 days.

(21) Appl. No.: 18/463,589

(22) Filed: Sep. 8, 2023

(65) Prior Publication Data

US 2024/0117360 A1 Apr. 11, 2024

Related U.S. Application Data

(60) Division of application No. 17/498,531, filed on Oct. 11, 2021, now Pat. No. 11,814,624, which is a continuation of application No. 16/622,843, filed as application No. PCT/US2018/037919 on Jun. 15, 2018, now abandoned.

(60) Provisional application No. 62/552,180, filed on Aug. 30, 2017, provisional application No. 62/520,117, filed on Jun. 15, 2017.

(51) Int. Cl.
- *C12N 15/113* (2010.01)
- *C12N 9/22* (2006.01)
- *C12N 15/10* (2006.01)
- *C12N 15/90* (2006.01)

(52) U.S. Cl.
CPC ............ *C12N 15/1138* (2013.01); *C12N 9/22* (2013.01); *C12N 15/102* (2013.01); *C12N 15/90* (2013.01); *C12N 2310/20* (2017.05); *C12N 2320/53* (2013.01)

(58) Field of Classification Search
None
See application file for complete search history.

(56) References Cited

U.S. PATENT DOCUMENTS

| | | |
|---|---|---|
| 6,824,978 B1 | 11/2004 | Cox, III et al. |
| 8,133,733 B2 | 3/2012 | Khan |
| 8,586,363 B2 | 11/2013 | Voytas et al. |
| 8,795,965 B2 | 8/2014 | Zhang |
| 9,221,886 B2 | 12/2015 | Liu et al. |
| 9,512,446 B1 | 12/2016 | Joung et al. |
| 9,526,784 B2 | 12/2016 | Liu et al. |
| 9,758,775 B2 | 9/2017 | Voytas et al. |
| 9,855,297 B2 | 1/2018 | Duchateau et al. |
| 9,890,393 B2 | 2/2018 | Duchateau et al. |
| 11,033,584 B2 | 6/2021 | Roth et al. |
| 11,083,753 B1 | 8/2021 | Roth et al. |
| 11,331,346 B2 | 5/2022 | Roth et al. |
| 11,814,624 B2 | 11/2023 | Roth et al. |
| 2002/0064802 A1 | 5/2002 | Raschke et al. |
| 2002/0160940 A1 | 10/2002 | Case et al. |
| 2003/0087817 A1 | 5/2003 | Cox, III et al. |
| 2003/0232410 A1 | 12/2003 | Liljedahl et al. |
| 2005/0136040 A1 | 6/2005 | Hart et al. |
| 2006/0182736 A1 | 8/2006 | Kim et al. |
| 2007/0254291 A1 | 11/2007 | Cui et al. |
| 2009/0082250 A1 | 3/2009 | Hart et al. |
| 2010/0093617 A1 | 4/2010 | Barrangou et al. |
| 2011/0145940 A1 | 6/2011 | Voytas et al. |
| 2011/0265198 A1 | 10/2011 | Gregory et al. |
| 2012/0077270 A1 | 3/2012 | Hart et al. |
| 2012/0110685 A1 | 5/2012 | Bonas et al. |
| 2013/0236504 A1 | 9/2013 | Alexis et al. |
| 2014/0068797 A1 | 3/2014 | Doudna et al. |
| 2014/0189896 A1 | 7/2014 | Zhang et al. |
| 2014/0199767 A1 | 7/2014 | Barrangou et al. |
| 2014/0294773 A1 | 10/2014 | Brouns et al. |
| 2014/0301990 A1 | 10/2014 | Gregory et al. |
| 2014/0349402 A1 | 11/2014 | Cooper et al. |
| 2014/0357530 A1 | 12/2014 | Zhang et al. |
| 2015/0016954 A1 | 1/2015 | Thibodeau et al. |
| 2015/0071903 A1 | 3/2015 | Liu et al. |
| 2015/0110762 A1 | 4/2015 | Holmes et al. |
| 2015/0140664 A1 | 5/2015 | Byrne et al. |
| 2015/0164954 A1 | 6/2015 | Bonini et al. |
| 2015/0259704 A1 | 9/2015 | Church et al. |
| 2015/0283265 A1 | 10/2015 | Peyman |
| 2015/0322457 A1 | 11/2015 | Kim et al. |
| 2015/0344912 A1 | 12/2015 | Kim et al. |

(Continued)

FOREIGN PATENT DOCUMENTS

| | | |
|---|---|---|
| CA | 2951707 A1 | 12/2015 |
| EP | 3 250 693 B1 | 5/2021 |

(Continued)

OTHER PUBLICATIONS

Schumann et al. 2015. Generation of knock-in primary human T cells using Cas9 ribonucleoproteins. PNAS. vol. 12, No. 33, 10437-10442 (Year: 2015).*

Amaxa Human CD34+ Cell Nucleofactor Kit Booklet, Lonza, Filed with Notice of Opposition for EP Patent No. 3250693, Mar. 3, 2022, 4 pages.

Amaxa Human T Cell Nucleofactor Kit Booklet, Lonza, Filed with Notice of Opposition for EP Patent No. 3250693, Mar. 3, 2022, 5 pages.

(Continued)

*Primary Examiner* — Celine X Qian
*Assistant Examiner* — Tiffany Nicole Grooms
(74) *Attorney, Agent, or Firm* — MARSHALL, GERSTEIN & BORUN LLP

(57) ABSTRACT

Provided herein are methods and compositions for editing the genome of a cell. In some embodiments, a nucleotide sequence of at least 200 nucleotides in length is inserted into a target region in the genome of a cell.

20 Claims, 54 Drawing Sheets

Specification includes a Sequence Listing.

(56) References Cited

U.S. PATENT DOCUMENTS

| | | |
|---|---|---|
| 2016/0017366 A1 | 1/2016 | Chen et al. |
| 2016/0024524 A1 | 1/2016 | Joung et al. |
| 2016/0053274 A1 | 2/2016 | D'Halluin |
| 2016/0102322 A1 | 4/2016 | Ravinder et al. |
| 2016/0160210 A1 | 6/2016 | Mali et al. |
| 2016/0200779 A1 | 7/2016 | Liu et al. |
| 2016/0264999 A1 | 9/2016 | Rao et al. |
| 2016/0298134 A1 | 10/2016 | Chen et al. |
| 2016/0298135 A1 | 10/2016 | Chen et al. |
| 2016/0298138 A1 | 10/2016 | Chen et al. |
| 2016/0304893 A1 | 10/2016 | Daboussi et al. |
| 2016/0354487 A1 | 12/2016 | Zhang et al. |
| 2017/0000743 A1 | 1/2017 | Ghoroghchian et al. |
| 2017/0016027 A1 | 1/2017 | Lee et al. |
| 2017/0044569 A9 | 2/2017 | Church et al. |
| 2017/0073705 A1 | 3/2017 | Chen et al. |
| 2017/0175128 A1 | 6/2017 | Welstead et al. |
| 2017/0191082 A1 | 7/2017 | Chen et al. |
| 2017/0211075 A1 | 7/2017 | Lee et al. |
| 2017/0290858 A1 | 10/2017 | Zhao et al. |
| 2017/0296676 A1 | 10/2017 | Stephan et al. |
| 2017/0335331 A1 | 11/2017 | Zhao et al. |
| 2018/0044700 A1 | 2/2018 | Doudna et al. |
| 2018/0161447 A1 | 6/2018 | Watson et al. |
| 2018/0312848 A1 | 11/2018 | Zhao et al. |
| 2019/0136263 A1* | 5/2019 | Kornete .................. A61P 35/00 |
| 2020/0048606 A1 | 2/2020 | Marson et al. |

FOREIGN PATENT DOCUMENTS

| | | | |
|---|---|---|---|
| KR | 10-2014-0101203 | | 8/2014 |
| KR | 20180023840 A | | 3/2018 |
| WO | 0041566 A1 | | 7/2000 |
| WO | 0183751 A2 | | 11/2001 |
| WO | 0183751 A3 | | 8/2002 |
| WO | 03033701 A1 | | 4/2003 |
| WO | 03080809 A2 | | 10/2003 |
| WO | 2004092194 A2 | | 10/2004 |
| WO | 2004108883 A2 | | 12/2004 |
| WO | 2005123962 A2 | | 12/2005 |
| WO | 2007025097 A2 | | 3/2007 |
| WO | 2008021207 A2 | | 2/2008 |
| WO | 2011059836 A2 | | 5/2011 |
| WO | 2011072246 A2 | | 6/2011 |
| WO | 2011139336 A1 | | 11/2011 |
| WO | 2013134349 A1 | | 9/2013 |
| WO | 2013176772 A1 | | 11/2013 |
| WO | 2014089290 A1 | | 6/2014 |
| WO | 2014093661 A2 | | 6/2014 |
| WO | 2014144761 A2 | | 9/2014 |
| WO | 2014153470 A2 | | 9/2014 |
| WO | 2014161821 A1 | | 10/2014 |
| WO | 2015035136 A2 | | 3/2015 |
| WO | 2015048690 A1 | | 4/2015 |
| WO | 2015057980 A1 | | 4/2015 |
| WO | 2015073867 A1 | | 5/2015 |
| WO | 2015086795 A1 | | 6/2015 |
| WO | 2015089419 A2 | | 6/2015 |
| WO | 2015089462 A1 | | 6/2015 |
| WO | 2015089486 A2 | | 6/2015 |
| WO | 2015115903 A1 | | 8/2015 |
| WO | 2015117021 A1 | | 8/2015 |
| WO | 2015089419 A9 | | 11/2015 |
| WO | 2016021972 A1 | | 2/2016 |
| WO | 2016036754 A1 | | 3/2016 |
| WO | 2016049251 A1 | | 3/2016 |
| WO | 2016057951 A2 | | 4/2016 |
| WO | 2016097751 A1 | | 6/2016 |
| WO | 2016118697 A1 | | 7/2016 |
| WO | 2016123578 | | 8/2016 |
| WO | 2016123578 A1 | | 8/2016 |
| WO | 2016118697 A9 | | 9/2016 |
| WO | 2016135559 A2 | | 9/2016 |
| WO | 2016172359 A2 | | 10/2016 |
| WO | 2016196388 A1 | | 12/2016 |
| WO | 2016205680 A1 | | 12/2016 |
| WO | 2016205703 A1 | | 12/2016 |
| WO | 2017004509 A1 | | 1/2017 |
| WO | 2017011519 A1 | | 1/2017 |
| WO | 2017035659 A1 | | 3/2017 |
| WO | 2017053729 A1 | | 3/2017 |
| WO | 2017058751 A1 | | 4/2017 |
| WO | 2017062451 A1 | | 4/2017 |
| WO | 2017070056 A1 | | 4/2017 |
| WO | 2017070169 A1 | | 4/2017 |
| WO | 2017070429 A1 | | 4/2017 |
| WO | 2017079673 A1 | | 5/2017 |
| WO | 2017091630 A1 | | 6/2017 |
| WO | WO-2017093969 A1 * | 6/2017 | ......... A61K 31/7088 |
| WO | 2017115128 A2 | | 7/2017 |
| WO | 2017156484 A1 | | 9/2017 |
| WO | 2017177137 A1 | | 10/2017 |
| WO | 2017180989 A2 | | 10/2017 |
| WO | 2017181110 A1 | | 10/2017 |
| WO | 2017186550 A1 | | 11/2017 |
| WO | 2017189336 A1 | | 11/2017 |
| WO | 2017210334 A1 | | 12/2017 |
| WO | 2017220527 A1 | | 12/2017 |
| WO | 2018035387 A1 | | 2/2018 |
| WO | 2018039084 A1 | | 3/2018 |
| WO | 2018068135 A1 | | 4/2018 |
| WO | 2018073391 A1 | | 4/2018 |
| WO | 2018073393 A2 | | 4/2018 |
| WO | 2018094291 A1 | | 5/2018 |
| WO | 2019089610 A1 | | 5/2019 |

OTHER PUBLICATIONS

Code of Federal Regulations Patents, Trademarks and Copyrights, Excerpts from Appendix R—Patent Rules of the USPTO's Manual of Patent Examining Procedures (MPEP) and MPEP 605.01 filed with Notice of Opposition for EP Patent No. 3250693, Mar. 3, 2022, 9 pages.

Declaration by Dr. Theodore Roth, Filed with Notice of Opposition for EP Patent No. 3250693, Mar. 3, 2022, 3 pages.

U.S. Appl. No. 62/110,187, Filed with Notice of Opposition for EP Patent No. 3250693, Cover Sheet, Mar. 3, 2022, 2 pages.

Carbonnel et al., Extensive Small Intestinal T-cell Lymphoma of Low-Grade Malignancy Associated with a New Chromosomal Translocation, Cancer, vol. 73, No. 4, Feb. 15, 1994, pp. 1286-1291.

Chira et al., Progresses Towards Safe and Efficient Gene Therapy Vectors, Oncotarget, vol. 6, No. 31, Oct. 13, 2015, pp. 30675-30703.

European Application No. 16744244.1, Notice of Opposition mailed on Mar. 3, 2022, 22 pages.

EP 16744244.1—Response to Communication Pursuant to Rules 70(2) and 70a(2) EPC, Feb. 20, 2019, 6 pages.

European Application No. 3250693, Response to Notice of Opposition, Annex 2 (Assignment document for U.S. Appl. No. 62/110,187) mailed on Aug. 2, 2022, 10 pages.

European Application No. 3250693, Response to Notice of Opposition, Auxiliary Requests 1-55 (Clean version) mailed on Aug. 2, 2022, 110 pages.

European Application No. 3250693, Response to Notice of Opposition, Auxiliary Requests 1-55 (Marked-up version) mailed on Aug. 2, 2022, 165 pages.

European Application No. 3250693, Response to Notice of Opposition, Main Request (Clean version) mailed on Aug. 2, 2022, 2 pages.

European Application No. 3250693, Response to Notice of Opposition mailed on Aug. 2, 2022, 20 pages.

European Application No. 3250693, Response to Notice of Opposition, Main Request (Marked up version) mailed on Aug. 2, 2022, 3 pages.

European Application No. 3250693, Response to Notice of Opposition, Annex 1 (Assignment document for U.S. Appl. No. 62/209,711) mailed on Aug. 2, 2022, 7 pages.

European Application No. 3250693, Written Submission in Opposition, Further Written Submission in Opposition by Grunecker Patent-Und Rechtsanwalte mailed on Mar. 15, 2023, 351 pages.

(56) References Cited

OTHER PUBLICATIONS

European Application No. 3250693, Written Submission in Opposition, Further Written Submission in Opposition by Grunecker Patent-Und Rechtsanwalte mailed on Dec. 9, 2022, 9 pages.
Gwiazda et al., High Efficiency CRISPR/Cas9-mediated Gene Editing in Primary Human T-cells Using Mutant Adenoviral E4orf6/E1b55k "Helper" Proteins, Molecular Therapy, vol. 24, No. 9, Sep. 2016, pp. 1570-1580.
Karenko et al., Primary Cutaneous T-Cell Lymphomas Show a Deletion or Translocation Affecting NAV3, the Human UNC-53 Homologue, Cancer Research, vol. 65, No. 18, Sep. 15, 2005, pp. 8101-8110.
International Application No. PCT/US2016/015836, PCT Request mailed on Jan. 29, 2016, 5 pages.
Rosenberg et al., Adoptive Cell Transfer as Personalized Immunotherapy for Human Cancer, Science, vol. 348, No. 6230, Apr. 3, 2015, pp. 62-68.
Schumann et al., Generation of Knock-In Primary Human T Cells Using Cas9 Ribonucleoproteins, Proceedings of the National Academy of Sciences, vol. 112, No. 33, Aug. 18, 2015, pp. 10437-10442.
Baldanzi et al., "SAP-Mediated Inhibition of Diacylglycerol Kinase .alpha. Regulates TCR-Induced Diacylglycerol Signaling," The Journal of Immunology, vol. 187, No. 11, Dec. 1, 2011, pp. 5941-5951.
Chira et al., "Progresses Towards Safe and Efficient Gene Therapy Vectors," Oncotarget, vol. 6, No. 31, 2015, pp. 30675-30703.
Cornu et al., "Refining Strategies to Translate Genome Editing to the Clinic," Nat. Med. 23, 2017, pp. 415-423.
EA202090046, Office Action, Sep. 23, 2021, 2 pages.
EP18817563.2, Extended European Search Report, Feb. 12, 2021, 8 pages.
Foley et al., "HCV T Cell Receptor Chain Modifications to Enhance Expression, Pairing, and Antigen Recognition in T Cells for Adoptive Transfer," Molecular Therapy Oncolytics, vol. 5, Jun. 16, 2017, pp. 105-115.
Glusman et al., "Comparative Genomics of the Human and Mouse T Cell Receptor Loci," Immunity, vol. 15, No. 3, Sep. 2001, pp. 337-349.
He et al., "Non-Viral and Viral Delivery Systems for CRISPR-Cas9 Technology in the Biomedical Field," Science China Life Sciences, vol. 60, No. 5, May 2017, pp. 458-467.
Hornung et al., "Intracellular DNA Recognition," Nat. Rev. Immunol. 10, 2010, pp. 123-130.
Kaneko et al., "Simple Knockout by Electroporation of Engineered Endonucleases into Intact Rat Embryos," Scientific Reports vol. 4, No. 6382, Oct. 1, 2014.
Lee et al., "Nanoparticle Delivery of Cas9 Ribonucleoprotein and Donor DNA in Vivo Induces Homology-Directed DNA Repair," Nat. Biomed. Eng., vol. 1, Oct. 2, 2017, pp. 889-901.
Li et al., "Optimization of Genome Engineering Approaches with the CRISPR/Cas9 System," Plos One, vol. 9, Issue 8, Aug. 28, 2014, pp. 1-10.
Liang et al., "Enhanced CRISPR/Cas9-Mediated Precise Genome Editing by Improved Design and Delivery of gRNA, Cas9 Nuclease, and Donor DNA," Journal of Biotechnology, vol. 241, Jan. 10, 2017, pp. 136-146.
Okamoto et al., "A Promising Vector for TCR Gene Therapy: Differential Effect of siRNA, 2A Peptide, and Disulfide Bond on the Introduced TCR Expression," Molecular Therapy—Nucleic Acids, vol. 1, No. 12, Dec. 18, 2012.
PCT/US2018/037919, International Preliminary Report on Patentability, Dec. 26, 2019, 6 pages.
PCT/US2018/037919, International Search Report and Written Opinion, Sep. 18, 2018, 9 pages.
Rosenberg, "Adoptive Cell Transfer as Personalized Immunotherapy for Human Cancer," Science vol. 80, No. 348, 2015, pp. 62-68, Apr. 3, 2015.
Roth et al., "Reprogramming Human T Cell Function and Specificity with Non-Viral Genome Targeting," Nature, vol. 559, No. 7714, Jul. 19, 2018, 41 pages.
Roybal et al. "Synthetic Immunology: Hacking Immune Cells to Expand Their Therapeutic Capabilities," Annu. Rev. Immunol. 35, 229-253, Apr. 26, 2017.
Sadelain et al., "Therapeutic T Cell Engineering," Nature 545, May 25, 2017, pp. 423-431.
Verhoeven et al., "Lentiviral Vector Gene Transfer into Human T Cells," Methods Mol. Biol. vol. 506, 2009, pp. 97-114.
Zhao et al., "High-Efficiency Transfection of Primary Human and Mouse T Lymphocytes Using RNA Electroporation," Mol. Ther., vol. 13, No. 1, Jan. 2006, pp. 151-159.
Eyquem et al., "Targeting a CAR to the TRAC Locus with CRISPR/Cas9 Enhances Tumour Rejection," Nature, vol. 543, No. 7643, 2017, pp. 113-117.
EP Patent No. 3250693, Notice of Opposition, Mar. 3, 2022, 22 pages.
Cover Sheet, U.S. Appl. No. 62/110,187, filed with Notice of Opposition for EP Patent No. 3250693 on Mar. 3, 2022.
Excerpts from Appendix R—Patent Rules of the USPTO's Manual of Patent Examining Procedures (MPEP) and MPEP 605.01 filed with Notice of Opposition for EP Patent No. 3250693 on Mar. 3, 2022, 9 pages.
PCT Request for International Application No. PCT/US2016/015836, Jan. 29, 2016, 5 pages.
English translation of passages in Korean Application No. 10-2014-0101203 filed with Notice of Opposition for EP Patent No. 3250693 on Mar. 3, 2022.
Mandal et al. "Efficient Ablation of Genes in Human Hematopoietic Stem and Effector Cells using CRISPR/Cas9," Cell Stem Cells 15: 643-652, Nov. 6, 2014, 11 pages.
Kim et al., "Highly efficient RNA-guided genome editing in human cells via delivery of purified Cas9 ribonucleoproteins," Genome Research 24: 1012-1019, Nov. 6, 2014, 16 pages.
ATCC BJ Fibroblast production information file with Notice of Opposition for EP Patent No. 3250693 on Mar. 3, 2022, 1 page.
Declaration by Dr. Theodore Roth, filed with Notice of Opposition for EP Patent No. 3250693 on Mar. 3, 2022, 3 pages.
Lonza Amaxa Nucleofactor Technology Booklet, filed with Notice of Opposition for EP Patent No. 3250693 on Mar. 3, 2022, 12 pages.
Lonza Human T Cell Nucleofactor Kit Booklet, filed with Notice of Opposition for EP Patent No. 3250693 on Mar. 3, 2022, 5 pages.
Lonza Human CD34+ Cell Nucleofactor Kit Booklet, filed with Notice of Opposition for EP Patent No. 3250693 on Mar. 3, 2022, 4 pages.
Qasim and Thrasher, "Progress and prospects for engineered T cell therapies," British Journal of Haematology 166: 818-829, Jun. 17, 2014.
U.S. Appl. No. 16/622,843, Final Office Action, mailed Jul. 15, 2022, 7 pages.
U.S. Appl. No. 16/622,843, Non-Final Office Action, mailed Jun. 3, 2022, 12 pages.
Application No. CN201880053088.X, Office Action mailed Sep. 21, 2022, 12 pages.
Application No. JP2019-569305, Office Action mailed Jul. 5, 2022.
Application No. IL271389, Office Action mailed Dec. 19, 2022, 4 pages.
Response to Notice of Opposition for EP Patent No. 3250693, Aug. 2, 2022, 20 pages.
Annex 1 (Assignment document for U.S. Appl. No. 62/209,711)) filed with Response to Notice of Opposition for EP Patent No. 3250693 Aug. 2, 2022, 7 pages.
Annex 2 (Assignment document for U.S. Appl. No. 62/110,187) filed with Response to Notice of Opposition for EP Patent No. 3250693 Aug. 2, 2022, 10 pages.
Hurez et al., "Gene delivery into Primary T cells," *Immunologic Research* 26/1-3: 131-141 (2002).
Fountain et al. "Transfection of primary human skin fibroblasts by electroporation." *Gene* 68:167-172 (1988).
Lambert et al. "Electroporation-mediated uptake of proteins into mammalian cells,"*Biochem. Cell. Biol.* 68: 729-734 (1990).
Main Request (Clean version) filed with Response to Notice of Opposition for EP Patent No. 3250693, Aug. 2, 2022, 2 pages.
Main Request (Marked up version) filed with Response to Notice of Opposition for EP Patent No. 3250693, Aug. 2, 2022, 3 pages.

(56) References Cited

OTHER PUBLICATIONS

Auxiliary Requests 1-55 (Clean version) filed with Response to Notice of Opposition for EP Patent No. 3250693, Aug. 2, 2022, 110 pages.
Auxiliary Requests 1-55 (Marked-up version) filed with Response to Notice of Opposition for EP Patent No. 3250693, Aug. 2, 2022, 165 pages.
Further Written Submission in Opposition of European Patent No. 3 250 693 by Grunecker Patent-Und Rechtsanwalte, submitted on Dec. 9, 2022, 9 pages.
Further Written Submission in Opposition of European Patent No. 3 250 693 by Grunecker Patent-Und Rechtsanwalte, submitted on Mar. 15, 2023, 351 pages.
Monjezi et al., Enhanced Car T-Cell Engineering Using Non-Viral Sleeping Beauty Transposition from Minicircle Vectors, Leukemia, vol. 31, No. 1, Jan. 2017, pp. 186-194.
Eurasian Application No. 202090046, Office Action mailed on Apr. 3, 2024, 6 pages.
Kolata et al., "Swift Gene-Editing Method May Revolutionize Treatments for Cancer and Infectious Diseases," The New York Times, Jul. 11, 2018, p. 13.
Kalos et al., "T cells with chimeric antigen receptors have potent antitumor effects and can establish memory in patients with advanced leukemia," Sci. Transl. Med., 3(95), Aug. 10, 2011, 21 pages.
Science Daily, Jul. 11, 2018, www.sciencedaily.com/releases/2018/07/180711131204.htm.

\* cited by examiner

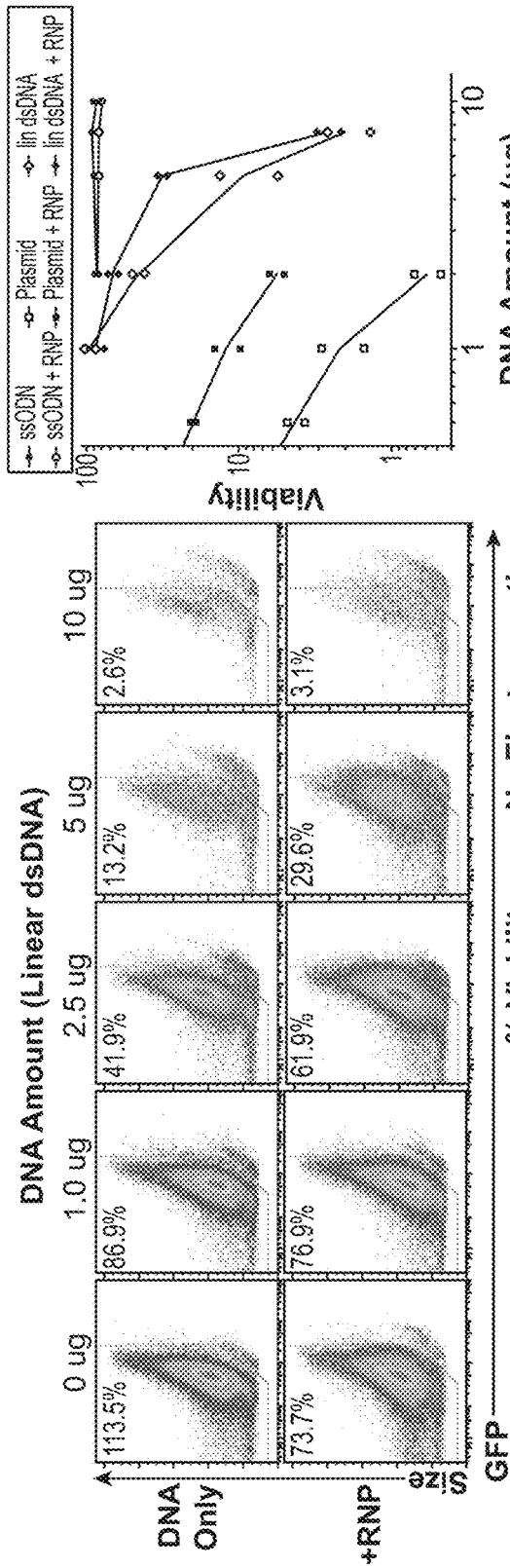
FIG. 10A
FIG. 10B
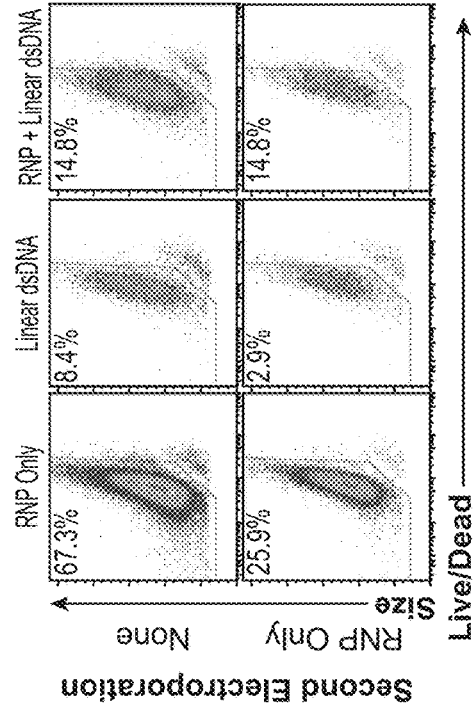
FIG. 10C
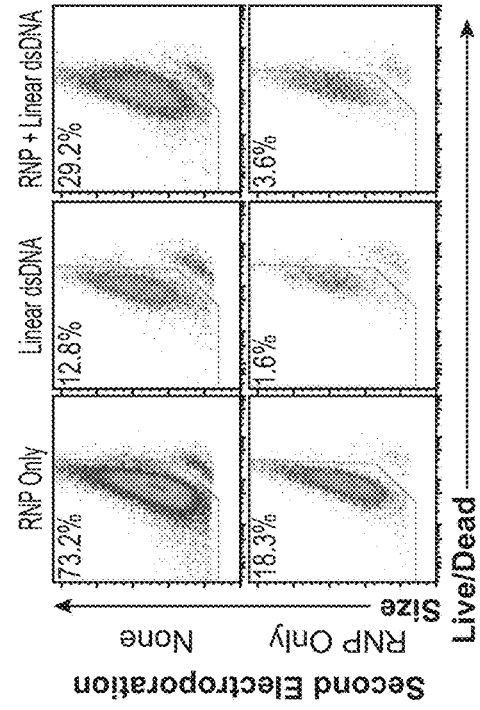

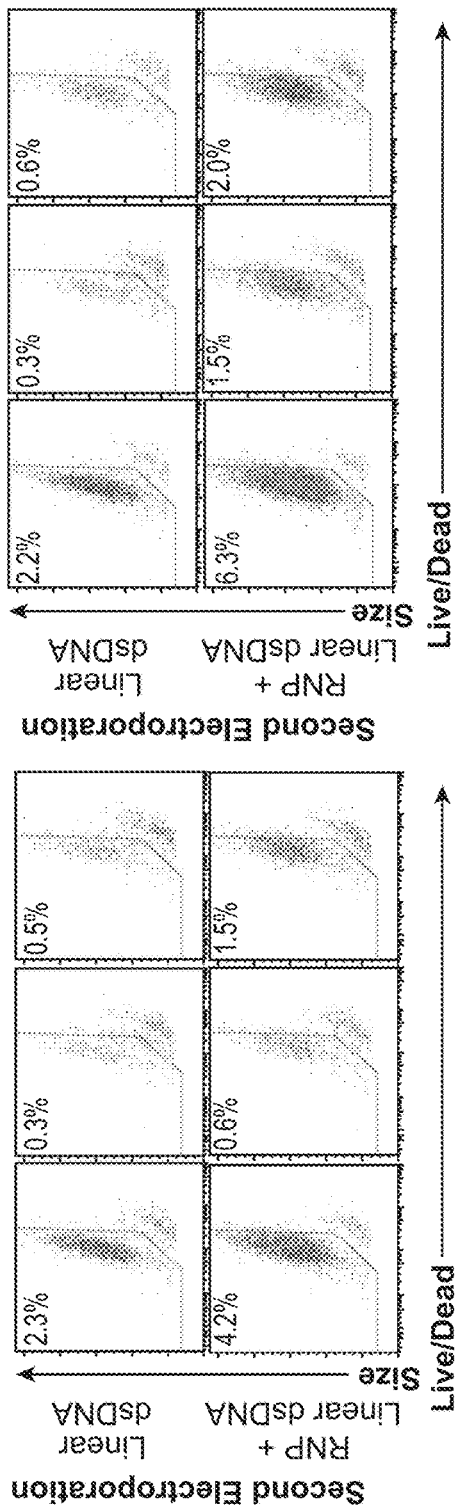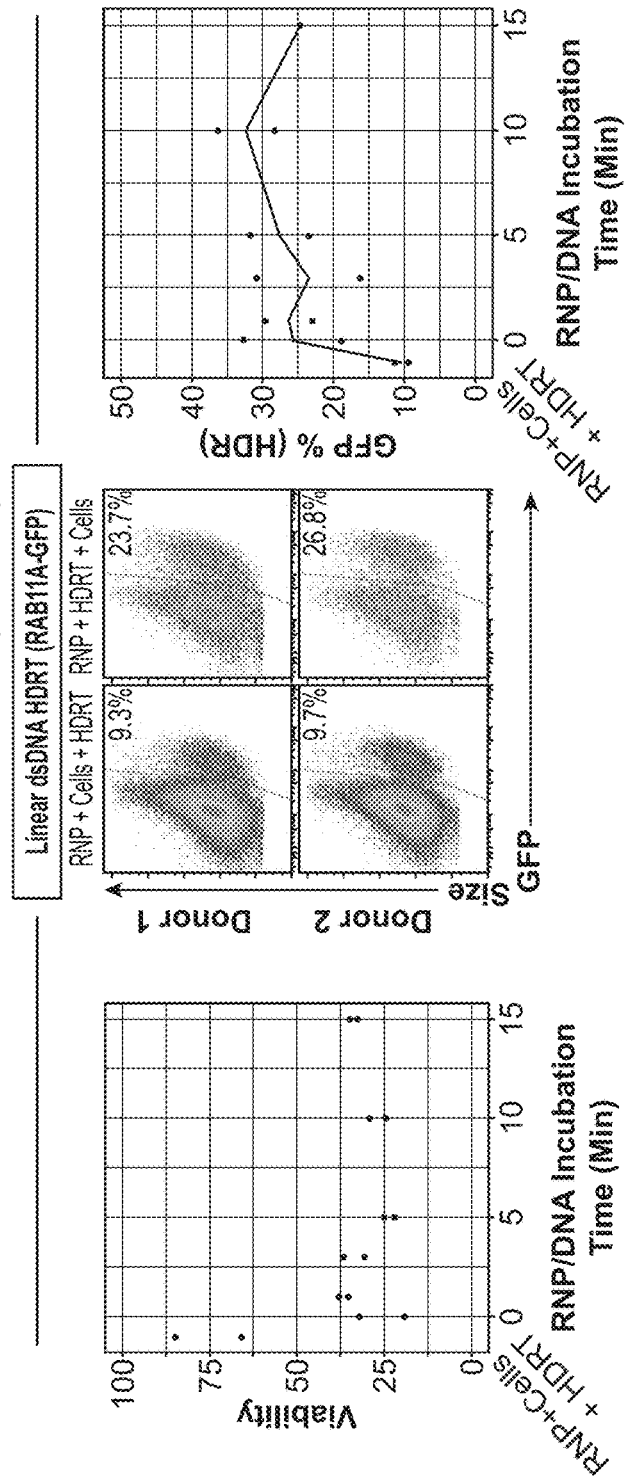
FIG. 10C
FIG. 10C (Cont.)
FIG. 10D
FIG. 10E
FIG. 10F

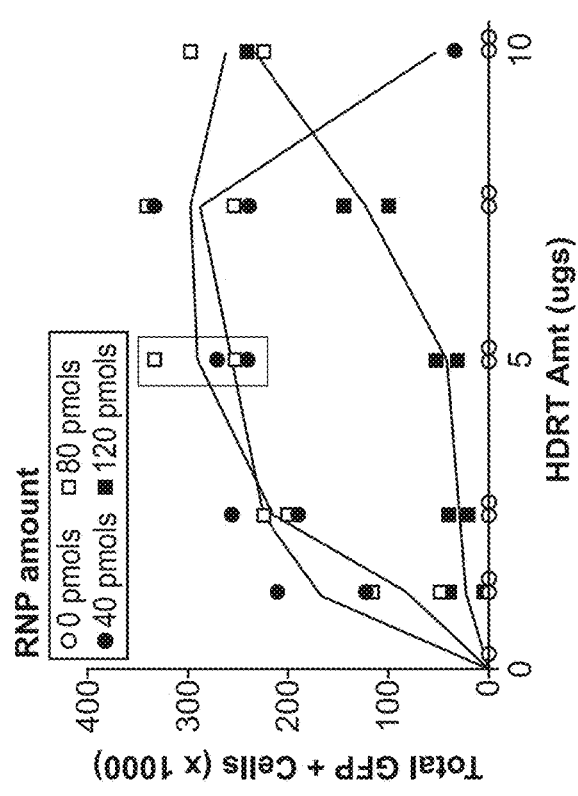
FIG. 11B
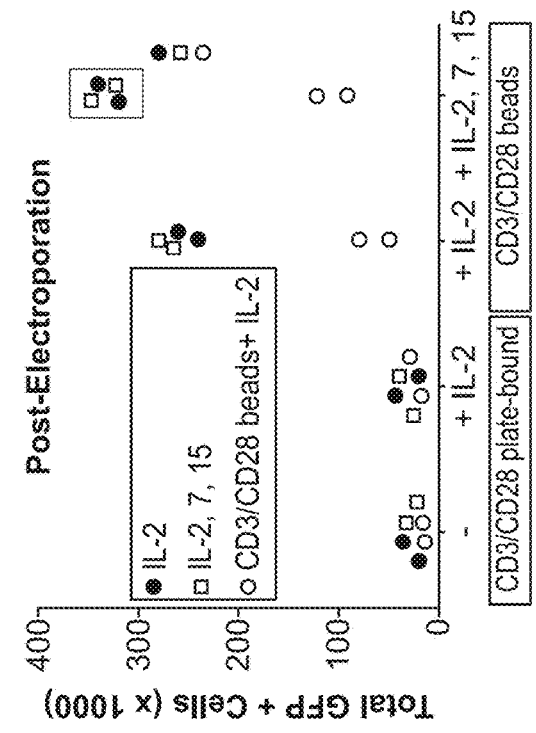
FIG. 11D
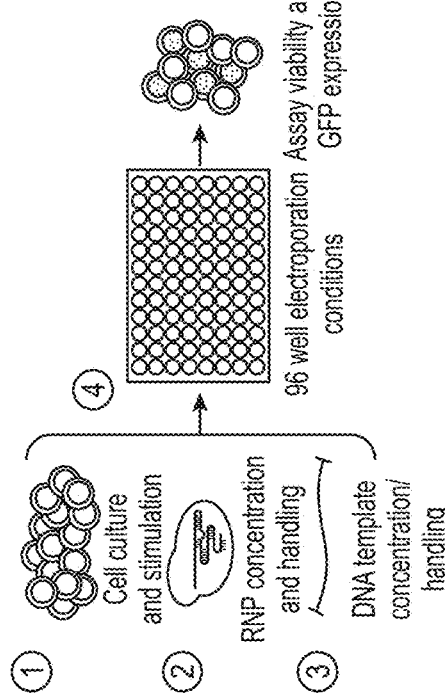
FIG. 11A
FIG. 11C

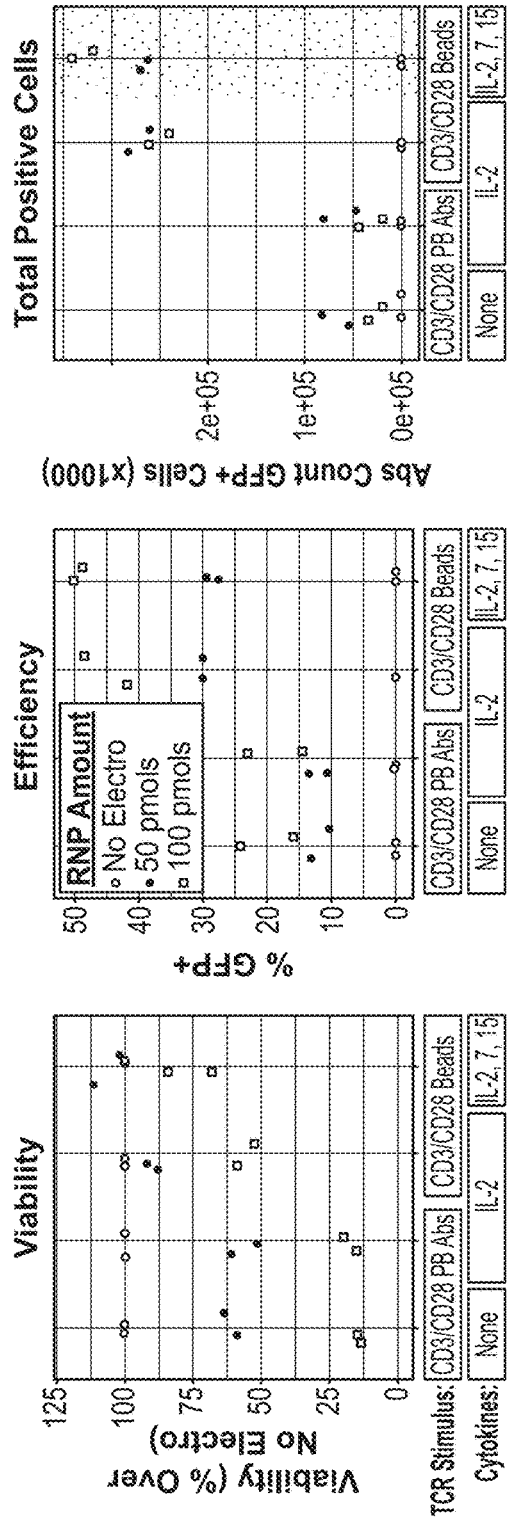
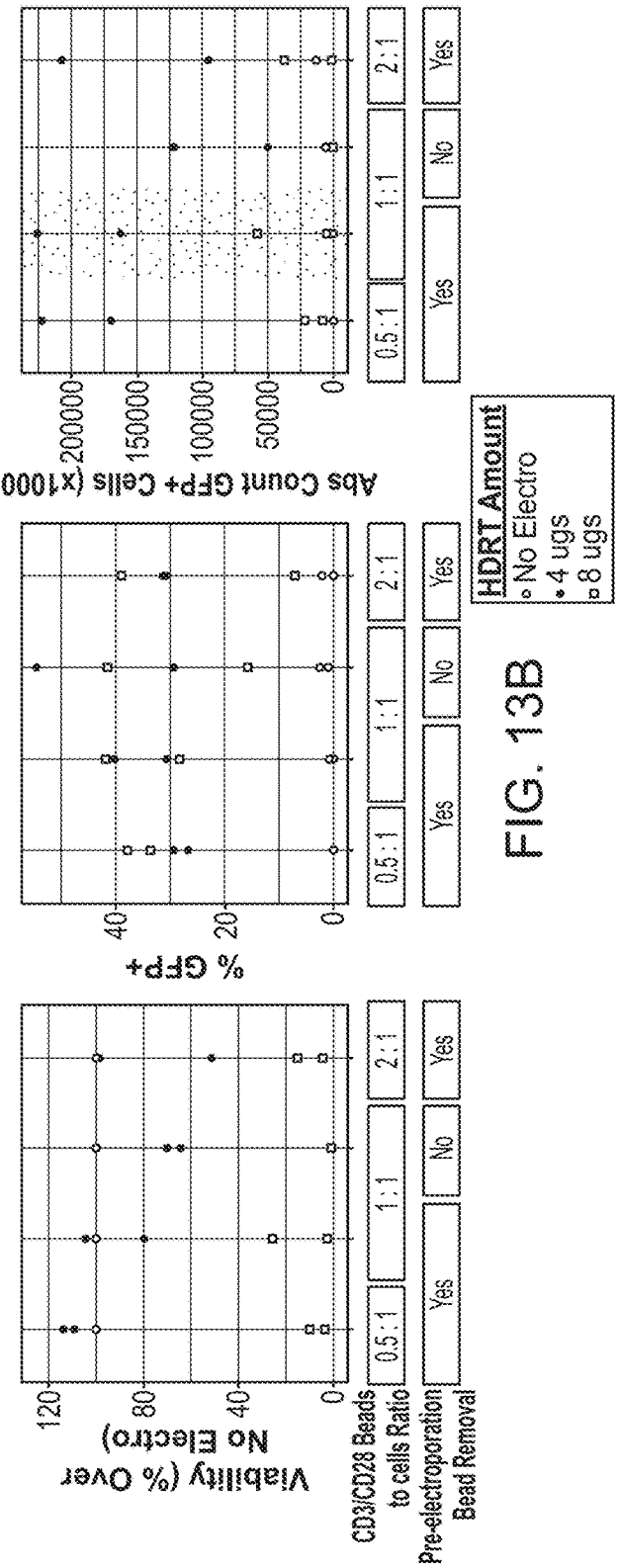
FIG. 13A
FIG. 13B

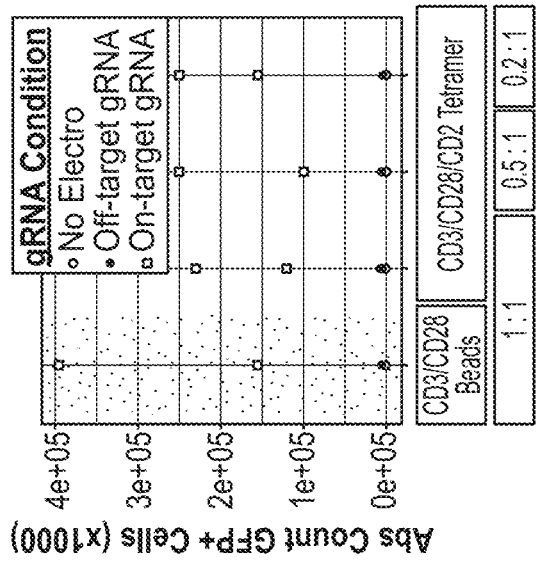
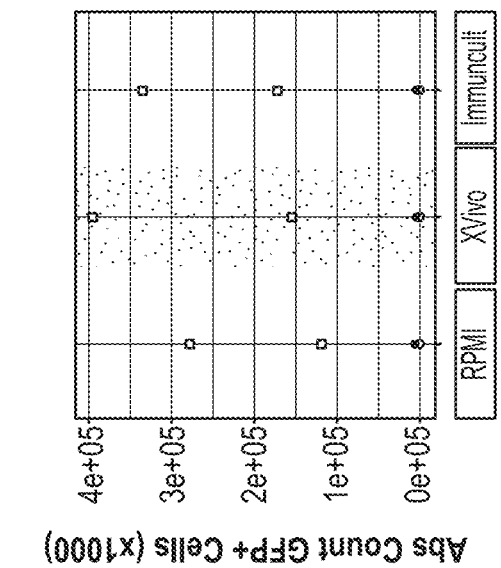
FIG. 13C
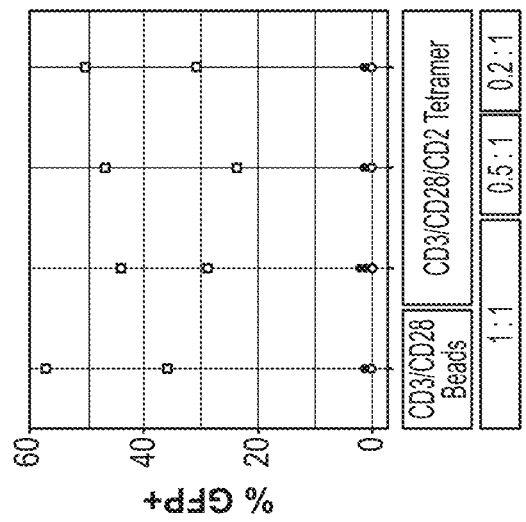
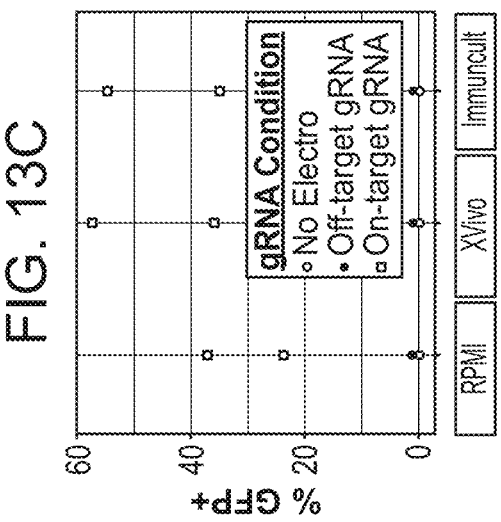
FIG. 13D
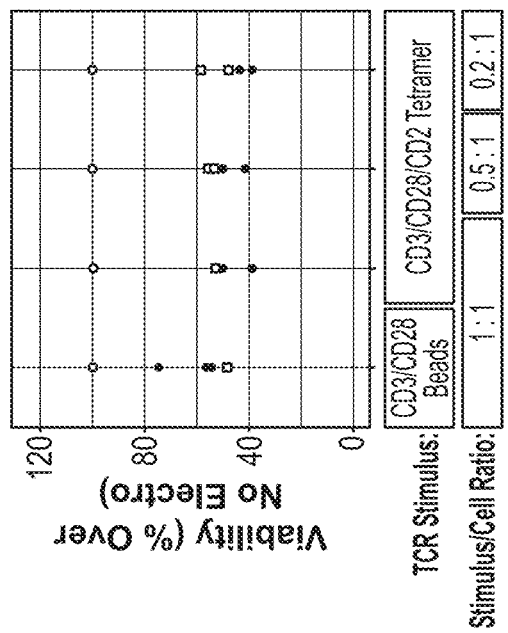
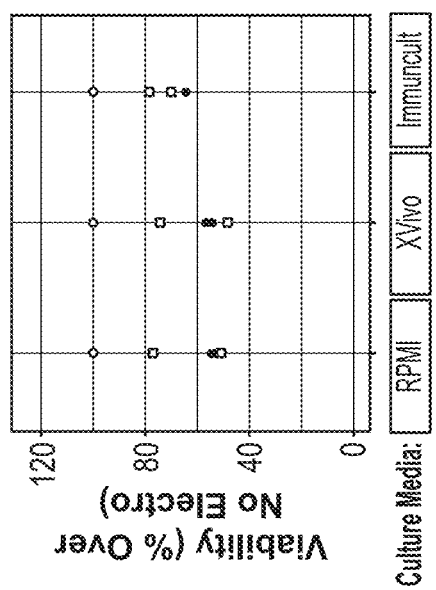

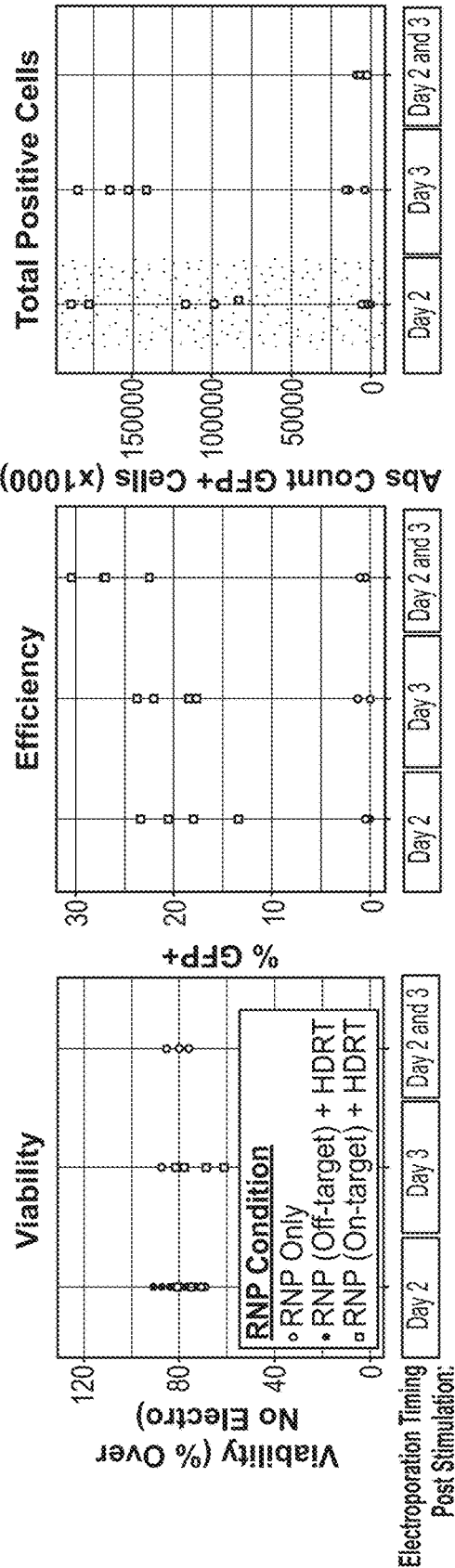
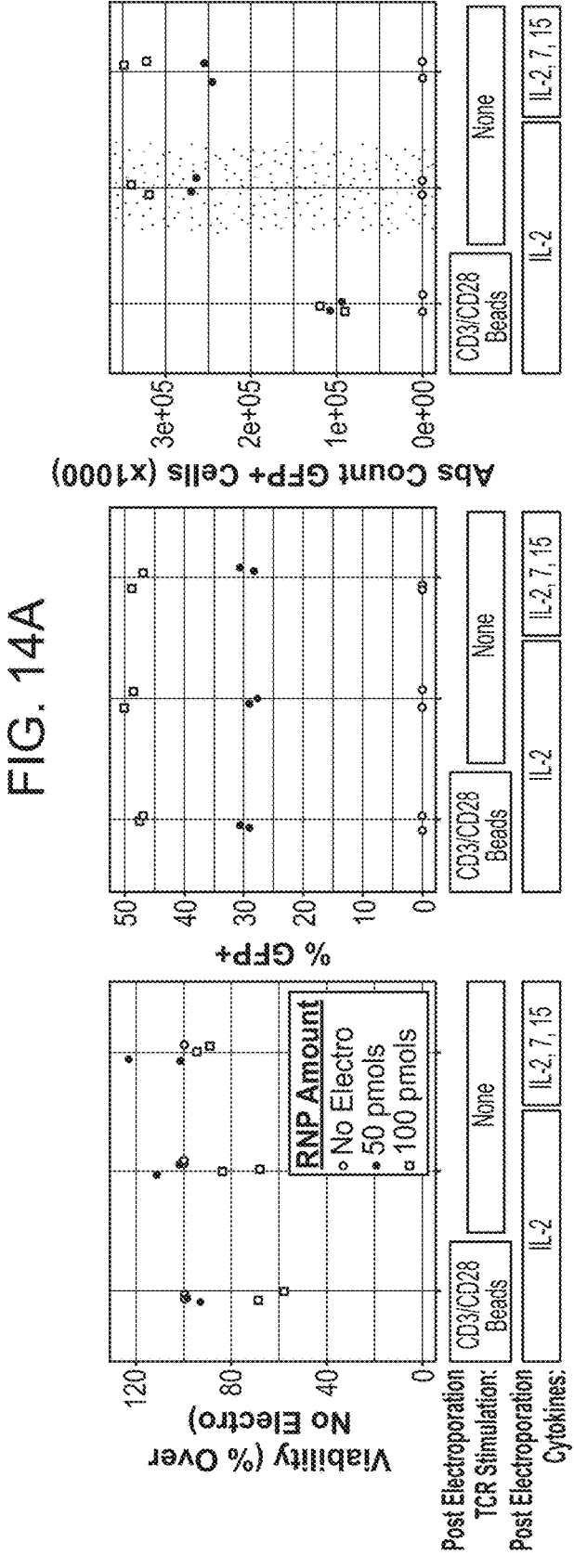
FIG. 14A
FIG. 14B

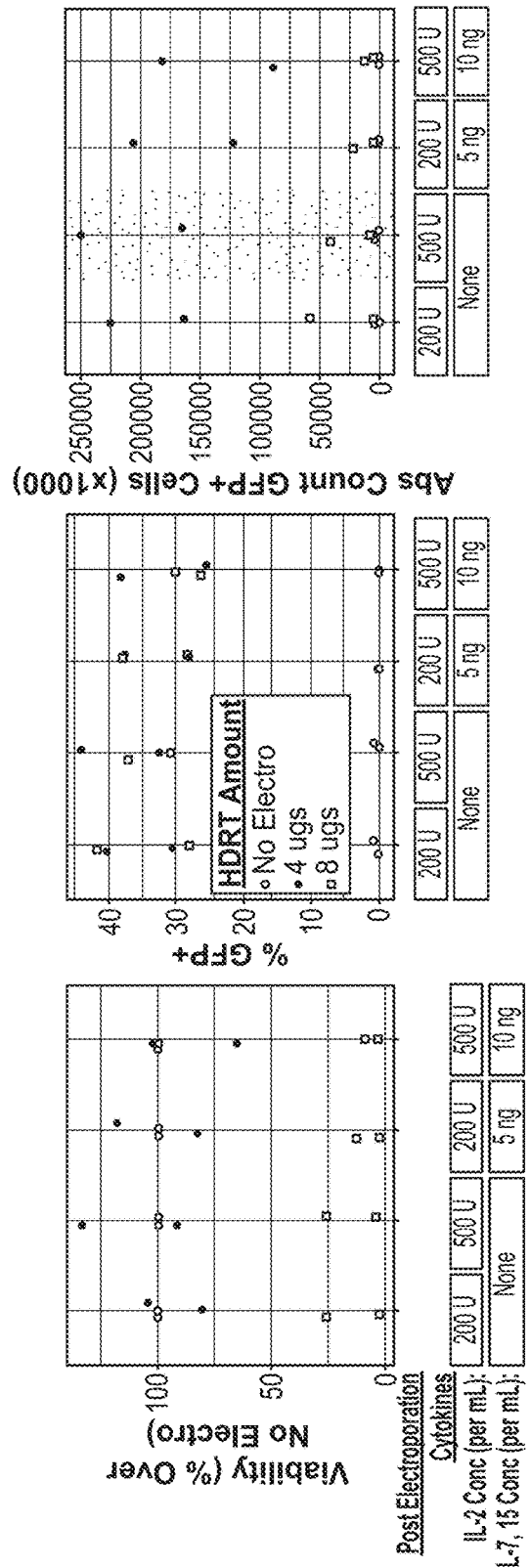
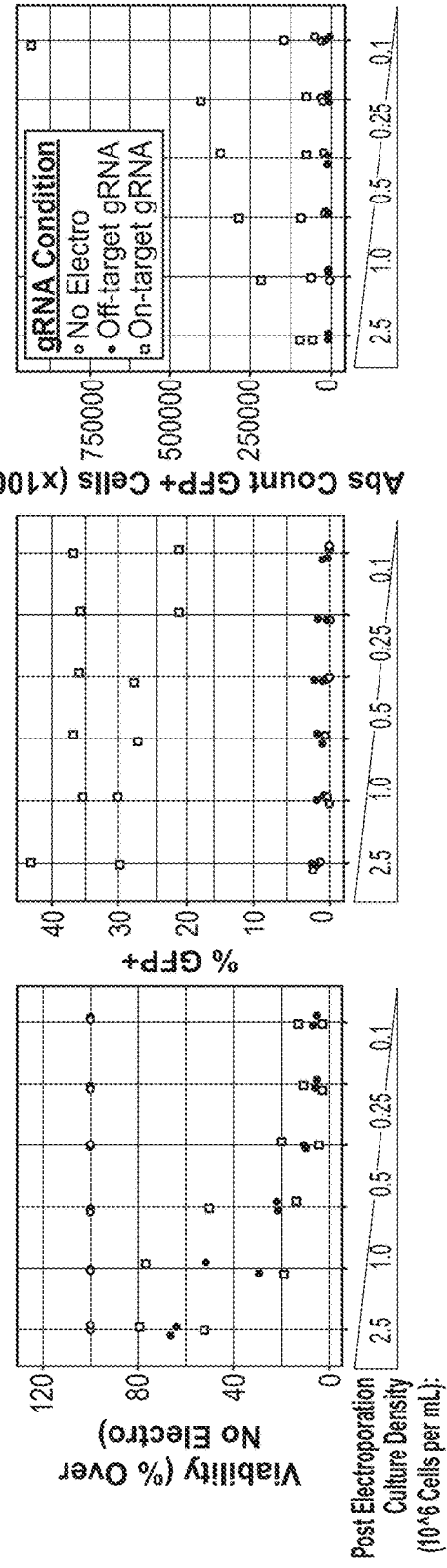
FIG. 14C
FIG. 14D

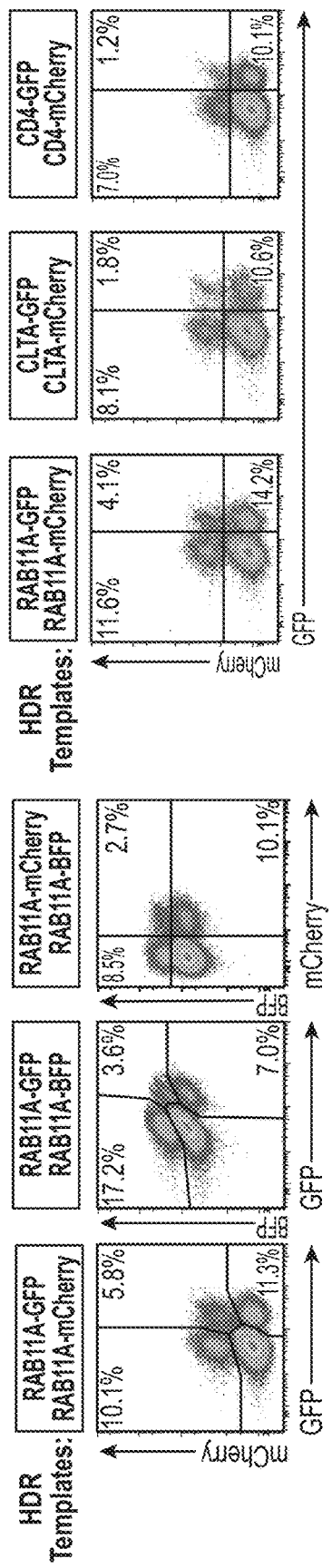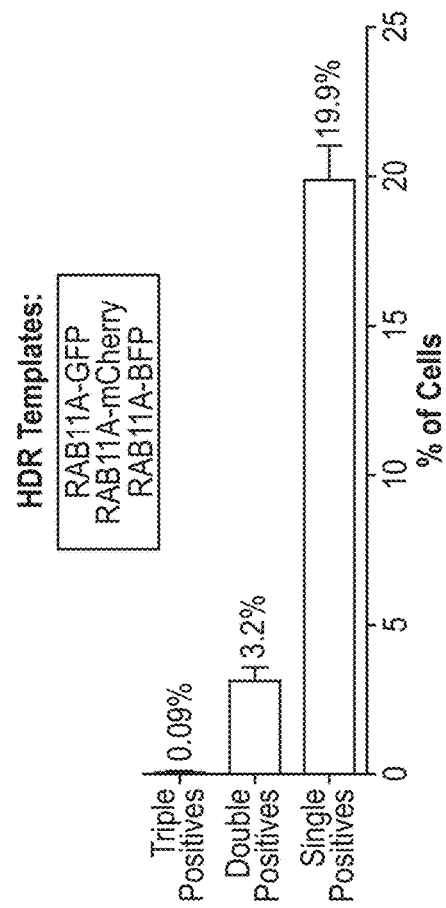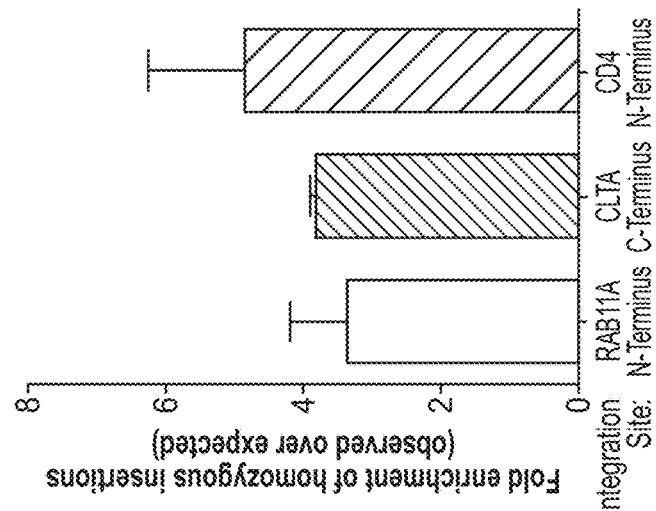
FIG. 23D
FIG. 23E
FIG. 23F
FIG. 23G

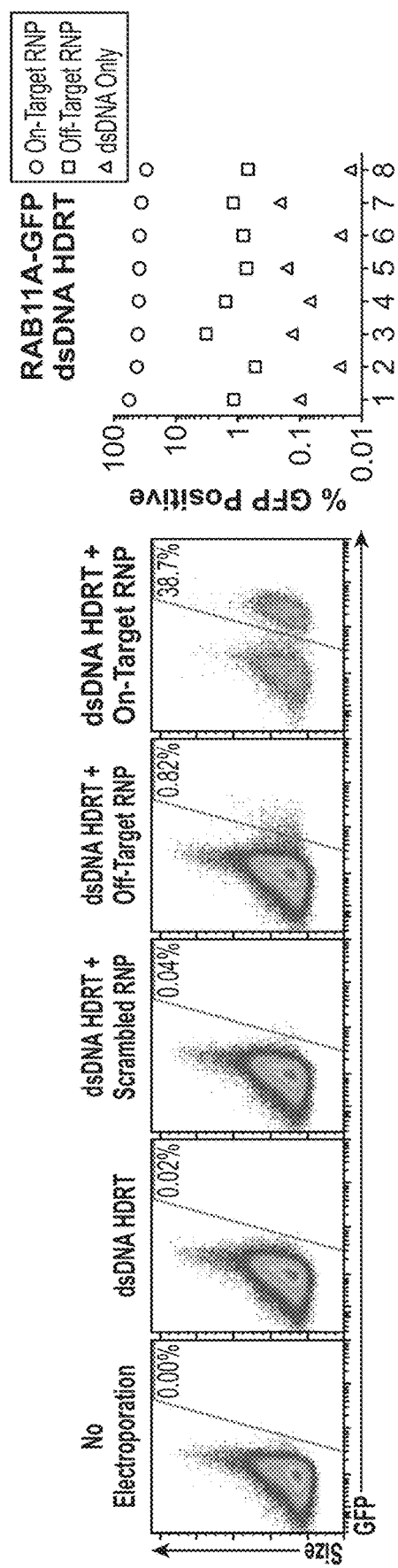
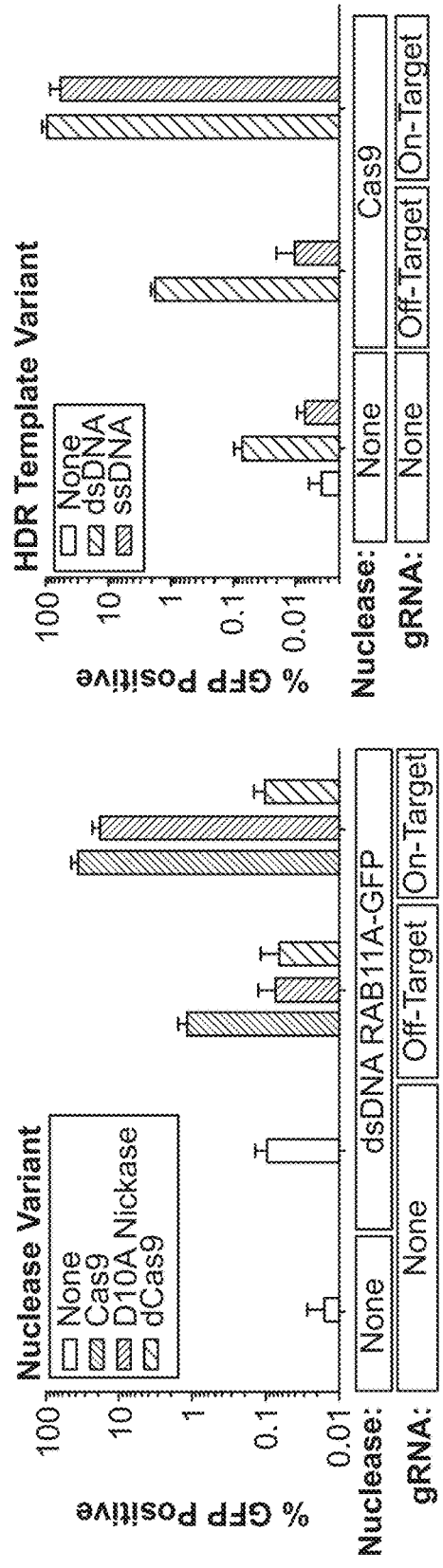
FIG. 25A
FIG. 25B
FIG. 25C
FIG. 25D

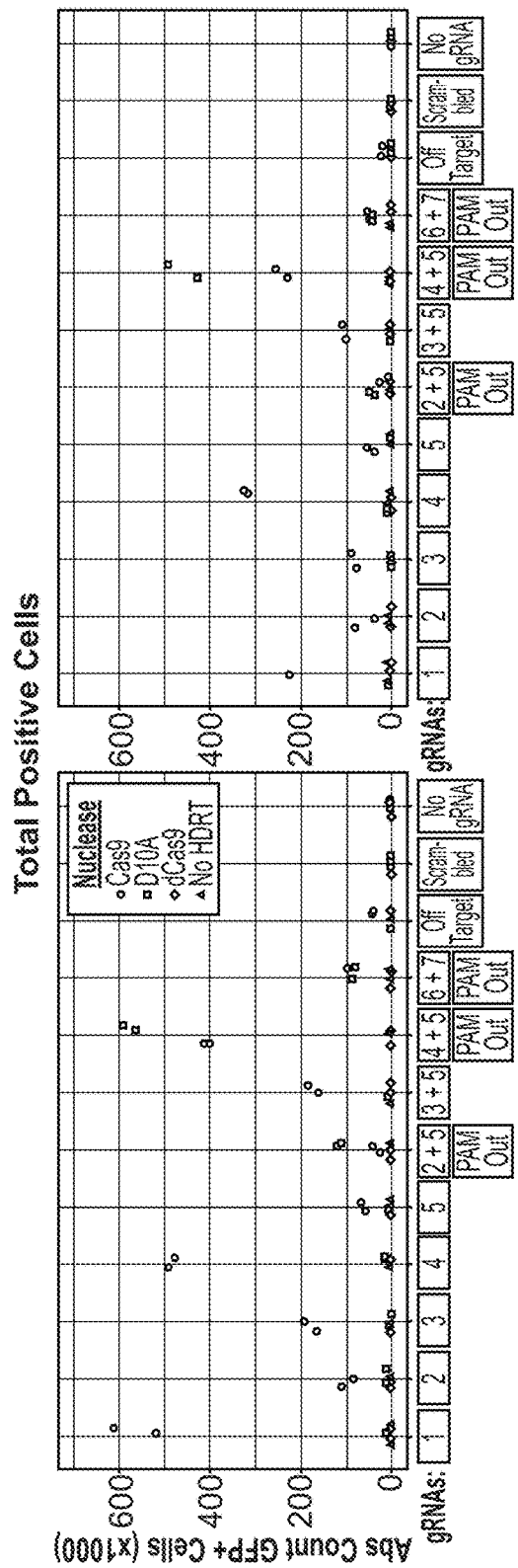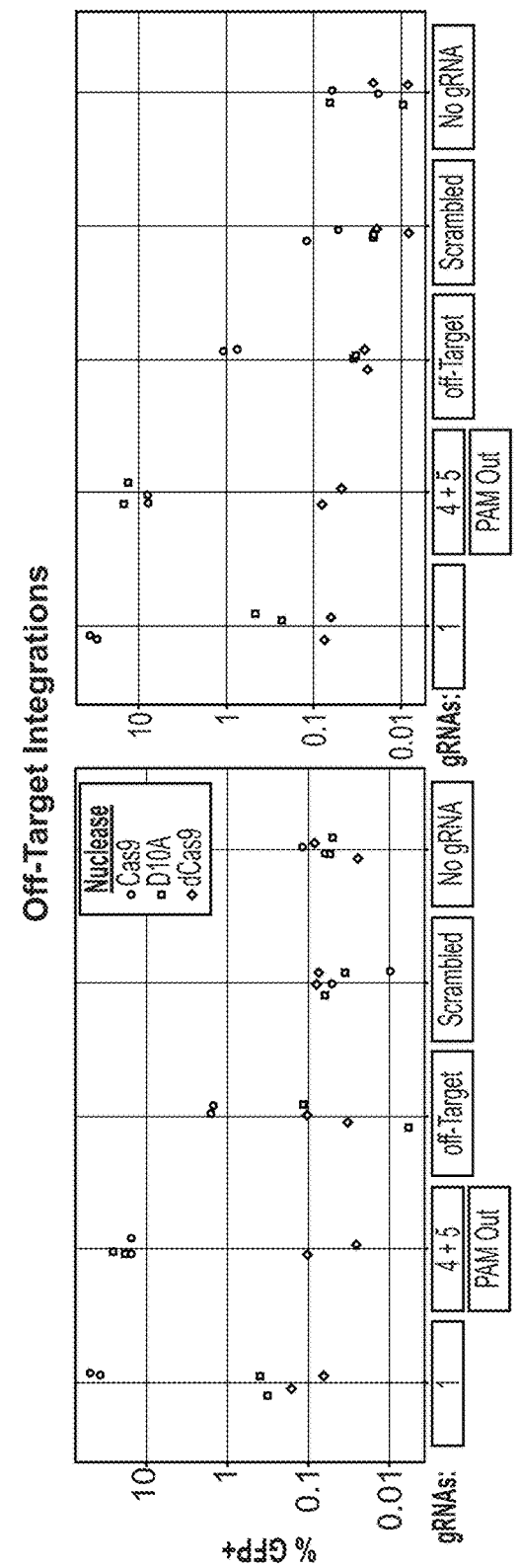
FIG. 28C
FIG. 28D

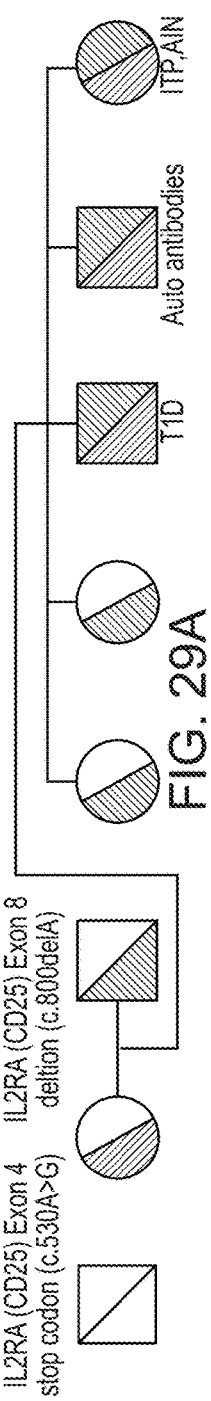
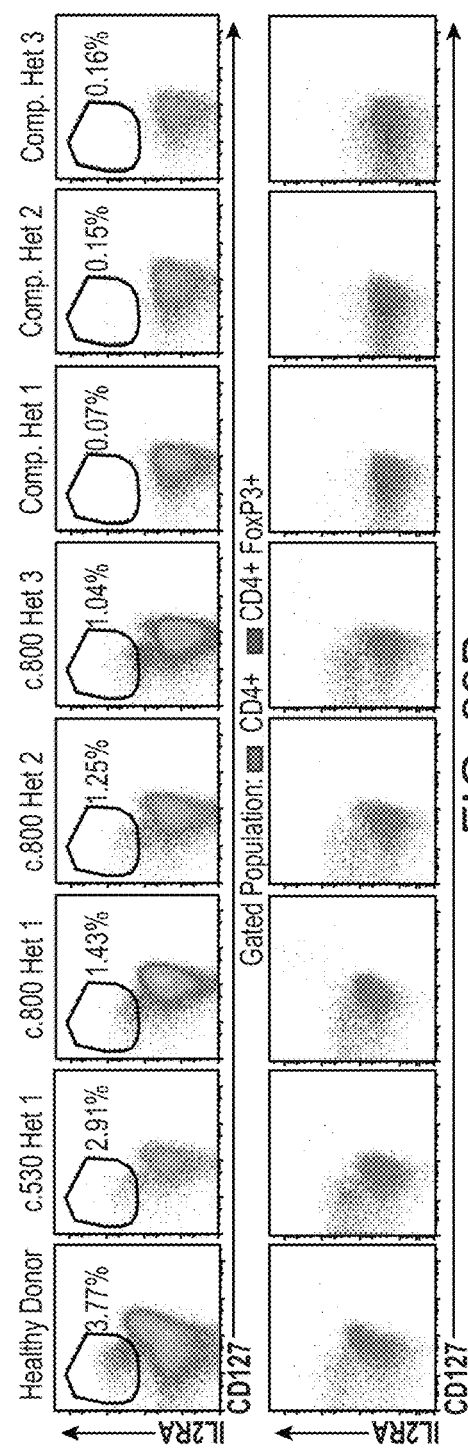
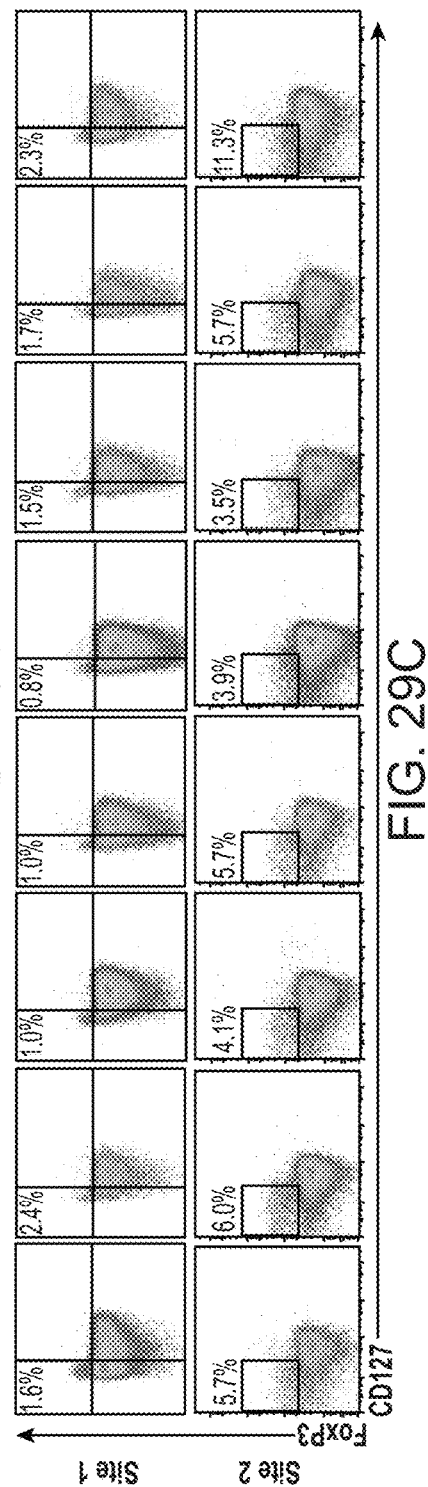
FIG. 29A
FIG. 29B
FIG. 29C

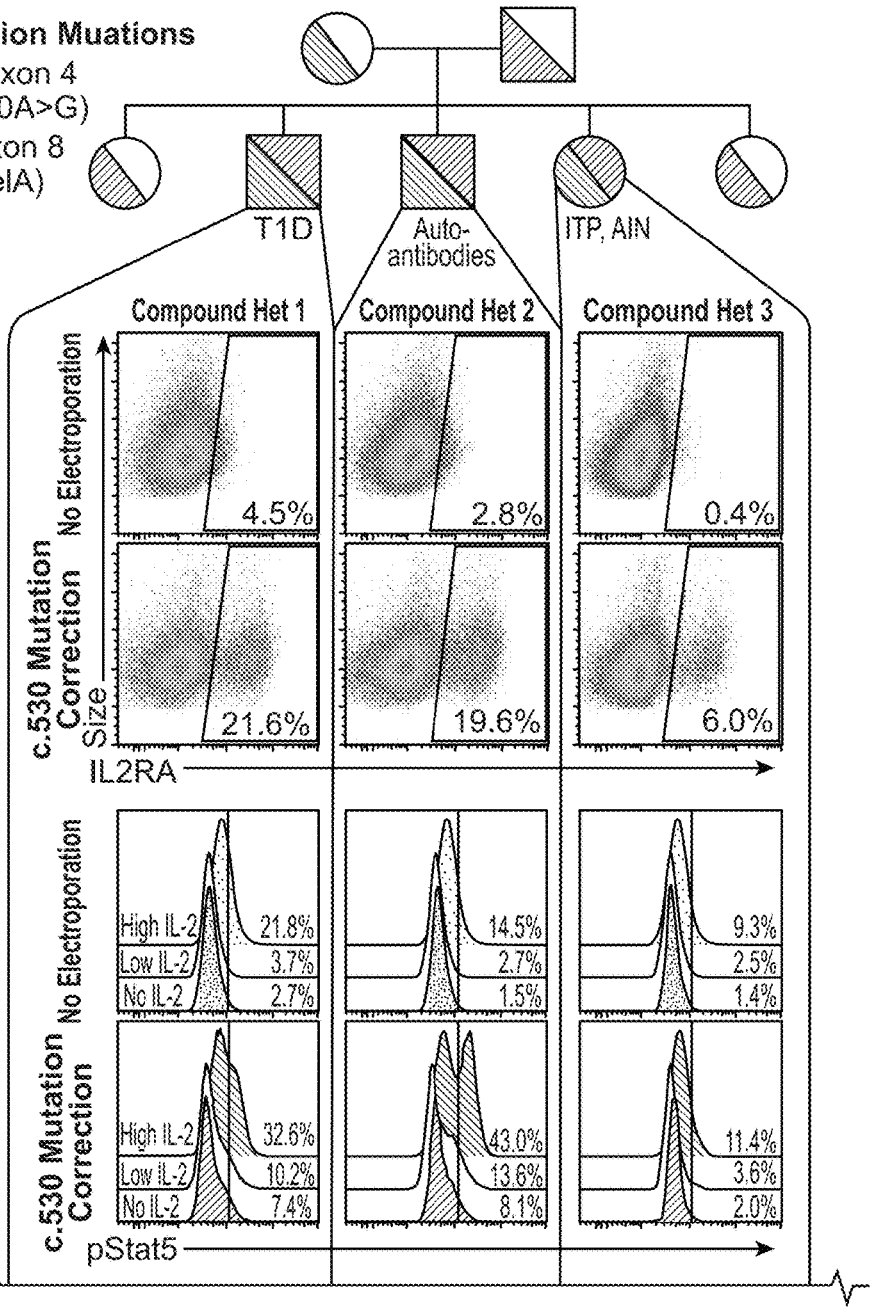
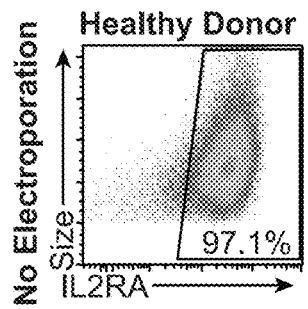
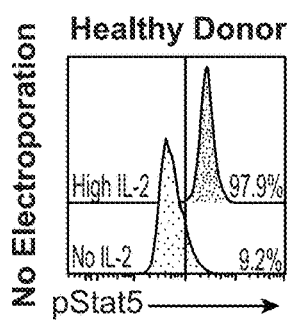
FIG. 30A
FIG. 30B
FIG. 30C

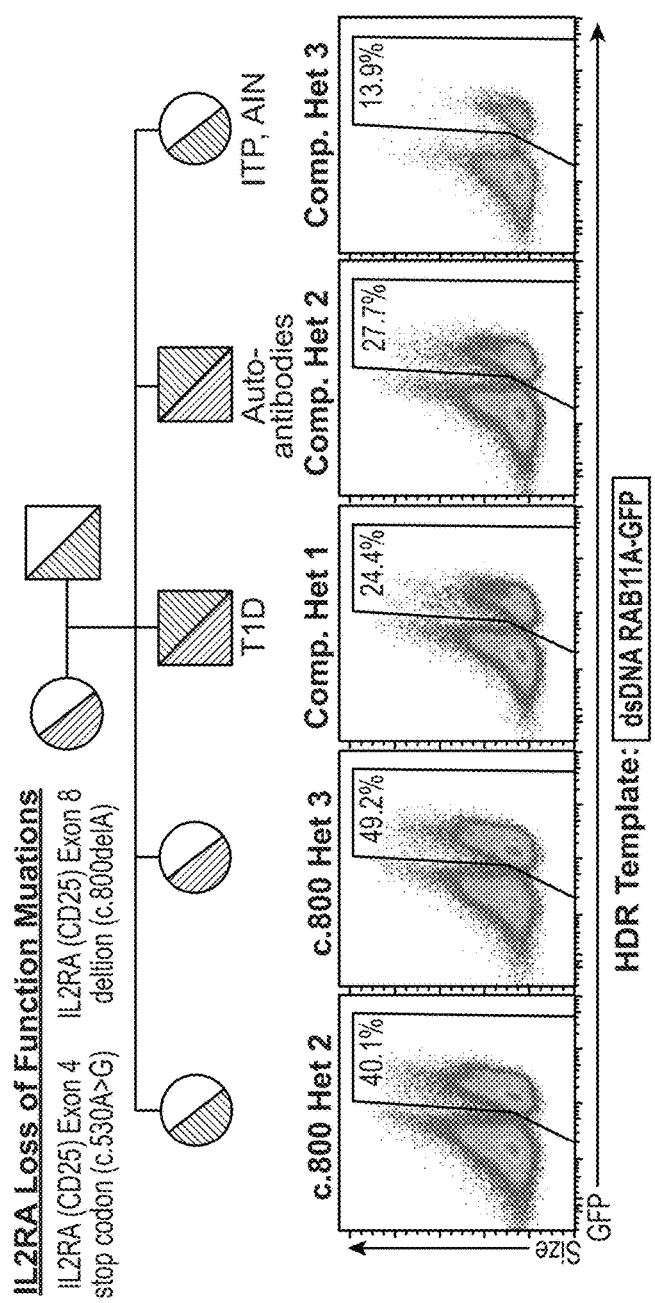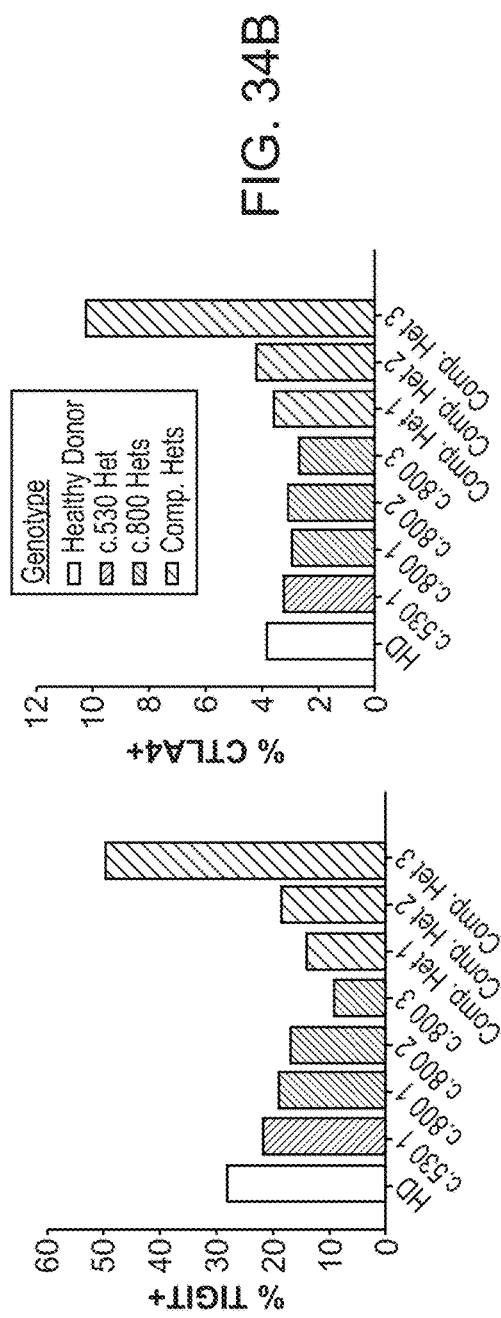
FIG. 34A
FIG. 34B

SEQUENCE LISTING

```
Sequence total quantity: 10
SEQ ID NO: 1            moltype = DNA  length = 19
FEATURE                 Location/Qualifiers
source                  1..19
                        mol_type = other DNA
                        organism = Synthetic construct
SEQUENCE: 1
agacaaggtr gacccagcc                                                       19

SEQ ID NO: 2            moltype = DNA  length = 20
FEATURE                 Location/Qualifiers
source                  1..20
                        mol_type = other DNA
                        organism = Synthetic construct
SEQUENCE: 2
acaggaggar rrkwrraraa                                                      20

SEQ ID NO: 3            moltype = DNA  length = 32
FEATURE                 Location/Qualifiers
source                  1..32
                        mol_type = other DNA
                        organism = Synthetic construct
SEQUENCE: 3
caaaatgacc cacgggaaga caaggtagac cc                                        32

SEQ ID NO: 4            moltype = DNA  length = 31
FEATURE                 Location/Qualifiers
source                  1..31
                        mol_type = other DNA
                        organism = Synthetic construct
SEQUENCE: 4
gactttgtta caccactaca ggaggagagt a                                         31

SEQ ID NO: 5            moltype = DNA  length = 13
FEATURE                 Location/Qualifiers
source                  1..13
                        mol_type = other DNA
                        organism = Synthetic construct
SEQUENCE: 5
acaagatgga ccc                                                             13

SEQ ID NO: 6            moltype = DNA  length = 13
FEATURE                 Location/Qualifiers
source                  1..13
                        mol_type = other DNA
                        organism = Synthetic construct
SEQUENCE: 6
aggagaaaga gta                                                             13

SEQ ID NO: 7            moltype = DNA  length = 32
FEATURE                 Location/Qualifiers
source                  1..32
```

-continued

```
                        mol_type = other DNA
                        organism = Synthetic construct
SEQUENCE: 7
caaaatgacc cacgggaaga caagatggac cc                                32

SEQ ID NO: 8            moltype = DNA   length = 32
FEATURE                 Location/Qualifiers
source                  1..32
                        mol_type = other DNA
                        organism = Synthetic construct
SEQUENCE: 8
gactttgtta caccactaca ggagaaagag ta                                32

SEQ ID NO: 9            moltype = DNA   length = 150
FEATURE                 Location/Qualifiers
source                  1..150
                        mol_type = other DNA
                        organism = Synthetic construct
SEQUENCE: 9
gacgcccct ggtcccacag ataccactgc tgctcccgcc ctttcgctcc tcggccgcgc    60
aatgggcacc cgcgacgacg agtacgacta cctctttaaa ggtgaggcca tgggctctcg  120
cactctacac agtcctcgtt cggggacccg                                  150

SEQ ID NO: 10           moltype = AA    length = 13
FEATURE                 Location/Qualifiers
source                  1..13
                        mol_type = protein
                        organism = Synthetic construct
SEQUENCE: 10
MGTRDDEYDY LFK                                                     13
```

TARGETED NON-VIRAL DNA INSERTIONS

PRIOR RELATED APPLICATIONS

This application is a divisional of U.S. patent application Ser. No. 17/498,531, filed Oct. 11, 2021, which is a continuation of U.S. patent application Ser. No. 16/622,843 filed on Dec. 13, 2019, which is a US National Phase 371 application from PCT/US2018/037919, filed Jun. 15, 2018, which claims the benefit of U.S. Provisional Application No. 62/520,117 filed on Jun. 15, 2017 and U.S. Provisional Application No. 62/552,180 filed on Aug. 30, 2017, all of which are hereby incorporated by reference in their entireties.

STATEMENT AS TO RIGHTS TO INVENTIONS MADE UNDER FEDERALLY SPONSORED RESEARCH AND DEVELOPMENT

This invention was made with government support under grant no. P50 GM082250 awarded by the National Institutes of Health. The government has certain rights in the invention.

SEQUENCE LISTING

The instant application contains a Sequence Listing which has been submitted electronically in .xml format and is hereby incorporated by reference in its entirety. Said .xml copy, created on Sep. 8, 2023, is named 081906-1400911-226140US.xml and is 10 kilobytes in size.

BACKGROUND OF THE INVENTION

The ability to introduce small mutations (indels) at targeted sites in the genome of cells by electroporating a Cas9-gRNA complex (RNP) into the cells has been developed. However, since these mutations are random and introduced by non-homologous end joining, they can cause a protein to be knocked out of frame (Schumann et al. PNAS 112(33): 10437-10442 (2015)). Other methods have been developed to introduce a defined DNA sequence at a specified target site in the genome by electroporating a small ssDNA oligonucleotide (ssODN) produced by chemical synthesis. This allows for integration of very small amounts of exogenous DNA (usually from about 1 base pair (bp) to about 30 base pairs (bps)) via Homology Directed Repair (termed HDR), which is less efficient than NHEJ, but allows for the final sequence to be defined. However, since the size of these oligonucleotides is limited to the length of DNA that can be chemically synthesized (<about 200 bps), and a large fraction of that is taken up by homology arms, many applications cannot be served by this method due to the limited size of integrations. In addition to size limitations, it is well established that electroporation of naked DNA, in particular, naked DNA larger than about 200 bps, into cells often leads to massive cell death owing to the activation of intrinsic cellular defense mechanism (Cornu et al. *Nat. Med.* 23: 415-423 (2017); Hornung and Latz, *Nature Reviews Immunology* 10: 123-130 (2010); Zhao et al., *Mol. Ther.* 13(1): 151-159 (2006)). Although non-integrating viral vectors, such as integrase defective lentiviral vectors or adeno-associated viral (AAV) vectors, have been used to deliver large donor nucleic acid sequences to cells, these vectors require viral infection and cause off-target effects. Therefore, compositions and methods for targeted insertion of large nucleotide sequences into the genome of a cell are needed.

BRIEF SUMMARY OF TILE INVENTION

The present invention is directed to compositions and methods for editing the genome of a cell. The inventors have discovered that large nucleotide sequences, for example, sequences greater than about 200 nucleotides in length, can be inserted into a targeted region in the genome of a cell. In some methods, integration of sequences greater than about 200 nucleotides in length occurs while reducing off-target effects and/or reducing loss of cell viability.

In some embodiments, the present invention provides a method of editing the genome of a cell, the method comprising: a) providing a Cas9 ribonucleoprotein complex (RNP)-DNA template complex comprising: (i) the RNP, wherein the RNP comprises a Cas9 nuclease domain and a guide RNA, wherein the guide RNA specifically hybridizes to a target region of the genome of the cell, and wherein the Cas9 nuclease domain cleaves the target region to create an insertion site in the genome of the cell; and (ii) a double-stranded or single-stranded DNA template, wherein the size of the DNA template is greater than about 200 nucleotides, wherein the 5' and 3' ends of the DNA template comprise nucleotide sequences that are homologous to genomic sequences flanking the insertion site, and wherein the molar ratio of RNP to DNA template in the complex is from about 3:1 to about 100:1; and b) introducing the RNP-DNA template complex into the cell.

In some embodiments, the DNA template is a linear DNA template. In some examples, the DNA template is a single-stranded DNA template. In certain embodiments, the single-stranded DNA template is a pure single-stranded DNA template.

In some embodiments, the RNP-DNA template complex is formed by incubating the RNP with the DNA template for about one to about thirty minutes, at a temperature of about 20° to 25° C. In some embodiments, the RNP-DNA template complex and the cell are mixed prior to introducing the RNP-DNA template complex into the cell.

In some embodiments, the RNP comprises a Cas9 nuclease. In some embodiments, the RNP comprises a Cas9 nickase. In some embodiments, the RNP-DNA template complex comprises at least two structurally different RNP complexes. In some embodiments, the at least two structurally different RNP complexes contain structurally different Cas9 nuclease domains In some embodiments, the at least two structurally different RNP complexes contain structurally different guide RNAs. In some embodiments, wherein the at least two structurally different RNP complexes contain structurally different guide RNAs, each of the structurally different RNP complexes comprises a Cas9 nickase, and the structurally different guide RNAs hybridize to opposite strands of the target region.

In some embodiments, introducing the RNP-DNA template complex into the cell comprises electroporation. In some embodiments, the molar ratio of of RNP to DNA template is from about 5:1 to about 15:1. In some embodiments, the molar ratio of RNP to DNA template is from about 5:1 to about 10:1. In some embodiments, the molar ratio of RNP to DNA template is from about 8:1 to about 12:1. In some embodiments, the DNA template is at a concentration of about 2.5 pM to about 25 pM. In some embodiments, the size of the DNA template is greater than about 1 kb. In some embodiments, the amount of DNA template is about 1 µg to about 10 µg.

In some embodiments, the RNP-DNA template complex is introduced into about 1×10⁵ to about 2×10⁶ cells. In some embodiments, the cell is a primary hematopoietic cell or a primary hematopoietic stem cell. In some embodiments, the primary hematopoietic cell is an immune cell. In some embodiments, the immune cell is a T cell. In some embodiments, the T cell is a regulatory T cell, an effector T cell, or a naïve T cell. In some embodiments, the T cell is a CD8$^+$ T cell. In some embodiments, the T cell is a CD4$^+$CD8$^+$ T cell.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIGS. 10A-F show that CRISPR/Cas9 RNP co-electroporation reduces dsDNA induced viability loss. (A) A linear dsDNA template (a homology directed repair template, 1350 bps long, targeting a GFP fusion to RAB11A, FIG. 11A) electroporated into primary human T cells cause marked viability loss with increasing amounts of template. Electroporation of the same amount of dsDNA template along with 100 pmols of RNP surprisingly increased viability. (B) For both plasmid and linear dsDNA templates, addition of an RNP increased viability post electroporation. Of note, no loss in viability was seen with short ssDNA oligo donor nucleotides (ssODNs). (C) RNPs must be delivered concurrently with DNA to see increased viability. T cells from two donors were each electroporated twice with an eight hour rest in between electroporations. While two electroporations so closely interspersed caused a high degree of cell death, delivery of the RNP and linear dsDNA template could be delivered separately. However, an initial RNP electroporation did not increase viability when a DNA template was subsequently electroporated in comparison to cells that received DNA first and RNP second. (D-F) Given that the RNP and DNA needed to be introduced concurrently, we assayed whether additional pre-incubation together before electroporation would further increase viability. No difference in viability was seen with increasing pre-incubation time (0 to 15 minutes), but surprisingly if the RNP and cells were mixed first and the DNA template was added immediately prior to elecroporation (RNP+Cells; +HDRT) viability was increased (E). However, in wells where the RNP and the DNA HDR template were mixed together prior to adding the cells (RNP+HDRT; +Cells), no matter how long the RNP and DNA template were preincubated, there was a drastic increase in HDR percentage (GFP+ cells). Viability was measured 2 days following electroporation and GFP expression was measured at day 4. Graphs (B, D, F) display data from 2 healthy human donors.

FIGS. 11A-F show the development of efficient large non-viral gene targeting. (A) Systematic analysis of the effects of cell culture and stimulation conditions, RNP and DNA template formulations, and electroporation conditions via 96-well high-throughput electroporations enabled rapid optimization of both cell viability (total number of live cells in culture) and HDR efficiency (% of cells GFP positive). (B) Schematic of a long (1350 bp) linear dsDNA template encoding a GFP sequence flanked by regions homologous to the N-terminus of the housekeeping gene RAB11A (not drawn to scale). When a dsDNA break is induced at the N-terminus of RAB11A, the GFP sequence can be seamlessly introduced via homology directed repair (HDR) to generate an endogenously-tagged RAB11A-GFP fusion protein. (C) Primary human T cells were cultured for 2 days using varying combinations of T cell receptor (TCR) stimulation and cytokines prior to electroporation of RAB11A targeting RNP and HDR template, followed by varying culture conditions for 5 days post-electroporation. (D) Among RNP and HDR template concentrations tested here, optimal GFP insertion into RAB11A was achieved at intermediate concentrations of the reagents. Further testing (FIG. 16) narrowed optimal concentrations to 50 pmols of RNP and 4 ugs of dsDNA HDRT. (E) Arrayed testing of electroporation pulse conditions showed that, in general, conditions yielding higher HDR efficiency decreased viability. EH115 was selected to optimize HDR, while still maintaining sufficient viability. (F) Using parameters optimized in C-D, high-efficiency insertion of GFP into the endogenous RAB11A gene was achieved by non-viral targeting in both primary human CD4$^+$ and CD8$^+$ T cells. Viability and efficiency were assayed 3 days (E) or 5 days (C, D, and F) after electroporation. Individual points represent individual blood donors (C and D) or the mean plus standard deviation in two individual donors (E). Green highlights indicate conditions ultimately chosen for the non-viral gene targeting protocol.

FIGS. 13A-D show optimization of primary human T cell stimulation for non-viral gene targeting. (A) Alternative pre-electroporation stimulation conditions were applied for two days prior to electroporation. CD3/CD28 bead bound stimulation along with a cytokine stimulation cocktail of IL-2, IL-7, and IL-15 achieved higher viability, rates of editing, and total positive cells than plate bound antibody stimulation. (B) Alternative ratios of beads to cells showed an optimal 1:1 ratio along with removal of beads prior to electroporation. (C) Non-bead based CD3/CD28/CD2 stimulation yielded lower editing efficiencies than CD3/CD28 beads at optimal ratio. (D) Commercial XVivo15 media achieved similar viability but higher editing efficiencies compared to RPMI. Of interest, the serum-free Immunocult media also enabled high-efficiency editing of human primary CD3$^+$ T cells. Efficiency of GFP insertion (dsDNA RAB11A-GFP HDRT) and the absolute count of total GFP+ cells was performed 4 days following electroporation. Two dots per condition represent the values obtained from two healthy blood donors.

FIGS. 14A-D show optimization of primary human T cell handling post-electroporation. (A) Electroporation of CD3$^+$ T cells from healthy human donors at day 2 or day 3 post stimulation achieved efficient targeted GFP integration. Dual electroporations at both days, while increasing efficiency slightly, drastically reduced the viability when a DNA template was included in the two electroporations (FIG. 10). (B) Additional CD3/CD28 stimulation after electroporation reduced proliferative potential. (C) High doses of IL-2 post-electroporation improved both efficiency and viability. Further addition of IL-7 and IL-15, unlike during pre-electroporation stimulation (FIG. 13) did not contribute to improved editing. (D) Post culture density has little effects on insertion efficiency. Efficiency of GFP insertion (dsDNA RAB11A-GFP HDRT) and the absolute count of total GFP+ cells was performed 4 days following electroporation. Two dots per condition represent the values obtained from two healthy blood donors.

FIGS. 23A-G show modeling and analysis of bi-allelic HDR integrations by insertion of multiple fluorescent proteins into the same locus. (A) The possible cellular phenotypes when two fluorescent proteins are inserted into the same locus. (B) The genotypes of two of these phenotypic populations are immediately known. Cells without any functional insertions (bottom left quadrant, genotype A), must have a NA/NA genotype (where NA indicates an allele without HDR, including WT alleles and NHEJ edited alleles). Dual fluorescent cells (top right quadrant, genotype E) must have acquired one copy of each template (assuming an autosomal target locus and no off-target integrations), and would have a genotype of GFP/RFP. The two single positive populations though will be mixed between cells heterozygous for HDR insertion (Genotypes B and C) or homozygous but for two copies of the same fluorescent template (Genotypes D and F). (C) The total percentage of cells with bi-allelic HDR integrations must be the sum of genotypes D, E, and F. While the proportion of cells with genotype E (dual fluor positives) is immediately apparent from the phenotypes, genotypes D and F are not. Application of a simple probability model allow for the de-convolution of the multiple genotypes in the single fluor positive phenotypes, and thus an estimation of the true percentage of cells homozygous for HDR. (D) Bi-allelic HDR analysis applied across a variety of fluorophore permutations inserted into the RAB11A locus. (E-F) Dual fluorescence bi-allelic integrations were seen across target loci. While the total percentage of cells with an insertion varied with the efficiency of each target site, the fold enrichment in the observed percentage of homozygous cells over that predicted by random chance was consistent across loci. (G) Attempted integration of three distinct fluorophores by HDR into the same locus. As a max of two targeted insertions are possible (at the locus' two alleles; assuming a diploid genome), no cells positive for all three loci should be observed (triple positives). Indeed, while large numbers of single fluorophore integrations are observed (single positives), as well as cells positive for the various permutations of two fluors (double positives), there is a 30 fold reduction in the number of triple positive cells compared to double positives. All flow cytometric analysis of fluorescent protein expression was performed 4 days following electroporation. Displays are representative of multiple technical replicates from one (E, F) or two (D, G) healthy human donors. Bar graphs display mean+standard deviation.

FIGS. 25A-F show D10A nickase and ssDNA HDR templates reduce off-target integrations. (A) Combinations of Cas9 RNPs and a RAB11A-GFP dsDNA HDR template were electroporated into primary human T cells. dsDNA template alone, or with an RNP containing a scrambled gRNA matching no sequence in the human genome yielded small but detectable amounts of GFP expression, which was noticeably increased when a dsDNA template is electroporated with a gRNA targeting a site different from the targeted RAB11A-GFP integration site (the "off-target RNP" targets CXCR4 Exon 1). (B) Off-target integrations were consistently present in cells from different donors when the RAB11A-GFP dsDNA HDR template was electroporated with the off-target RNP, and fewer off-target integrations occurred when the dsDNA HDR template alone was electroporated. (C) Cas9 nuclease variants D10A (nickase) and inactive dCas9 significantly decreased off-target integrations when a single off-target CXCR4 gRNA was used, but D10A nickase (with an "On-target" pair of gRNAs in a PAM-out orientation) led to efficient on-target integration of the RAB11A dsDNA HDR template. (D) Electroporation of a ssDNA HDR template reduced the off-target integrations to the limit of detection (comparable to levels with no template electroporated) both with no nuclease added and at induced off-target dsDNA breaks (Off-target gRNA+Cas9). (E-F) For integration of GFP fusion at the RAB11A site, use of a D10A nickase with a ssDNA HDR template reduced the on-target HDR (GFP integration with on-target gRNA) compared to Cas9 with a dsDNA template, but strongly reduced off-target integrations to undetectable levels. All fluorescent readouts were performed 4 days post-electroporation. Displayed data is representative of at least two different donors (A and E) or the averages of two different donors (C, D, and F) with standard deviation shown

FIGS. 28A-D show efficient HDR in primary human T cells using a Cas9 nickase. (A) Diagram of the genomic locus containing the first exon of RAB11A. Use of spCas9 with a single guide RNA (gRNA 1) along with a dsDNA HDR template integrating a GFP in frame with RAB11A directly after the start codon results in efficient GFP expression (FIG. 11F). Use of a Cas9 nickase (D10A variant) with two gRNAs could reduce the chances of off-target cutting. (B-C) A series of single gRNAs as well as dual gRNA combinations were tested for GFP insertion efficiency at the RAB11A N-terminal locus. As expected, no gRNAs showed appreciable levels of GFP insertion when using a nuclease dead Cas9 (dCas9). Multiple single gRNAs cutting adjacent to the insertion site showed GFP integration when using Cas9, but none as efficiently as gRNA 1. The D10A nickase showed little to no GFP integration with single guides, but with multiple two-guide combinations showed efficient GFP integration. Only in gRNA combinations where the two PAM sequences were directed away from each other (PAM Out) was GFP integration seen. (D) Raw data presented in (FIG. 25C) demonstrating lower levels of functional off-target integrations when electroporating an off-target gRNA (targeting CXCR4), likely due to the requirement for the D10A nickase to have two gRNAs binding in close proximity to induce a dsDNA break. Dots in all displays (B-D) represent technical replicates in the labeled two healthy donors.

FIGS. 29A-H show reduced Treg frequencies and defective Treg suppressive capacity in subjects with two loss of function IL2RA mutations. (A) CD3+CD4+ T cells from a healthy donor and all family members, including IL2RA heterozygotes (c.530 het 1, c.800 hets 1-3) as well as compound heterozygote children (Comp. Hets 1-3), with loss-of-function IL2RA mutations were analyzed by flow cytometry to assess presence of CD25hiCD127lo Tregs. (B) In healthy donors and single hets, CD4+FoxP3+ T cells are predominantly CD25hiCD127lo. In the compound heterozygotes, a CD127lo CD4+FoxP3+ population is present, but does not express IL2RA. (C) Clinical phenotyping performed at two separate sites confirms compound heterozygotes possess normal frequencies of CD127lo FoxP3+ cells. (D) Deficiency in IL2RA surface expression in compound heterozygote 3 led to aberrant downstream signalling as measured by pStat5 expression after stimulation with IL-2, but not IL-7 or IL-15. (E) Due to the inability to sort CD25hi Tregs from the CD25-deficient compound heterozygotes, an alternate gating strategy was established to enrich for FoxP3+ cells from CD3+CD4+ T cells using the surface markers CD127loCD45RO+ TIGIT+. Intracellular FoxP3 staining from the indicated gated population is shown. (F) While these CD3+CD4+CD127loCD45RO+ TIGIT+ potential "Tregs" were highly enriched for FoxP3 and showed some suppressive capacity when cultured with CFSE-labeled stimulated responder T cells (Tresps) from healthy donors, CD3+CD4+CD127loCD45RO+TIGIT+ from the compound heterozygotes showed no suppressive ability. Stimulated Tresp population (Solid curves), non-stimulated Tresp (Dashed curve). (G) Correction of either CD25 mutation in the compound heterozygotes individually would still leave the other mutation, leaving the cells as single heterozygotes. To confirm that such a potential correction would result in some level of functional suppression, CD4+ CD25hiCD127lo Tregs from the c.530 and c.800 single heterozygote family members were isolated and their suppressive ability was assayed as in (F). (H) Dot plot summaries of Treg suppressive ability in cells from healthy donor, CD25-deficient compound heterozygotes (F) and CD25+/− c.530 or c.800 heterozygotes (G). While CD3+CD4+ CD127loCD45RO+TIGIT+"Tregs" from compound heterozygotes showed no suppressive ability, conventional CD4+CD25hiCD127lo Tregs from the single heterozygote family members showed some suppressive capacity, consistent with their lack of pronounced clinical phenotype compared to the compound hets.

FIGS. 30A-E show monogenic autoimmune mutation corrected by non-viral gene targeting in primary human T cells. (A) Three siblings in a family carry two different IL2RA (encoding high-affinity IL-2 receptor, CD25) mutations (c.530A>G creating a stop codon in IL2RA exon 4; c.800delA, creating a frameshift mutation in IL2RA exon 8 which causes an almost 100 amino acid run-on). (B) These three compound heterozygote siblings show greatly reduced, but not completely absent, cell surface expression of IL2RA on their primary T cells. Non-viral gene targeting of the c.530 mutation by electroporation of a Cas9 RNP and a dsDNA HDR template containing the correct IL2RA sequence (along with a silent mutation in the targeted PAM sequence) successfully rescued IL2RA cell surface expression in a portion of T cells from each compound heterozygote sibling 2 days following electroporation. (C) 7 days after non-viral gene targeting, targeted T cells showed increased phosphorylation levels of Stat5 upon IL-2 stimulation compared to non-targeted controls. (D) 9 days following non-viral gene targeting to correct the c.530 mutation, IL2RA+ T cells from the three compound heterozygote donors include an increased level of FoxP3+ cells compared to non-targeted cells or healthy donor cells. (E) Non-viral gene targeting and correction of the c.530 mutation is possible and efficient using an optimized therapeutic reagent set (D10A nickase along with ssDNA HDR template). T cells from one compound heterozygote donor were stained for IL2RA surface expression after 9 days of ex-vivo expansion following electroporation (2 days following re-stimulation).

FIGS. 34A-B show diminished HDR potential and altered clinical phenotype in compound heterozygote IL2RA loss-of-function patient receiving immunosuppressants. (A) Flow cytometric analysis of GFP expression 6 days following electroporation of a positive HDR control RAB11A-GFP dsDNA HDR template into CD3+ T cells from the indicated patients revealed lower GFP expression in the three compound heterozygotes compared to their two c.800 heterozygote siblings. Compared to a cohort of twelve healthy donors similarly edited (FIG. 20), both c.800 heterozygotes as well as compound het 1 and 2 were within the general range observed across healthy donors, whereas compound het 3 had lower GFP expression than any healthy donor analyzed. Of note, while in compound het 3 HDR mediated correction at the c.530 mutation was substantially lower than the other two compound hets (FIG. 31A), CD25 surface expression after electroporation of the c.800delA targeting RNP alone was similar. Unlike HDR mediated repair, a NHEJ mediated frameshift correction at c.800delA may not require cell proliferation, consistent with compound het 3 being the only compound heterozygote patient on active immunosuppressants at the time of blood draw and T cell isolation. (B) Altered cell-state associated with the patient's disease could also be contributory to diminished HDR rates. TIGIT and CTLA4 expression levels in non-edited, isolated CD4+ T cells from each indicated patient measured by flow cytometry. Consistent with altered activation state, cells from compound het 3 had a distinct phenotype, with increased TIGIT and CTLA4 expression compared both to healthy donors, the heterozygous family members, as well the other two compound heterozygous siblings.

DEFINITIONS

Figure 1:
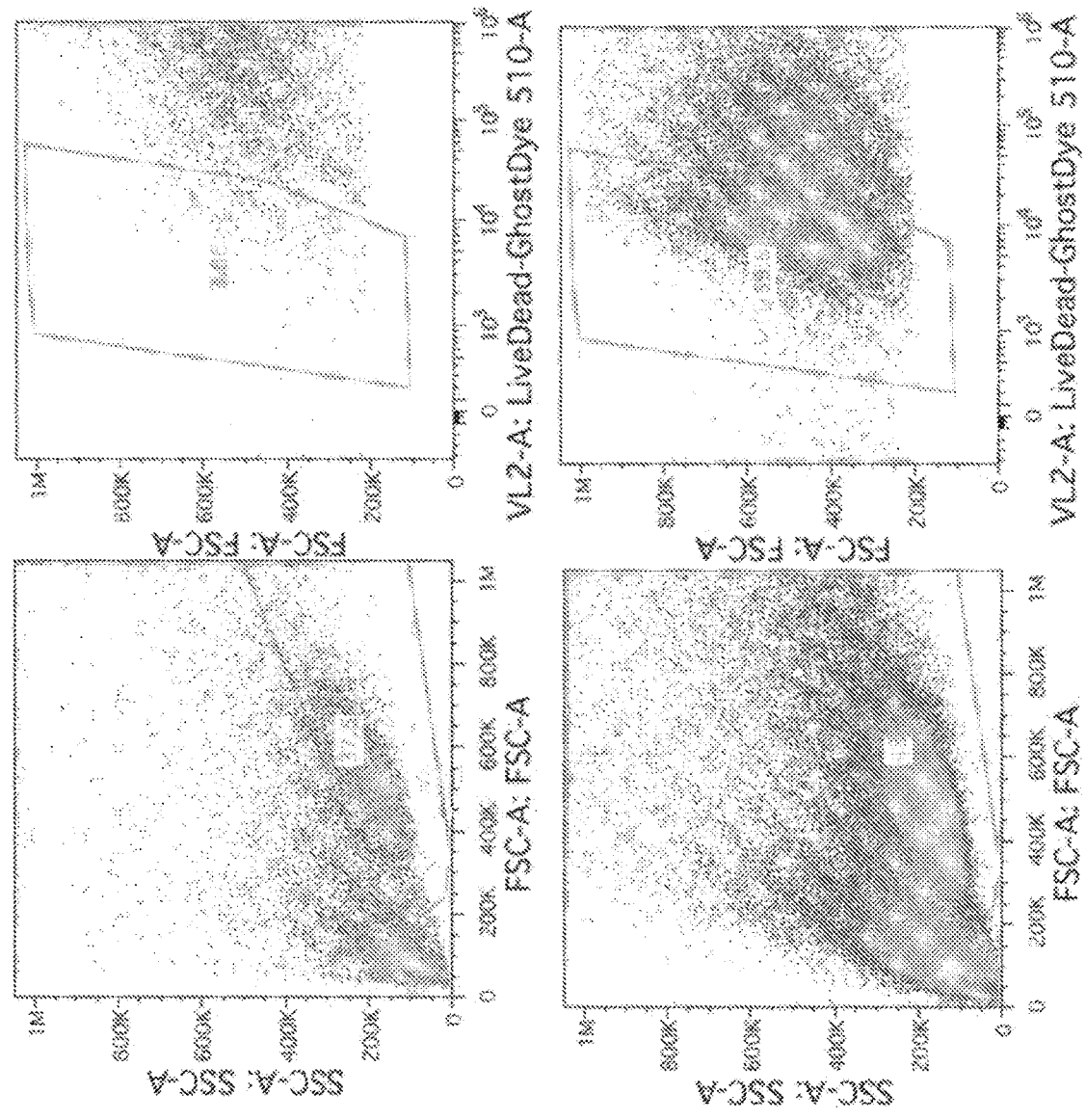
FIG. 1 shows low cell viability after electroporation of high concentrations of naked DNA necessary to achieve a workable editing efficiency in a cell.

As used in this specification and the appended claims, the singular forms "a," "an," and "the" include plural reference unless the context clearly dictates otherwise.

The term "nucleic acid" or "nucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with gene, cDNA, and mRNA encoded by a gene.

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, guide RNA (e.g., a small guide RNA), or micro RNA "Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative or palliative treatment.

A "promoter" is defined as one or more a nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, the term "complementary" or "complementarity" refers to specific base pairing between nucleotides or nucleic acids. Complementary nucleotides are, generally, A and T (or A and U), and G and C.

As used throughout, by subject is meant an individual. For example, the subject is a mammal, such as a primate, and, more specifically, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical uses and formulations are contemplated herein. The term does not denote a particular age or sex. Thus, adult and newborn subjects, whether male or female, are intended to be covered. As used herein, patient or subject may be used interchangeably and can refer to a subject afflicted with a disease or disorder.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-mediated nuclease, Cas9 in complex with guide and activating RNA to recognize and cleave foreign nucleic acid. Guide RNAs having the activity of both a guide RNA and an activating RNA are also known in the art. In some cases, such dual activity guide RNAs are referred to as a small guide RNA (sgRNA).

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. The Cas9 nuclease domain can be optimized for efficient activity or enhanced stability in the host cell.

As used herein, the term "Cas9" refers to an RNA-mediated nuclease (e.g., of bacterial or archeal orgin, or derived therefrom). Exemplary RNA-mediated nuclases include the foregoing Cas9 proteins and homologs thereof, and include but are not limited to, CPF1 (See, e.g., Zetsche et al., Cell, Volume 163, Issue 3, p 759-771, 22 Oct. 2015). Similarly, as used herein, the term "Cas9 ribonucleoprotein" complex and the like refers to a complex between the Cas9 protein, and a crRNA (e.g., guide RNA or small guide RNA), the Cas9 protein and a trans-activating crRNA (tracrRNA), the Cas9 protein and a small guide RNA, or a combination thereof (e.g., a complex containing the Cas9 protein, a tracrRNA, and a crRNA guide RNA).

As used herein, the phrase "editing" in the context of editing of a genome of a cell refers to inducing a structural change in the sequence of the genome at a target genomic region. For example, the editing can take the form of inserting a nucleotide sequence into the genome of the cell. The nucleotide sequence can encode a polypeptide or a fragment thereof. Such editing can be performed by inducing a double stranded break within a target genomic region, or a pair of single stranded nicks on opposite strands and flanking the target genomic region. Methods for inducing single or double stranded breaks at or within a target genomic region include the use of a Cas9 nuclease domain, or a derivative thereof, and a guide RNA, or pair of guide RNAs, directed to the target genomic region.

As used herein, the phrase "introducing" in the context of introducing a RNP-DNA template complex refers to the translocation of the RNP-DNA template complex from outside a cell to inside the cell. In some cases, introducing refers to translocation of the RNP-DNA template complex from outside the cell to inside the nucleus of the cell. Various methods of such translocation are contemplated, including but not limited to, electroporation, contact with nanowires or nanotubes, receptor mediated internalization, translocation via cell penetrating peptides, liposome mediated translocation, and the like.

As used herein the phrase "heterologous" refers to what is not normally found in nature. The term "heterologous sequence" refers to a sequence not normally found in a given cell in nature. As such, a heterologous nucleotide or protein sequence may be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein, the phrase "primary" in the context of a primary cell or primary stem cell refers to a cell that has not been transformed or immortalized. Such primary cells can be cultured, sub-cultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized directly without culturing or sub-culturing. In some cases, the primary cells are stimulated, activated, or differentiated. For example, primary T cells can be activated by contact with (e.g., culturing in the presence of) CD3, CD28 agonists, IL-2, IFN-γ, or a combination thereof.

As used herein, the phrase "hematopoietic stem cell" refers to a type of stem cell that can give rise to a blood cell. Hematopoietic stem cells can give rise to cells of the myeloid or lymphoid lineages, or a combination thereof. Hematopoietic stem cells are predominantly found in the bone marrow, although they can be isolated from peripheral blood, or a fraction thereof. Various cell surface markers can be used to identify, sort, or purify hematopoietic stem cells. In some cases, hematopoietic stem cells are identified as c-kit$^+$ and lin$^-$. In some cases, human hematopoietic stem cells are identified as CD34$^+$, CD59$^+$, Thy1/CD90$^+$, CD38$^{lo/-}$, C-kit/CD117$^+$, lin$^-$. In some cases, human hematopoietic stem cells are identified as CD34$^-$, CD59$^+$, Thy1/CD90$^+$, CD38$^{lo/-}$, C-kit/CD117$^+$, lin$^-$. In some cases, human hematopoietic stem cells are identified as CD133$^+$, CD59$^+$, Thy1/CD90$^+$, CD38$^{lo/-}$, C-kit/CD117$^+$, lin$^-$. In some cases, mouse hematopoietic stem cells are identified as CD34$^{lo/-}$, SCA-1$^+$, Thy1$^{+/lo}$, CD38$^+$, C-kit$^+$, lin$^-$. In some cases, the hematopoietic stem cells are CD150$^+$CD48$^-$CD244$^-$.

As used herein, the phrase "hematopoietic cell" refers to a cell derived from a hematopoietic stem cell. The hematopoietic cell may be obtained or provided by isolation from an organism, system, organ, or tissue (e.g., blood, or a fraction thereof). Alternatively, an hematopoietic stem cell can be isolated and the hematopoietic cell obtained or provided by differentiating the stem cell. Hematopoietic cells include cells with limited potential to differentiate into further cell types. Such hematopoietic cells include, but are not limited to, multipotent progenitor cells, lineage-restricted progenitor cells, common myeloid progenitor cells, granulocyte-macrophage progenitor cells, or megakaryocyte-erythroid progenitor cells. Hematopoietic cells include cells of the lymphoid and myeloid lineages, such as lymphocytes, erythrocytes, granulocytes, monocytes, and thrombocytes. In some embodiments, the hematopoietic cell is an immune cell, such as a T cell, B cell, macrophage, a natural killer (NK) cell or dendritic cell. In some embodiments the cell is an innate immune cell.

As used herein, the phrase "T cell" refers to a lymphoid cell that expresses a T cell receptor molecule. T cells include, but are not limited to, naïve T cells, stimulated T cells, primary T cells (e.g., uncultured), cultured T cells, immortalized T cells, helper T cells, cytotoxic T cells, memory T cells, regulatory T cells, natural killer T cells, combinations thereof, or sub-populations thereof. T cells can be CD4$^+$, CD8$^+$, or CD4$^+$ and CD8$^+$. T cells can be helper cells, for example helper cells of type $T_h1$, $T_h2$, $T_h3$, $T_h9$, $T_h17$, or $T_{FH}$. T cells can be cytotoxic T cells. Regulatory T cells can be FOXP3$^+$ or FOXP3$^-$. T cells can be alpha/Beta T cells or gamma/delta T cells. In some cases, the T cell is a CD4$^+$CD25$^{hi}$ CD127$^{lo}$ regulatory T cell. In some cases, the T cell is a regulatory T cell selected from the group consisting of Tr1, Th3, CD8+CD28−, Treg17, and Qa-1 restricted T cells, or a combination or sub-population thereof. In some cases, the T cell is a FOXP3$^+$ T cell. In some cases, the T cell is a CD4$^+$CD25$^{lo}$ CD127$^{hi}$ effector T cell. In some cases, the T cell is a CD4$^+$CD25$^{lo}$ CD127$^{hi}$ CD45RA$^{hi}$CD45RO$^-$ naïve T cell.

A T cell can be a recombinant T cell that has been genetically manipulated. In some cases, the recombinant T cell has a recombinant (e.g., mutated or heterologous) T cell receptor or a chimeric antigen receptor (CAR). For example, the T cell receptor can have one or more mutations in a complementarity determining region of a T cell receptor to alter antigen specificity. As another example, the T cell receptor can be mutated (e.g., in the endodomain) to increase or decrease signaling. As yet another example, the T cell receptor can be replaced with a heterologous T cell receptor. As yet another example, the T cell receptor can be replaced with a polypeptide having a different receptor domain, such as an antibody or antibody fragment. In some cases, the T cell receptor is a chimeric receptor containing a targeting domain (e.g., an antibody fragment), a transmembrane domain, and an intracellular or endodomain domain. The endodomain can contain one or more signaling domains and/or adaptor domains to provide robust T cell activation and anti-antigen activity.

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term homology directed repair (HDR) refers to a cellular process in which cut or nicked ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR-induced change of the sequence at the target site. In this way, specific mutations can be introduced at the cut site.

As used herein, a single-stranded DNA template or a double-stranded DNA template refers to a DNA oligonucleotide that can be used by a cell as a template for HDR. Generally, the single-stranded DNA template or a double-stranded DNA template has at least one region of homology to a target site. In some cases, the single-stranded DNA template or double-stranded DNA template has two homologous regions flanking a region that contains a heterologous sequence to be inserted at a target cut site.

DETAILED DESCRIPTION OF THE INVENTION

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Provided herein are compositions and methods for editing the genome of a cell. The inventors have surprisingly discovered that large nucleotide sequences, for example, nucleotide sequences greater than about 200 nucleotides or base pairs in length, can be inserted into the genome of a cell, in the absence of a viral vector. In some embodiments, the nucleotide sequence greater than about 200 nucleotides or base pairs in length, can be inserted into the genome of a primary immune cell, in the absence of a viral vector Integration of large nucleic acids, for example nucleic acids greater than 200 nucleotides in size, into cells, can be limited by low efficiency of integration, off-target effects and/or loss of cell viability. Described herein are methods and compositions for achieving integration of a nucleotide sequence, for example, a nucleotide sequence greater than about 200 nucleotides in size, into the genome of a cell. In some methods the efficiency of integration is increased, off-target effects are reduced and/or loss of cell viability is reduced.

Methods

Methods for editing the genome of a cell can include a) providing a Cas9 ribonucleoprotein complex (RNP)-DNA template complex comprising: (i) the RNP, wherein the RNP comprises a Cas9 nuclease domain and a guide RNA, wherein the guide RNA specifically hybridizes to a target region of the genome of the cell, and wherein the Cas9 nuclease domain cleaves the target region to create an insertion site in the genome of the cell; and (ii) a double-stranded or single-stranded DNA template, wherein the size of the DNA template is greater than about 200 nucleotides, wherein the 5' and 3' ends of the DNA template comprise nucleotide sequences that are homologous to genomic sequences flanking the insertion site, and wherein the molar ratio of RNP to DNA template in the complex is from about 3:1 to about 100:1; and b) introducing the RNP-DNA template complex into the cell.

In some embodiments, the methods described herein provide an efficiency of delivery of the RNP-DNA template complex of at least about 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the efficiency is determined with respect to cells that are viable after introducing the RNP-DNA template into the cell. In some cases, the efficiency is determined with respect to the total number of cells (viable or non-viable) in which the RNP-DNA template is introduced into the cell.

As another example, the efficiency of delivery can be determined by quantifying the number of genome edited cells in a population of cells (as compared to total cells or total viable cells obtained after the introducing step). Various methods for quantifying genome editing can be utilized. These methods include, but are not limited to, the use of a mismatch-specific nuclease, such as T7 endonuclease I; sequencing of one or more target loci (e.g., by sanger sequencing of cloned target locus amplification fragments); and high-throughput deep sequencing.

In some embodiments, loss of cell viability is reduced as compared to loss of cell viability after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages. In some embodiments, off-target effects of integration are reduced as compared to off-target integration after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages.

In some cases, the methods described herein provide for high cell viability of cells to which the RNP-DNA template has been introduced. In some cases, the viability of the cells to which the RNP-DNA template has been introduced is at least about 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the viability of the cells to which the RNP-DNA template has been introduced is from about 20% to about 99%, from about 30% to about 90%, from about 35% to about 85% or 90% or higher, from about 40% to about 85% or 90% or higher, from about 50% to about 85% or 90% or higher, from about 50% to about 85% or 90% or higher, from about 60% to about 85% or 90% or higher, or from about 70% to about 85% or 90% or higher.

In the methods provided herein, the molar ratio of RNP to DNA template can be from about 3:1 to about 100:1. For example, the molar ratio can be from about 5:1 to 10:1, from about 5:1 to about 15:1, 5:1 to about 20:1; 5:1 to about 25:1; from about 8:1 to about 12:1; from about 8:1 to about 15:1, from about 8:1 to about 20:1, or from about 8:1 to about 25:1.

In some embodiments, the DNA template is at a concentration of about 2.5 pM to about 25 pM. For example, the concentration of DNA template can be about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25 pM or any concentration in between these concentrations. In some embodiments, the size or length of the DNA template is greater than about 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 1 kb, 1.1 kb, 1.2 kb, 1.3 kb, 1.4 kb, 1.5 kb, 1.6 kb, 1.7 kb, 1.8 kb, 1.9 kb, 2.0 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb, 5.0 kb or any size of DNA template in between these sizes. For example, the size of the DNA template can be about 200 bp to about 500 bp, about 200 bp to about 750 bp, about 200 bp to about 1 kb, about 200 bp to about 1.5 kb, about 200 bp to about 2.0 kb, about 200 bp to about 2.5 kb, about 200 bp to about 3.0 kb, about 200 bp to about 3.5 kb, about 200 bp to about 4.0 kb, about 200 bp to about 4.5 kb, about 200 bp to about 5.0 kb. In some embodiments, the amount of DNA template is about 1 µg to about 10 µg. For example, the amount of DNA template can be about 1 µg to about 2 µg, about 1 µg to about 3 µg, about 1 µg to about 4 µg, about 1 µg to about 5 µg, about 1 µg to about 6 µg, about 1 µg to about 7 µg, about 1 µg to about 8 µg, about 1 µg to about 9 µg, about 1 µg to about 10 µg. In some embodiments the amount of DNA template is about 2 μg to about 3 μg, about 2 μg to about 4 μg, about 2 μg to about 5 μg, about 2 μg to about 6 μg, about 2 μg to about 7 μg, about 2 μg to about 8 μg, about 2 μg to about 9 μg, or 2 μg to about 10 μg. In some embodiments the amount of DNA template is about 3 μg to about 4 μg, about 3 μg to about 5 μg, about 3 μg to about 6 μg, about 3 μg to about 7 μg, about 3 μg to about 8 μg, about 3 μg to about 9 μg, or about 3 μg to about 10 μg. In some embodiments, the amount of DNA template is about 4 μg to about 5 μg, about 4 μg to about 6 μg, about 4 μg to about 7 μg, about 4 μg to about 8 μg, about 4 μg to about 9 μg, or about 4 μg to about 10 μg. In some embodiments, the amount of DNA template is about 5 μg to about 6 μg, about 5 μg to about 7 μg, about 5 μg to about 8 μg, about 5 μg to about 9 μg, or about 5 μg to about 10 μg. In some embodiments, the amount of DNA template is about 6 μg to about 7 μg, about 6 μg to about 8 μg, about 6 μg to about 9 μg, or about 6 μg to about 10 μg. In some embodiments, the amount of DNA template is about 7 μg to about 8 μg, about 7 μg to about 9 μg, or about 7 μg to about 10 μg. In some embodiments, the amount of DNA template is about 8 μg to about 9 μg, or about 8 μg to about 10 μg. In some embodiments, the amount of DNA template is about 9 μg to about 10 μg. In some cases, the size of the DNA template is large enough and in sufficient quantity to be lethal as naked DNA. In some embodiments, the DNA template encodes a heterologous protein or a fragment thereof. In some embodiments, the DNA template includes regulatory sequences, for example, a promoter sequence and/or an enhancer sequence to regulate expression of the heterologous protein or fragment thereof after insertion into the genome of a cell.

In some cases, the DNA template is a linear DNA template. In some cases, the DNA template is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA.

In some cases, the RNP-DNA template complex is formed by incubating the RNP with the DNA template for less than about one minute to about thirty minutes, at a temperature of about 20° C. to about 25° C. For example, the RNP can be incubated with the DNA template for about 5 seconds, 10 seconds, 15 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes or 30 minutes or any amount of time in between these times, at a temperature of about 20° C., 21° C., 22° C., 23° C., 24° C., or 25° C. In another example, the RNP can be incubated with the DNA template for less than about one minute to about one minute, for less than about one minute to about 5 minutes, for less than about 1 minute to about 10 minutes, for about 5 minutes to 10 minutes, for about 5 minutes to 15 minutes, for about 10 to about 15 minutes, for about 10 minutes to about 20 minutes, or for about 10 minutes to about 30 minutes, at a temperature of about 20° C. to about 25° C. In some embodiments, the RNP-DNA template complex and the cell are mixed prior to introducing the RNP-DNA template complex into the cell.

In some embodiments introducing the RNP-DNA template complex comprises electroporation. Methods, compositions, and devices for electroporating cells to introduce a RNP-DNA template complex can include those described in the examples herein. Additional or alternative methods, compositions, and devices for electroporating cells to introduce a RNP-DNA template complex can include those described in WO/2006/001614 or Kim, J. A. et al. Biosens. Bioelectron. 23, 1353-1360 (2008). Additional or alternative methods, compositions, and devices for electroporating cells to introduce a RNP-DNA template complex can include those described in U.S. Patent Appl. Pub. Nos. 2006/0094095; 2005/0064596; or 2006/0087522. Additional or alternative methods, compositions, and devices for electroporating cells to introduce a RNP-DNA template complex can include those described in Li, L. H. et al. Cancer Res. Treat. 1, 341-350 (2002); U.S. Pat. Nos. 6,773,669; 7,186,559; 7,771,984; 7,991,559; 6,485,961; 7,029,916; and U.S. Patent Appl. Pub. Nos: 2014/0017213; and 2012/0088842. Additional or alternative methods, compositions, and devices for electroporating cells to introduce a RNP-DNA template complex can include those described in Geng, T. et al. J. Control Release 144, 91-100 (2010); and Wang, J., et al. Lab. Chip 10, 2057-2061 (2010).

In some embodiments, the Cas9 protein can be in an active endonuclease form, such that when bound to target nucleic acid as part of a complex with a guide RNA or part of a complex with a DNA template, a double strand break is introduced into the target nucleic acid. The double strand break can be repaired by NHEJ to introduce random mutations, or HDR to introduce specific mutations. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to any region of a genome that contains an NGG sequence. As another example, Cas9 proteins with orthogonal PAM motif requirements can be utilized to target sequences that do not have an adjacent NGG PAM sequence. Exemplary Cas9 proteins with orthogonal PAM sequence specificities include, but are not limited to, CFP|, those described in Nature Methods 10, 1116-1121 (2013), and those described in Zetsche et al., Cell, Volume 163, Issue 3, p 759-771, 22 Oct. 2015.

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation.

In some embodiments, the RNP comprises a Cas9 nuclease. In some embodiments, the RNP comprises a Cas9 nickase. In some embodiments, the RNP-DNA template complex comprises at least two structurally different RNP complexes. In some embodiments, the at least two structurally different RNP complexes contain structurally different Cas9 nuclease domains In some embodiments, the at least two structurally different RNP complexes contain structurally different guide RNAs. In some embodiments, wherein the at least two structurally different RNP complexes contain structurally different guide RNAs, each of the structurally different RNP complexes comprises a Cas9 nickase, and the structurally different guide RNAs hybridize to opposite strands of the target region.

In some cases, a plurality of RNP-DNA templates comprising structurally different ribonucleoprotein complexes is introduced into the cell. For example a Cas9 protein can be complexed with a plurality (e.g., 2, 3, 4, 5, or more, e.g., 2-10, 5-100, 20-100) of structurally different guide RNAs to target insertion of a DNA template at a plurality of structurally different target genomic regions.

In the methods and compositions provided herein, cells include, but are not limited to, eukaryotic cells, prokaryotic cells, animal cells, plant cells, fungal cells and the like. Optionally, the cell is a mammalian cell, for example, a human cell. The cell can be in vitro, ex vivo or in vivo. The cell can also be a primary cell, a germ cell, a stem cell or a precursor cell. The precursor cell can be, for example, a pluripotent stem cell, or a hematopoietic stem cell. In some embodiments, the cell is a primary hematopoietic cell or a primary hematopoietic stem cell. In some embodiments, the primary hematopoietic cell is an immune cell. In some embodiments, the immune cell is a T cell. In some embodiments, the T cell is a regulatory T cell, an effector T cell, or a naïve T cell. In some embodiments, the T cell is a $CD4^+$ T cell. In some embodiments, the T cell is a $CD8^+$ T cell. In some embodiments, the T cell is a $CD4^+CD8^+$ T cell. In some embodiments, the T cell is a $CD4^-CD8^-$ T cell. Populations of any of the cells modified by any of the methods described herein are also provided. In some embodiments, the methods further comprise expanding the population of modified cells.

In some cases, the cells are removed from a subject, modified using any of the methods described herein and administered to the patient. In other cases, any of the constructs described herein is delivered to the patient in vivo. See, for example, U.S. Pat. No. 9,737,604 and Zhang et al. "Lipid nanoparticle-mediated efficient delivery of CRISPR/Cas9 for tumor therapy," NPG Asia Materials Volume 9, page e441 (2017).

In some embodiments, the RNP– DNA template complex is introduced into about $1 \times 10^5$ to about $2 \times 10^6$ cells. For example, the RNP– DNA template complex can be introduced into about $1 \times 10^5$ to about $5 \times 10^5$ cells, about $1 \times 10^5$ to about $1 \times 10^6$, $1 \times 10^5$ to about $1.5 \times 10^6$, $1 \times 10^5$ to about $2 \times 10^6$, about $1 \times 10^6$ to about $1.5 \times 10^6$ cells or about $1 \times 10^6$ to about $2 \times 10^6$.

In some cases, the methods and compositions described herein can be used for generation, modification, use, or control of recombinant T cells, such as chimeric antigen receptor T cells (CAR T cells). Such CAR T cells can be used to treat or prevent cancer, an infectious disease, or autoimmune disease in a subject. For example, in some embodiments, one or more gene products are inserted or knocked-in to a T cell to express a heterologous protein (e.g., a chimeric antigen receptor (CAR)).

Compositions

Also provided herein is a plurality of cells, wherein the genome of at least 20%, 30%, 40%, 50%, 60%, 70%, 80%, 90%, 95%, 99% or greater of the cells comprises a targeted insertion of a heterologous DNA template, wherein the DNA template is at least about 200 bps in size. In some embodiments, the plurality of cells comprises primary hematopoietic cells or primary hematopoietic stem cells. In some embodiments, the primary hematopoietic cells are immune cells. In some embodiments, the immune cells are T cells. In some embodiments, the T cells are regulatory T cells, effector T cells, or naïve T cells. In some embodiments, the T cells are $CD8^+$ T cells. In some embodiments, the T cells are $CD4^+CD8^+$ T cells.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following examples are provided by way of illustration only and not by way of limitation. Those of skill in the art will readily recognize a variety of non-critical parameters that could be changed or modified to yield essentially the same or similar results.

Example I

The data provided in Example I were generated as outlined in the protocol below.
Clinical protocols/donor consent were established
Isolation of PBMCs was performed with SepMate using the manufacturer's protocol.
Isolation of Bulk T Cells was performed with EasySep using the manufacturer's protocol.
Freezing was performed with Bambanker medium using the manufacturer's protocol.
20 million cells per mL
Thawing
1 mL Roswell Park Memorial Institute Medium (RPMI) added on top of thawed cells, which were then combined and washed in media
Cells rested in media only overnight prior to stimulation
Primary T Cell Culture
Media
RPMI+10% FBS
XVivo15+5% FBS; or
Immunocult (Serum free)
Useful for culturing cells in a serum free environment Stimulation
  1:1 CD3/CD28 magnetic Dynabeads
    Ratios of 0.25:1 up to 2:1 can be used
    Magnetic bead removal prior to electroporation can improve efficiency
Cytokines
  Pre-electroporation
    IL-2 at 200 U/mL (essential)
    IL-7 at 5 ng/mL (non-essential)
    IL-15 at 5 ng/mL (non-essential)
  Post-Electroporation
    IL-2 at 500 U/mL (essential)
Culture Density
  Pre-electroporation
    $1 \times 10^6$ cells per mL of culture media
      Commonly 1 mL into 24 well plates, 30 mL into T75 flask, or 70 mL into T175 flask
  Post-electroporation
    Day 0—0.25 $10^6$ electroporated cells into 1 well of 96 well round bottom plate in 200 uL media
    Day 2—Wells topped up with 100 uL fresh media (with post-electroporation cytokines at 3× concentration)
    Day 4—Transferred into 500 uL media in 48 Well plates with fresh cytokines for further expansion, subsequently split every 2-3 days to keep at ~$1 \times 10^6$ cells per mL culture, each time adding fresh cytokines
RNP Production
  160 uM crRNA mixed 1:1 with 160 uM tracrRNA
    aliquoted stocks stored at −80° C.
      Lyophilized RNA resuspended in Tris-HCL (7.4 pH) with 150 mM MgCl
      crRNA and tracrRNAs purchased from either Dharmacon or IDT, tracrRNA from respective manufacturer always used with its crRNAs
    Incubated for 30 Min at 37° C.
      Produces 80 uM gRNA
    80 uM gRNA mixed 1:1 with 40 uM Cas9
      Tube mixed by tapping side until Cas9 precipitate comes into solution
    Incubated for 15 Min at 37° C.
      Produces 20 uM RNP
    RNP can be immediately used, stored briefly at 4° C. prior to use, or stored long term at −80° C. and used after thawing
Homology Directed Repair Template (HDRT) Production
  Construction
    HDRT sequences were constructed from PCR products and GeneBlocks (IDT) using Gibson Assemblies to place the final HDRT including 5' and 3' homology arms and the desired insert into a cloning vector for future propagation
  Production
    Linear dsDNA HDRT sequences were produced by high-output PCR amplification (Kapa Hotstart polymerase)
    PCR amplicons were SPRI purified and concentrated into a final volume of 4 uL H2O per 100 uL of PCR reaction input
    Concentrations of HDRTs were analyzed by nanodrop with a 1:20 dilution
    Purity was assayed by gel electrophoresis
Primary T Cell Electroporations
  Electroporation Parameters
    Cell Number—1,000,000 (as low as 200,000 or as high as 2,000,000 will work)
    Cell Volume—20 uL (this amount can vary between about 10 μl and about 20 μl)
      Cells spun for 10 minutes at 90G, aspirated, and resuspended in electroporation buffer immediately prior to electroporation
    Electroporation Buffer-P3
      Alternate buffers, including P2 and OMEM also work, but have different optimal pulse codes
      Buffer P2 yields higher viability with lower efficiencies, but similar total number of positive cells
      OMEM Buffer with optimal pulse code (E0155) yields similar viabilities and efficiencies as P3 with its optimal pulse code
    RNP Volume—about 0.5 uL (50 pmols)
      As low 1 uL (20 pmols) and as high as 5 uL (100 pmols) work
      Optimal RNP amount varies with the amount of HDRT, however, an exemplary molar ratio of approximately 10:1 RNP to HDRT works.
    HDRT Volume—about 1 uL
      Volumes can vary between about 0.5 μL and about 2 uLs.
    HDRT Total Amount—about 5 pmols
      Lower and higher amounts are both possible with varying efficiencies
    Total electroporation volume—about 24 uL
    Pulse Code-EH115
      Many other pulse codes possible, but EH115 has proven to be the most efficient
  Electroporation Protocol
    First, HDRTs were aliquoted into wells of a 96-well polypropylene V-Bottom plate corresponding to the wells of the 96-well electroporation plate
    Indicated RNP were then similarly added to the 96-well polypropylene V-Bottom plate
    HDRTs and RNPs were incubated together at RT for 5 minutes
      As little as 30 seconds shows no difference in efficacy
      It is important that HDRT and RNP are incubated together before cells are added
    Finally, cells were resuspended in electroporation buffer, and 20 uL of cells were added to each well of the 96-well polypropylene V-Bottom plate and mixed by pipetting up and down three times with the HDRT and RNP already in the well
    24 uL of Cell+RNP+HDRT mixture was transferred from each well into the
    corresponding well of the 96 well electroporation plate for electroporation
  Post-electroporation handling
    Immediately following electroporation, 80 uL of prewarmed media was added to each well of the electroporation plate
    Plate was incubated in a 37° C. incubator for 15 minutes
      No post-electroporation incubation was slightly less efficient. Incubations of about 15 minutes to about 60 minutes are possible without loss of efficiency.
    Cells were transferred from electroporation plate into culture plates at densities described above
      Commonly, electroporation plate was split into 4 identical, 96 well round bottom plates prefilled with media and cytokines.
Results
  It would be useful to make longer DNA constructs, for example, by using PCR to produce linear dsDNA constructs that allow for large insertion sizes (>1 kb). This can be done at high through-put, however, until the present invention, this was not possible because introduction of DNA is highly toxic and leads to massive cell death. As shown in FIG. 1, at the concentrations of naked DNA necessary to achieve a workable editing efficiency, cell viability is so low that the method is non-workable.

Complexing Long DNA Templates with RNPs Rescues Cell Viability

Figure 2:
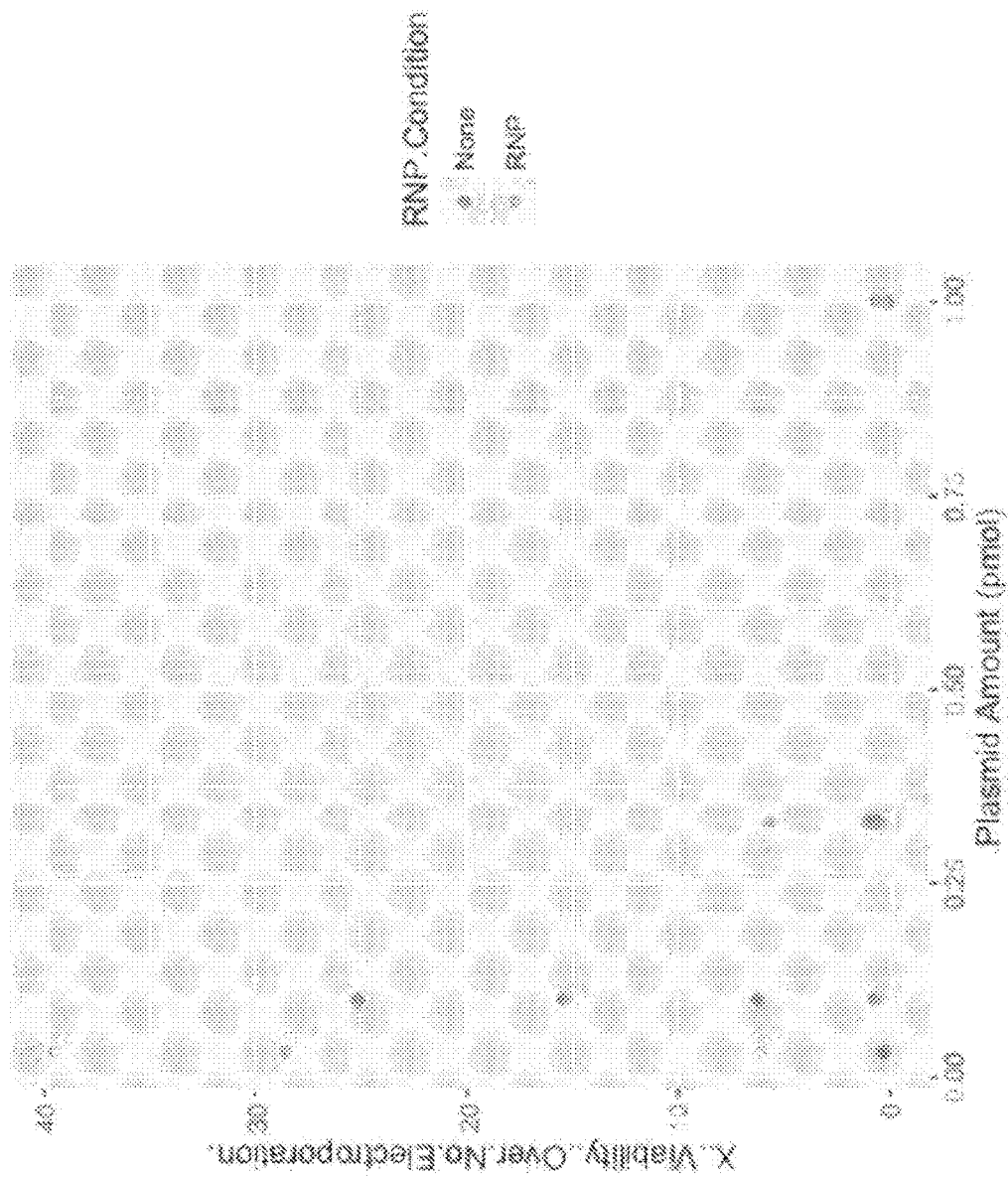
FIG. 2 shows that complexing the DNA template (plasmid) with the RNP, by a brief room temperature incubation prior to addition of cells when electroporating, reduces the viability loss normally seen upon electroporation of an amount of long, plasmid dsDNA.
Figure 3:
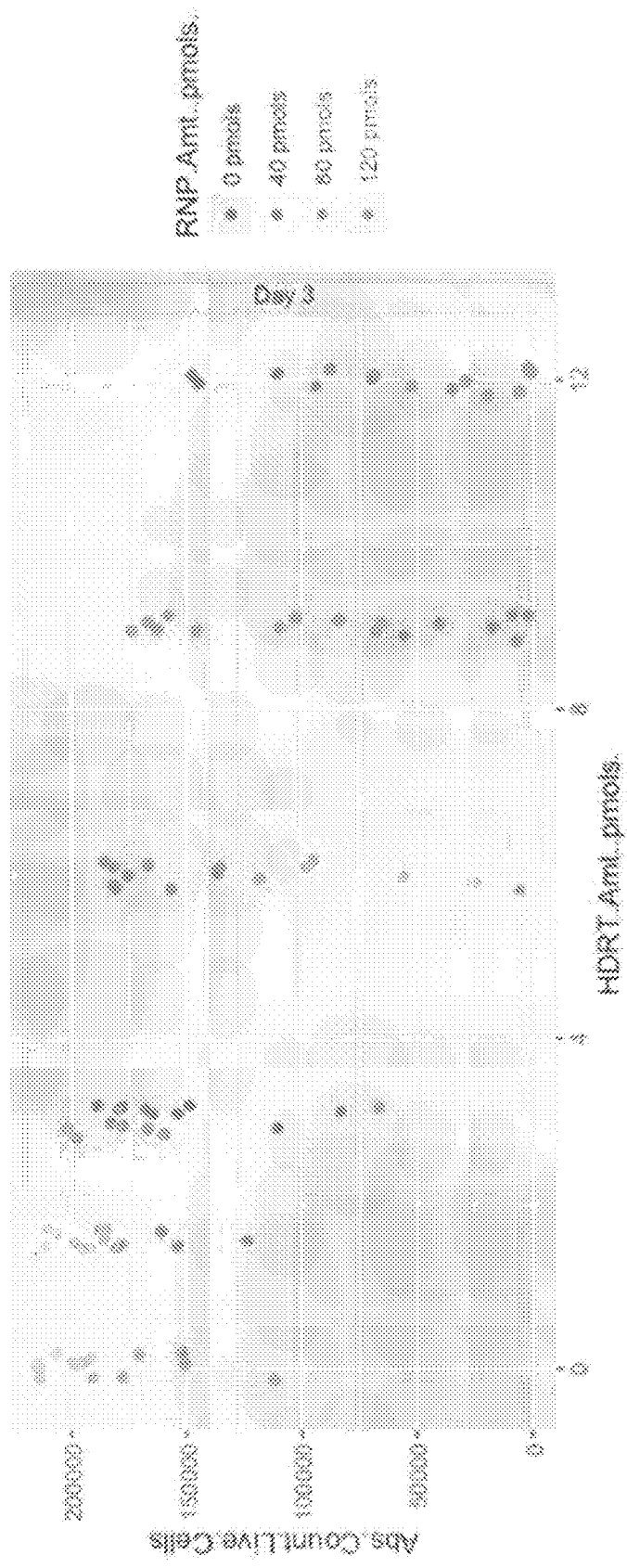
FIG. 3 shows that complexing the DNA template (linear, double-stranded DNA (dsDNA) template) with the RNP, by a brief room temperature incubation prior to addition of cells when electroporating, reduces the viability loss normally seen upon electroporation of long, linear, double-stranded DNA.

When electroporating an amount of long dsDNA (either plasmid or linear dsDNA) that causes large amounts of cell death, the inventors discovered that complexing the DNA with an RNP to form an RNP-DNA template complex (by a brief room temperature incubation, prior to addition of cells when electroporating) reduces viability loss. This was true for plasmid templates (FIG. 2) and linear dsDNA templates (FIG. 3). As the amount of DNA electroporated is increased, the amount of RNP was also increased to maintain viability (FIG. 3).

Ratios of Cas9 to DNA Template for Viability and Efficiency of Integration

Figure 4:
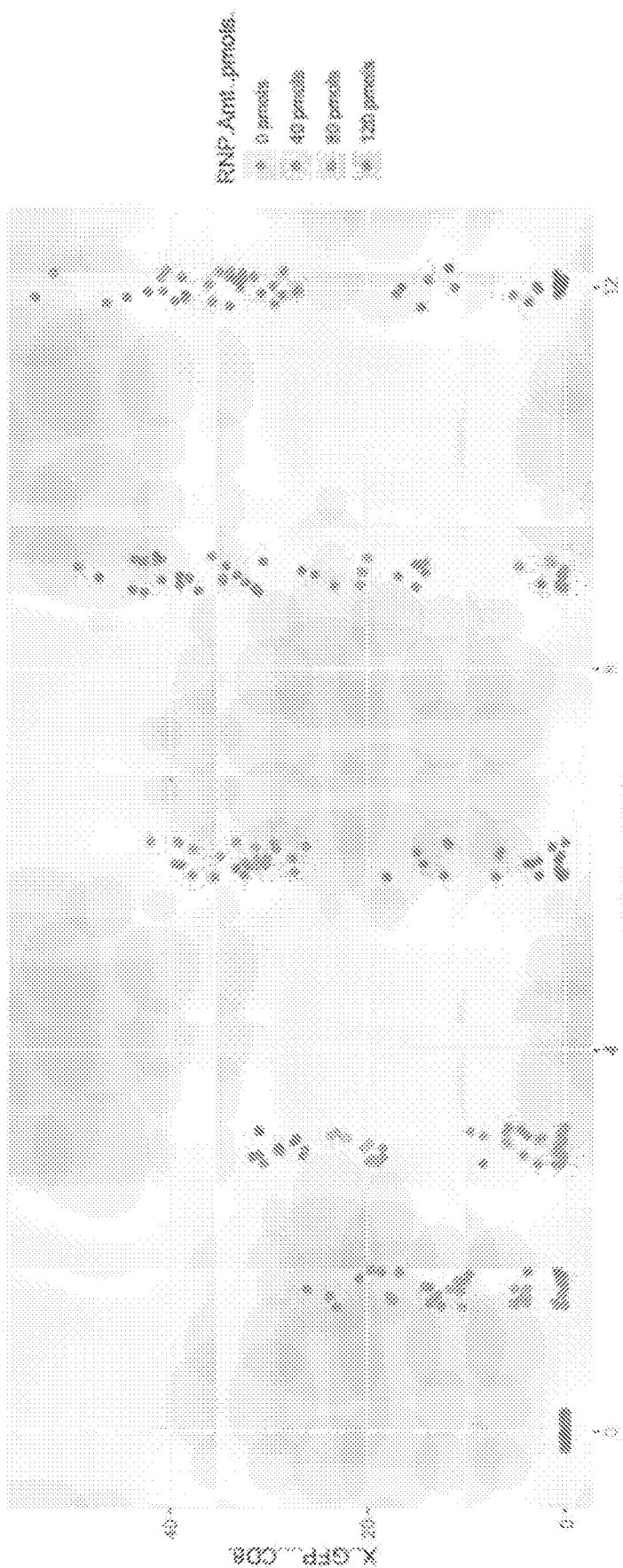
FIG. 4 shows that an exemplary molar ratio of about 10:1 RNP to DNA template maintains both efficiency of integration as well as viability, post electroporation.
Figure 5:
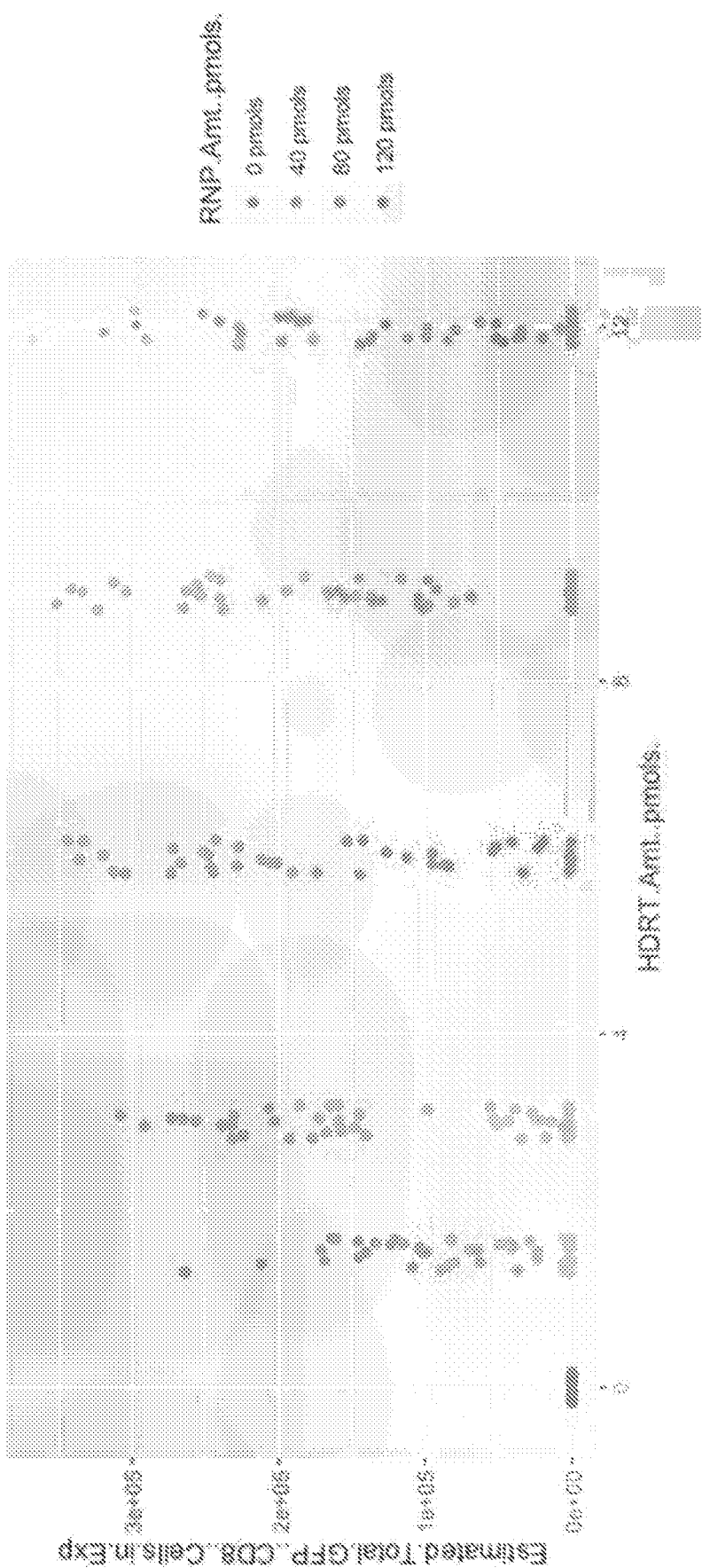
FIG. 5 shows that an exemplary molar ratio of about 10:1 RNP to DNA template balances the effects of viability loss and efficiency, and maximizes the number of integration positive cells.
Figure 6:
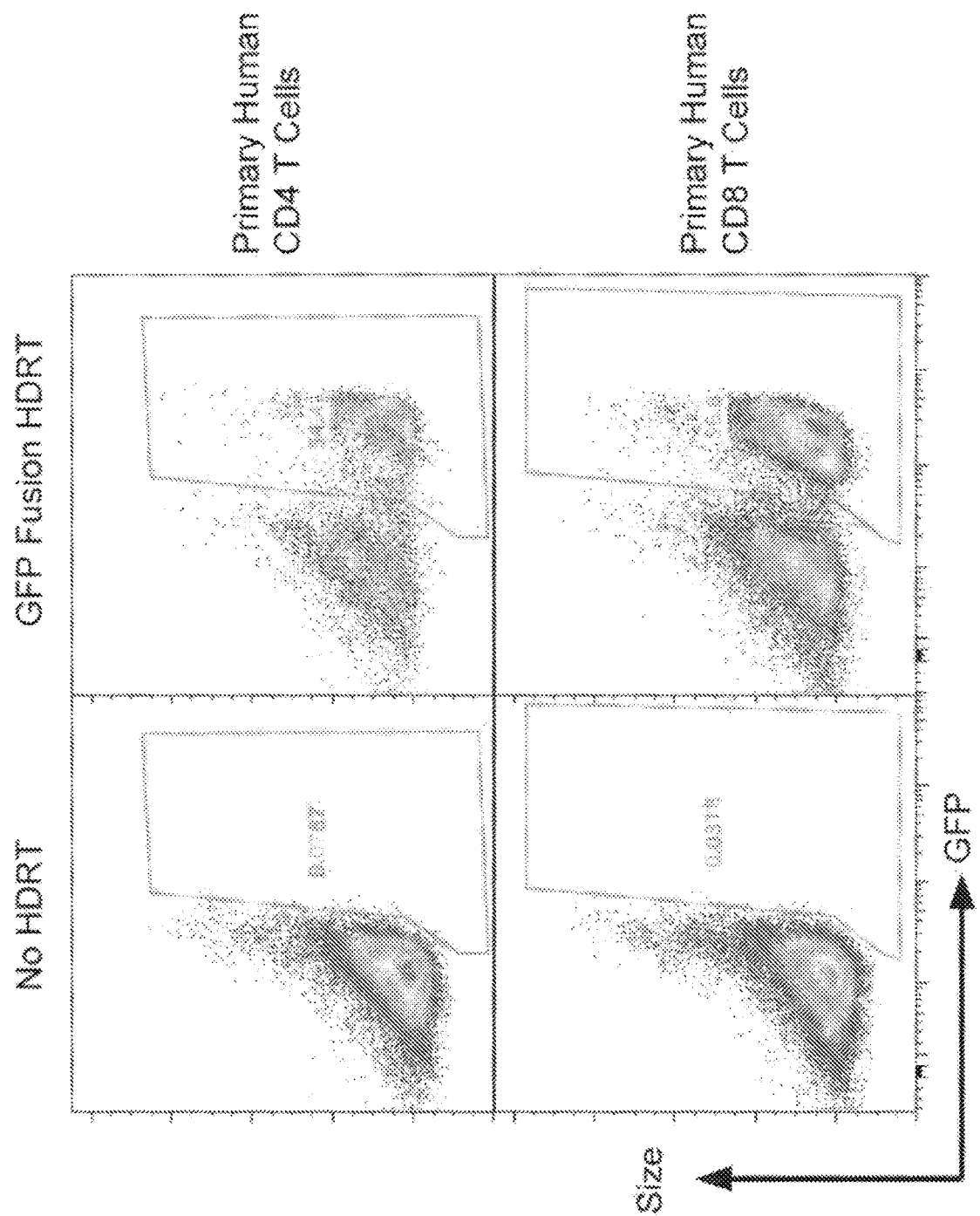
FIG. 6 shows that an exemplary molar ratio of about 10:1 RNP to DNA template allows for high efficiency insertion of large templates greater than about 750 base pairs in size.
Figure 7:
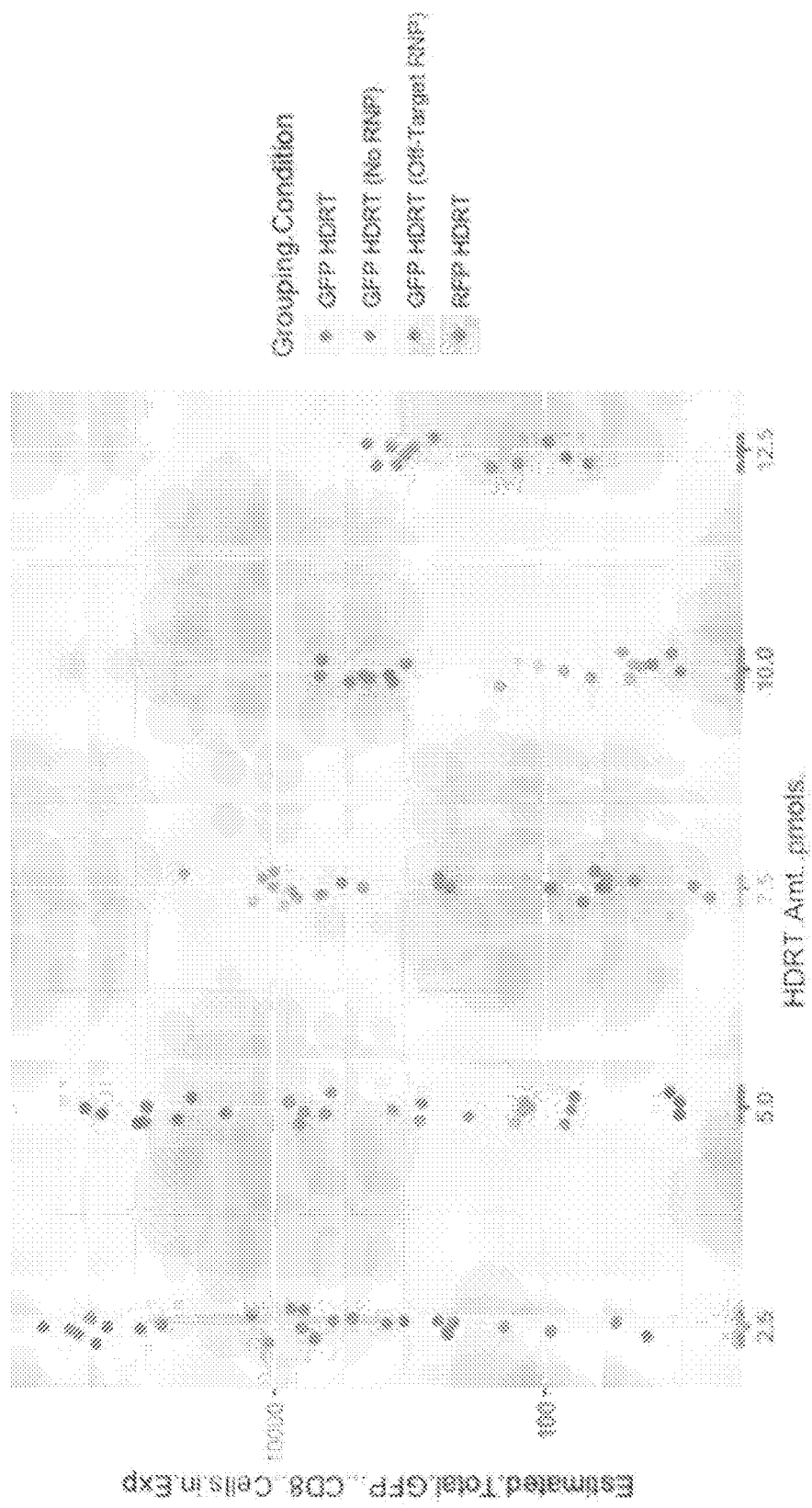
FIG. 7 shows that insertion of long DNA templates can still result in an amount of off-target integration.
Figure 8:
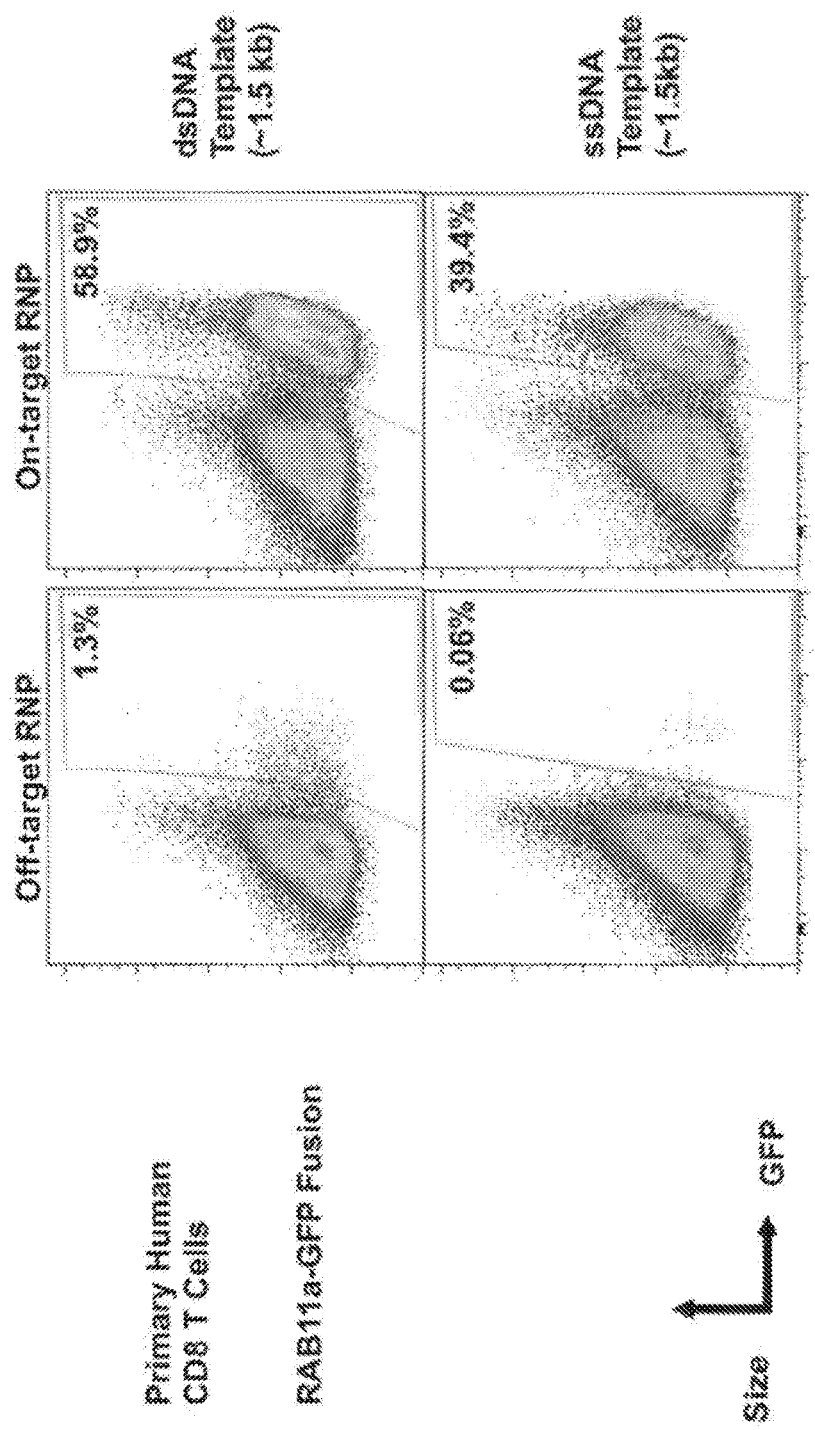
FIG. 8 shows that off-target integration can be reduced by using a long single-stranded DNA (ssDNA) template as a donor.

A molar ratio of about 10:1 RNP to DNA template maintained both efficiency of integration as well as viability, post electroporation (FIG. 4). However, ratios ranging from 3:1 to about 100:1 also worked. Using a ratio of about 10:1 RNP to DNA template balanced the effects of viability loss and efficiency, and achieved the maximal number of integration positive cells (FIG. 5). This ratio also allowed for high efficiency insertion of large templates (>750 bps) (FIG. 6).

dsDNA Templates have Some Off-Target Integrations which is Reduced Using ssDNA Templates Insertion of long DNA templates can result in a small amount of off-target integration (FIG. 7), which is similar to off-target integration seen when using an AAV as the donor template. However, some of the methods provided herein use a long ssDNA template as the donor, which results in reduced off-target integrations (FIG. 8).

Using a Cas9 Nickase Prevents Off-Target dsDNA Breaks

Figure 9:
FIG. 9 shows that the non-viral integrations disclosed herein can be inserted using two gRNAs and a Cas9 nickase (D10A), which prevents off target dsDNA breaks.

Another issue in addition to off-target integrations is off-target dsDNA breaks (which can be repaired via NHEJ as mutations) introduced by Cas9. As shown herein, the high efficiency non-viral integrations disclosed herein can be inserted using two gRNAs and a Cas9 nickase (D10A) (FIG. 9), which prevents off target dsDNA breaks.

Example II

Isolation of Human Primary T Cells for Gene Targeting

Primary human T cells were isolated from healthy human donors either from fresh whole blood samples, residuals from leukoreduction chambers after Trima Apheresis (Blood Centers of the Pacific), or leukapheresis products (Stem-Cell). Peripheral blood mononuclear cells (PBMCs) were isolated from whole blood samples by Ficoll centrifugation using SepMate tubes (STEMCELL, per manufacturer's instructions). T cells were isolated from PBMCs from all cell sources by magnetic negative selection using an EasySep Human T Cell Isolation Kit (STEMCELL, per manufacturer's instructions). Unless otherwise noted, isolated T cells were stimulated and used directly (fresh). When frozen cells were used, previously isolated T cells that had been frozen in Bambanker freezing medium (Bulldog Bio) per manufacturer's instructions were thawed, cultured in media without stimulation for 1 day, and then stimulated and handled as described for freshly isolated samples. Fresh healthy human blood donors were consented under protocol approved by the UCSF Committee on Human Research (CHR). Patient samples for gene editing were obtained under a protocol approved by the Yale Internal Review Board (IRB).

Primary T Cell Culture

Figure 15A:
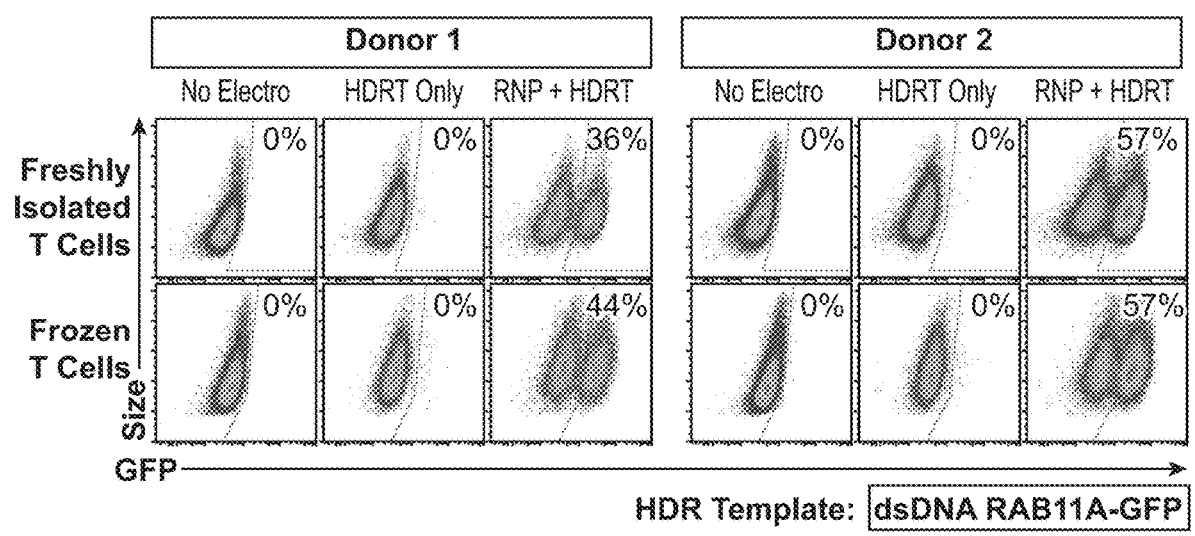
FIGS. 15A-B show efficient non-viral gene targeting in fresh and frozen T cells isolated from multiple sources. (A) A dsDNA RAB11A-GFP HDR template was inserted into both fresh and frozen T cells from two healthy donors. High rates of GFP insertion were seen in both conditions, demonstrating the adaptability of non-viral gene targeting to research or clinical protocols that require freezing of cells. (B) Similarly, high efficiencies of GFP targeted integration were seen in primary human CD3$^+$ T cells isolated from whole blood, a plasma apheresis residual, as well as leukapheresis.
Figure 15B:
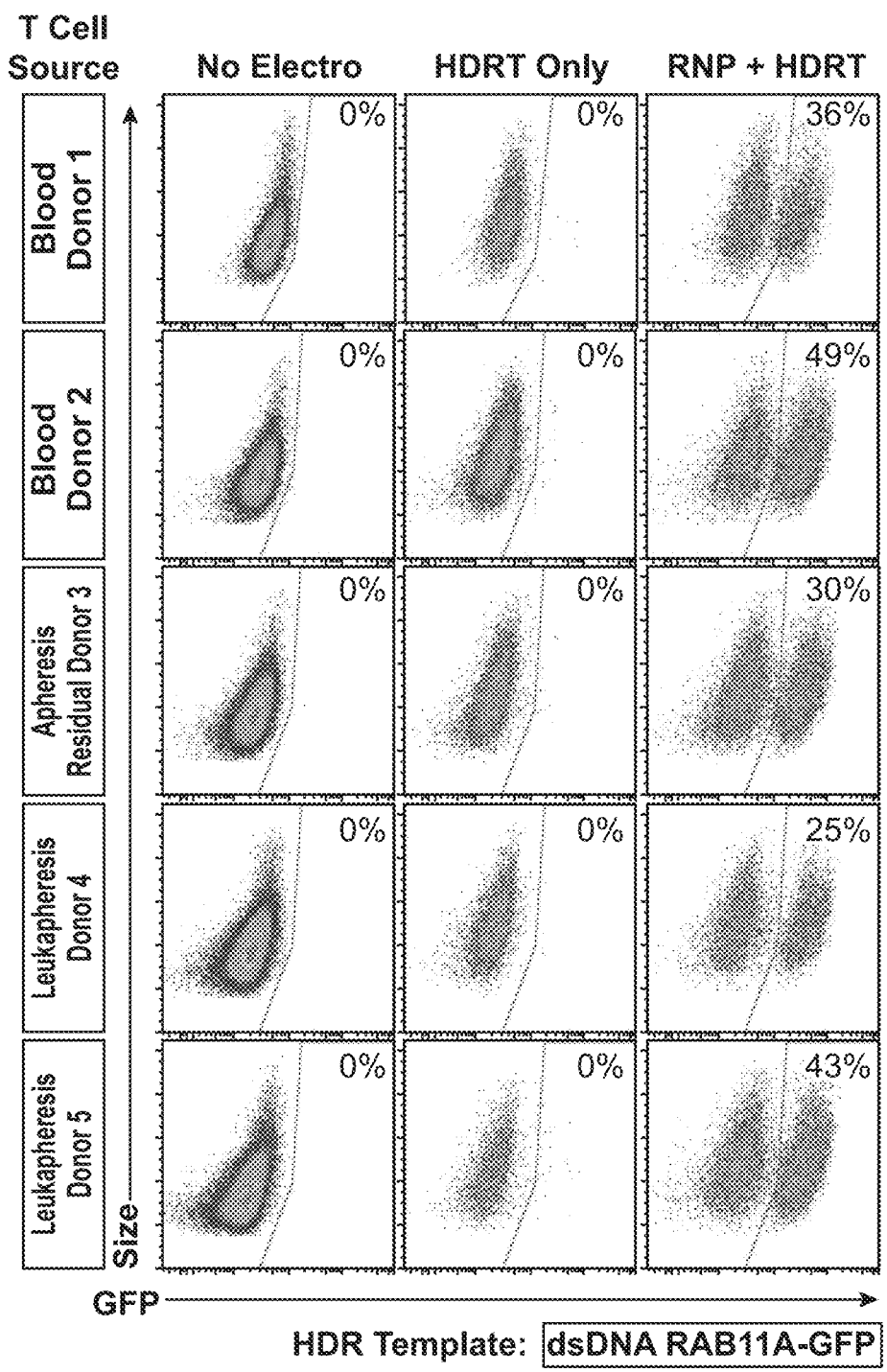

Unless otherwise noted, bulk T cells were cultured in XVivo15 medium (STEMCELL) with 5% Fetal Bovine Serum, 50 mM 2-mercaptoethanol, and 10 mM N-Acetyl L-Cystine. Serum free media (ImmunoCult XF T cell expansion media, STEMCELL) without additives, as well as RPMI+10% FBS were used in indicated experiments (FIG. 15). Immediately following isolation, T cells were stimulated for 2 days with anti-human CD3/CD28 magnetic dynabeads (ThermoFisher) at a beads to cells concentration of 1:1, along with a cytokine cocktail of IL-2 at 200 U/mL (UCSF Pharmacy), IL-7 at 5 ng/mL (ThermoFisher), and IL-15 at 5 ng/mL (Life Tech). Following electroporation, T cells were cultured in media with IL-2 at 500 U/mL. Throughout culture T cells were maintained at an approximate density of 1 million cells per mL of media. Every 2-3 days post-electroporation additional media was added, along with additional fresh IL-2 to bring the final concentration to 500 U/mL, and cells were transferred to larger culture vessels as necessary to maintain a density of 1 million cells/mL.

RNP Production

RNPs were produced by annealing of a two-component gRNA to Cas9, as previously described (7, 16). Briefly, crRNAs and tracrRNAs were chemically synthesized (Dharmacon, IDT), and recombinant Cas9-NLS, D10A-NLS, or dCas9-NLS were recombinantly produced and purified (QB3 Macrolab). Lyophilized RNA was resuspended in Tris-HCL (7.4 pH) with 150 mM KCl at a concentration of 160 uM, and stored in aliquots at −80° C. crRNA and tracrRNA aliquots were thawed, mixed 1:1 by volume, and incubated at 37° C. for 30 min to form an 80 uM gRNA solution. Recombinant Cas9 and variants, stored at 40 uM in 20 mM HEPES-KOH pH 7.5, 150 mM KCl, 10% glycerol, 1 mM DTT, were then mixed 1:1 by volume with the 80 uM gRNA (2:1 gRNA to Cas9 molar ratio) at 37° C. for 15 min to form an RNP at 20 uM. RNPs were generally electroporated immediately after complexing.

dsDNA HDRT Production

Double stranded DNA HDRT sequences were generated from PCR products. Novel HDR sequences were constructed using Gibson Assemblies to place the HDR template sequence, consisting of the homology arms (commonly synthesized as gBlocks from IDT) and the desired insert (such as GFP) into a cloning vector for sequence confirmation and future propagation. These plasmids were used as templates for high-output PCR amplification (Kapa Hotstart polymerase). PCR amplicons (the dsDNA HDRT) were SPRI purified (1.0×) and eluted into a final volume of 3 uL H2O per 100 uL of PCR reaction input. Concentrations of HDRTs were analyzed by nanodrop with a 1:20 dilution. The size of the amplified HDRT was confirmed by gel electrophoresis in a 1.0% agarose gel.

ssDNA HDRT Production by Exonuclease Digestion

To produce long ssDNA as HDR donors, the DNA of interest was amplified via PCR using one regular, non-modified PCR primer and a second phosphorylated PCR primer. The DNA strand that will be amplified using the phosphorylated primer, will be the strand that will be degraded using this method. This allows to either prepare a single stranded sense or single stranded antisense DNA using the respective phosphorylated PCR primer. To produce the ssDNA strand of interest, the phosphorylated strand of the PCR product was degraded via subsequent treatment with two enzymes, Strandase Mix A and Strandase Mix B, for 5 minutes (per 1 kb) at 37° C., respectively. Enzymes were deactivated by a 5 minute incubation at 80° C. Resulting ssDNA HDR templates were SPRI purified (1.0×) and eluted in H2O. A more detailed protocol for the Guide-it™ Long ssDNA Production System (Takara Bio USA, Inc. #632644) can be found at the manufacturer's website.

ssDNA HDRT Production by Reverse Synthesis ssDNA donors were synthesized by reverse transcription of an RNA intermediate followed by hydrolysis of the RNA strand in the resulting RNA:DNA hybrid product, as described in (28). Briefly, the desired HDR donor was first cloned downstream of a T7 promoter and the T7-HDR donor sequence amplified by PCR. RNA was synthesized by in vitro transcription using HiScribe T7 RNA polymerase (New England Biolabs) and reverse-transcribed using TGIRT-III (InGex). Following reverse transcription, NaOH and EDTA were added to 0.2 M and 0.1 M respectively and RNA hydrolysis carried out at 95° C. for 10 min. The reaction was quenched with HCl, the final ssDNA product purified using Ampure XP magnetic beads (Beckman Coulter) and eluted in sterile RNAse-free H2O. ssDNA quality was analyzed by capillary electrophoresis (Bioanalyzer, Agilent).

Primary T Cell Electroporations

RNPs and HDR templates were electroporated 2 days following initial T cell stimulation. T cells were harvested from their culture vessels and magnetic CD3/CD28 dynabeads were removed by placing cells on a magnet for 2 minutes. Immediately prior to electroporation, de-beaded cells were centrifuged for 10 minutes at 90 g, aspirated, and resuspended in the Lonza electroporation buffer P3 at 20 uL buffer per one million cells. For optimal editing, one million T cells were electroporated per well using a Lonza 4D 96-well electroporation system with pulse code EH115. Alternate cell concentrations from 200,000 up to 2 million cells per well showed lower efficiencies. Alternate electroporation buffers were used as indicated, but had different optimal pulse settings (EO155 for OMEM buffer). Unless otherwise indicated, 2.5 uLs of RNPs (50 pmols total) were electroporated, along with 2 uLs of HDR Template at 2 ugs/uL (4 ugs HDR Template total).

The order of cell, RNP, and HDRT addition appeared to matter (FIG. 10). For 96-well experiments, HDRTs were first aliquoted into wells of a 96-well polypropylene V-bottom plate. RNPs were then added to the HDRTs and allowed to incubate together at RT for at least 30 seconds. Finally, cells resuspended in electroporation buffer were added, briefly mixed by pipetting with the HDRT and RNP, and 24 uLs of total volume (cells+RNP+HDRT) was transferred into a 96 well electroporation cuvette plate. Immediately following electroporation, 80 uLs of pre-warmed media (without cytokines) was added to each well, and cells were allowed to rest for 15 minutes at 37° C. in a cell culture incubator while remaining in the electroporation cuvettes. After 15 minutes, cells were moved to final culture vessels.

Flow Cytometry

Flow cytometric analysis was performed on an Attune NxT Accustic Focusing Cytometer (ThermoFisher). Surface staining for CD3-APC-eFluor 780 (SK7, eBiosciences), CD4-PerCP (SK3, Tonbo), CD8-PE-Cy7 (SK1, BD), IL2RA/CD25-APC (BC96, Tonbo). Intracellular phosphorylation staining was performed using pStat5(Y694)-PacBlue (clone 47, BD). Intracellular cytokine staining for FoxP3 was performed using FoxP3-AF488 (206D, Biolegend).

Confocal Microscopy

Samples were prepared by drop casting 10 µl of suspended live T cells solution onto a 3×1" microscope slide onto which a 25 mm2 coverslip was placed. Imaging was performed on an upright configuration Nikon A1r laser scanning confocal microscope. Excitation was achieved through a 488 nm OBIS laser (Coherent). A long working distance (LWD) 60× Plan Apo 1.20 NA water immersion objective was used with additional digital zoom achieved through the NIS-Elements software. Images were acquired under "Galvano" mirror settings with 2× line averaging enabled and exported as TIFF to be analyzed in FIJI (ImageJ, NIH).

CUT&RUN

CUT&RUN was performed on epitope-tagged primary human T cells 11 days after electroporation and 4 days after re-stimulation with anti-CD3/anti-CD28 beads (untagged cells were not electroporated). Approximately 20% and 10% of electroporated cells showed GFP-BATF expression as determined by flow cytometry in donor 1 and donor 2 samples, respectively. CUT&RUN was performed as described in (18) using anti-GFP (ab290), anti-BATF (sc-100974), and rabbit anti-mouse (ab46540) antibodies. Briefly, 6 million cells (30 million cells for anti-GFP CUT&RUN in GFP-BATF-containing cells) were collected and washed. Nuclei were isolated and incubated rotating with primary antibody (GFP or BATF) for 2 hours at 4° C. BATF CUT&RUN samples were incubated an additional hour with rabbit anti-mouse antibody. Next, nuclei were incubated with proteinA-micrococcal nuclease (kindly provided by the Henikoff lab) for one hour at 4° C. Nuclei were equilibrated to OC and and MNase digestion was allowed to proceed for 30 minutes. Solubilized chromatin CUT&RUN fragments were isolated and purified. Paired-end sequencing libraries were prepared and run on Illumina Nextseq machines and sequencing data was processed as described in Skene and Henikoff, "An efficient targeted nuclease strategy for high resolution mapping of DNA binding sites," Elife 6 (2017) doi: 10.7554/eLife.21856. For peak calling and heatmap generation, reads mapping to centromeres were filtered out.

TLA Sequencing and Analysis

TLA sequencing was performed by Cergentis as previously described[16]. Similarly, data analysis of integration sites and transgene fusions was performed by Cergentis as previously described 16. TLA sequencing was performed in two healthy donors, each edited at the RAB1 IA locus with either a dsDNA or ssDNA HDR template to integrate a GFP fusion Sequencing reads showing evidence of primer dimers or primer bias (i.e. greater than 99% of observed reads came from single primer set) were removed.

In Vitro Treg Suppression Assay

CD4+ T cells were enriched using the EasySep Human CD4+ T cell enrichment kit (STEMCELL Technologies). CD3+CD4+CD127loCD45RO+ TIGIT+ Treg-enriched cells from IL2RA-deficient subjects and HD as well as CD3+CD4+CD25hiCD127lo Tregs from CD25+/− individuals were sorted by flow cytometry. CD3+CD4+CD25-CD127+ responder T cells (Tresps) were labeled with CellTrace CF SE (Invitrogen) at 5 Tregs and HD Tresps were co-cultured at a 1:1 ratio in the presence of beads loaded with anti-CD2, anti-CD3 and anti-CD28 (Treg Suppression Inspector; Miltenyi Biotec) at a 1 bead: 1 cell ratio. On days 3.5 to 4.5, co-cultures were analyzed by FACS for CFSE dilution. % inhibition is calculated using the following formula: 1−(% proliferation with Tregs/% proliferation of stimulated Tresps without Tregs).

Sorting and TSDR Analysis of Corrected Tregs

Ex-vivo expanded Tregs and T effector cells from a healthy control and a patient with IL2RA compound heterozygous mutations (D6) were thawed and stained. Live cells were sorted based on expression of CD25 and CD62L markers directly into ZymoResearch M-digestion Buffer (2x) (cat #D5021-9) supplemented with proteinase K. The lysate was incubated at 65° C. for greater than 2 hours and then frozen. Bisulfite conversion and pyrosequencing of the samples was performed by EpigenDx (assay ID ADS783-FS2) to interrogate the methylation status of 9 CpG sites intron 1 of the FOXP3 gene, spanning −2330 to −2263 from ATG.

Heterozygous/Homozygous Integration Prediction Model

An estimation of the percentage of cells with bi-allelic insertions at a single autosomal genomic locus (two potential alleles) can be made from only fluorescent phenotypes if two HDR templates integrating different fluorescent proteins into that same site are introduced into the cell (electroporated). A simple probability model requires only two assumptions.

Assumption 1: There are no off-target integrations at other sites besides the target locus that contribute to fluorescent phenotypes.

Assumption 2: Integration of a specific second fluorescent protein (i.e. RFP) does not depend on which fluorescent protein was integrated at the cell's other allele (i.e. GFP or RFP integrations one the first allele are equally likely to have an RFP integration at the second).

Figure 26A:
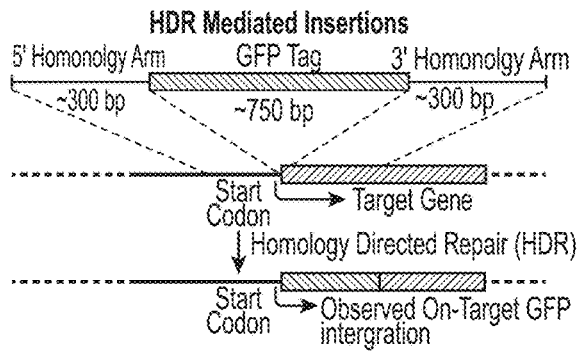
FIGS. 26A-D show fluorescent estimation and quantification of off-target integration events across multiple HDR templates. (A) Diagram of HDR mediated insertions at the N-terminus of a target locus (not drawn to scale). The homology arms specify the exact sequence where the insert (a GFP tag in this case) will be inserted, allowing for scarless integration of exogenous sequences. As a GFP fusion protein is created, GFP fluorescence will be seen as a result of this on-target integration, dependent on an RNP cutting adjacent to the integration site. (B) Double stranded DNA can be integrated via homology-independent repair mechanisms at off-target sites through either random integration at naturally occurring dsDNA breaks, or potentially at induced double stranded breaks, such as those at the off-target cut sites of the RNP. This effect can be harnessed to allow for targeted integration of a dsDNA sequence at a desired induced dsDNA break (HITI) in senescent cell types lacking the ability to do HDR, but crucially the entirety of the dsDNA template is integrated, including any potential homology arms. In the case that the homology arms contain a promoter sequence (such as for N-terminal fusion tags), these off target integrations can drive observable expression of the inserted sequence without the desired correct HDR insertion. (C) Bars represent real GFP+ percentages from human CD3+ T cells electorporated with the indicated components. Flow cytometry for fluorescent protein expression can be used to rapidly evaluate functional off-target integrations. The increase in the percentage of fluorescent cells over the limit of detection when the template alone is electroporated likely represents random integrations at naturally occurring dsDNA breaks. Not every off-target integration will yield fluorescent protein expression, but the relative differences in functional off-target expression between different templates can be assayed. Inclusion of an RNP targeting CXCR4 dramatically increases the observed off-target homology-independent integrations, likely through a HITI-type insertion event. The largest increase (from 1% to >30% in this donor) comes though through electroporation of the correct RNP and HDR mediated insertion. (D) Comparisons of on-target GFP expression (right column) vs functional off-target integrations (middle column) across five templates. Mean expression (bars) of two biologic donors (dots) are graphed.
Figure 26B:
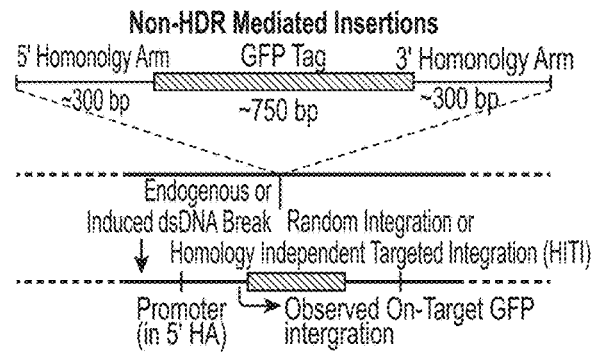
Figure 26C:
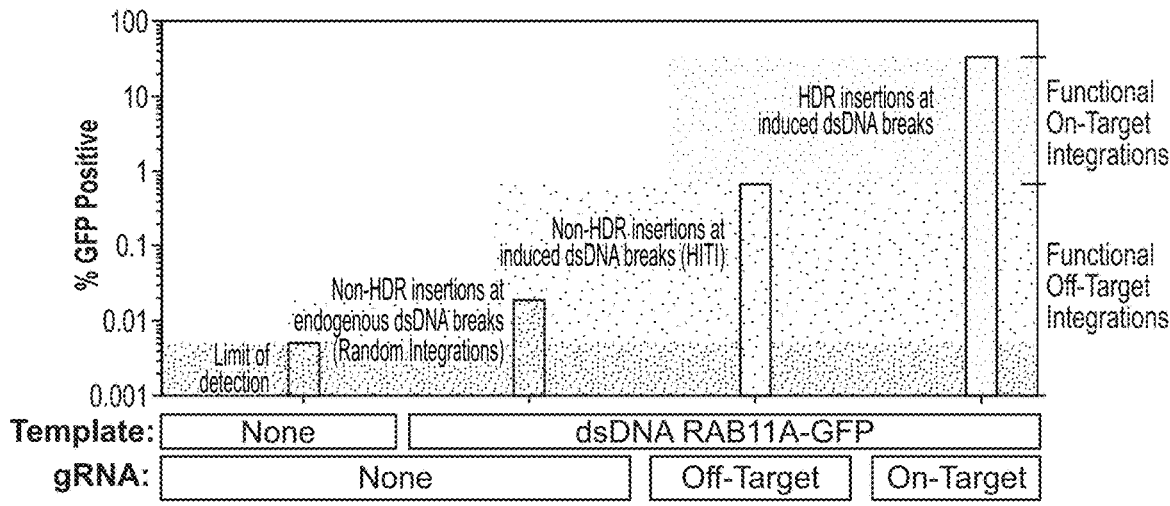
Figure 26D:
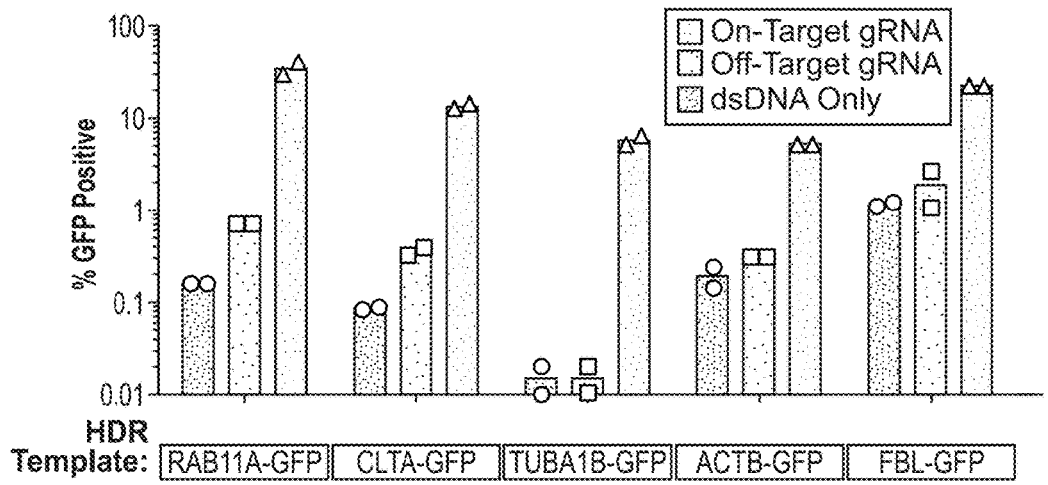

Following the labeling in FIG. 26A-C, the percentages of four different phenotypic populations are known:
% $GFP^-RFP^-$
% $GFP^+RFP^-$
% $GFP^-RFP^+$
% $GFP^+RFP^+$ From these, immediately two genotypes are known:
1) Genotype A=NA/NA=% $GFP^-RFP^-$
2) Genotype E=GFP/RFP=% $GFP^+RFP^+$ The four remaining genotypes sum to the two remaining single fluor positive phenotypes:

3) Genotype $B$+Genotype $D$=GFP/NA+GFP/GFP=% $GFP^+RFP^-$

4) Genotype $C$+Genotype $F$=RFP/NA+RFP/RFP=% $GFP^-RFP^+$

The probabilities that a RFP+ cell will also be GFP+, and vice versa, are also known from the phenotypes:

5) Probability of being $GFP^+$ given being $RFP^+$=$P$(GFP|RFP)=(% $GFP^+RFP^+$)/(% $RFP^+$+% $GFP^+RFP^+$)

6) Probability of being $RFP^+$ given being GFP+=$P$(RFP|GFP)=(% $GFP^+RFP^+$)/(% $GFP^+$+% $GFP^+RFP^+$)

Following from assumption 2, if the probability that a cell receives a GFP integration at its second allele is independent of whether the first integration was a GFP or RFP, then a relationship between the single positive genotypes can be determined (FIG. 26):

7) $D$=$P$(GFP|RFP)*$B$

8) $F$=$P$(RFP|GFP)*$C$

Inserting the equations 7 and 8 into equations 3 and 4 respectively and simplifying solves for the remaining genotypes in terms of the known phenotypes:

9) $B$=% $GFP^+RFP^-$/(1+ (% $GFP^+RFP^+$)/(% $RFP^+$+% $GFP^+RFP^+$))

10) $C$=% $GFP^-RFP^+$/(1+(% $GFP^+RFP^+$)/(% $GFP^+$+% $GFP^+RFP^+$))

11) $D$=% $GFP^+RFP^-$−$B$

12) $F$=% $GFP^-RFP^+$−$C$

From the known genotypes, the observed % of cells that are have mono-allelic or bi-allelic insertions, as well as other statistics, can be calculated readily:
Observed % Cells Heterozygous=B+C
Observed % Cells Homozygous=D+E+F
Observed % Cells with at least 1 insertion=B+C+D+E+F=1−A=1−% GFP−RFP−
Observed % Alleles that have a GFP=(B+E+2D)/2
Observed % Alleles that have a RNP=(C+E+2F)/2
Observed % Alleles with an insertion=% $Alleles_{GFP}$+% Alleles An expected % of cells homozygous if the HDR alleles were distributed randomly (in essence at Hardy-Weinberg Equilibrium) can be calculated from the observed % of cells with at least one insertion (HDR):
p=HDR allele (GFP or RFP)
q=non-HDR allele (NA)
X=% of cells observed to have at least one HDR 13) $p+q=1$ 14) $p^2+2*p*q+q^2=1$ As any cell that has an HDR (GFP or RFP) allele will show the phenotype (in this case GFP+ or RFP+):

15) $X=p^2+2*p*q$

Substituting X into equation 14 and simplifying:

16) $q=(1-X)^{1/2}$

17) $p=1-q$

18) $p=1-(1-X)^{1/2}$ $p^2$ will give then give the expected % of cells homozygous for HDR integration if HDR template insertion was random among the target alleles:

19) $p^2=2-2(1-X)^{1/2}-X$

As X is known, the expected % of homozygous cells can be calculated directly from the observed total % of cells with at least one HDR, and can then be compared the observed % of homozygous cells calculated by taking into account the information provided by integration of two separate fluorophores.

Clinical History of Family with Autoimmunity/Immune Dysregulation

The proband is a Caucasian infant who presented at 15 weeks of age after vomiting, fussiness and tachypnea led to medical evaluation that revealed severe diabetic ketoacidosis and serum glucose level of 920 mg/dL. A week after diagnosis, testing for GAD65, IA-2 and insulin autoantibodies was negative; however, autoimmune diabetes was confirmed when repeat antibody tests at 5-7 months of age in three different laboratories showed positive results for IA-2 and insulin autoantibodies, as well as very high levels of GAD65 antibodies in two of the laboratories [42.8 nmol/L (<0.02) at Mayo Laboratories and 896 IU/mL (0.0-5.0) at Barbara Davis Center]. Testing for thyroid dysfunction and celiac disease has been negative but mildly low IgA levels suggest partial IgA deficiency. C-peptide testing was repeatedly completely undetectable, including at 7 months of age when measured 90 minutes after a feed with a serum glucose level of 202 mg/dL, at which time proinsulin was also undetectable. After the initial DKA was treated with intravenous insulin, he was discharged on multiple daily injections of subcutaneous insulin (glargine and lispro) initially and later transitioned to an insulin pump with continuous glucose monitoring. He consistently required a high replacement dose of insulin in the range of 0.8-0.9 units/kg/day (48% basal at 7 months of age). He had been delivered by repeat c-section at 37 weeks gestation with a birth weight of 3.629 kg (75th percentile) without any complications and there have been no concerns about his developmental progress and his medical history has otherwise been unremarkable. His parents have disparate Caucasian ancestry and denied consanguinity.

Clinical information on family members is provided in Table 1. More detailed information is as follows:
1. Mother (37):
   a. Pneumonia as a child—explained as viral
   b. Ear infections as a child treated with antibiotics
   c. Tooth problems (perhaps related to antibiotics)
   d. Her father developed insulin dependent diabetes in his 30's. He had a low WBC and also had nummular dermatitis of the scalp.
   e. Her mother had lupus
2. Father (44)
   a. Moroccan descent
   b. No major medical problems
   c. Some possible concern this his response time to common viral infections may be prolonged.
3. Affected Child (14)
   a. Immune thrombocytopenic purpura: (+ anti-platelet antibodies)
   b. Neutropenia (anti-neutrophil Ab)
   c. Autoimmune hemolytic anemia (DAT+i.e. direct Coombs+)
   d. Nummular dermatitis of the scalp
   e. Hypercellular bone marrow: inverted CD4/CD8 ratio (0.36).
   f. Mouth ulcers
   g. Ear infections treated with tubes
   h. Diarrhea as a child
   i. 46XX— no known chromosomal abnormality
   j. Flow cytometry of peripheral blood: 82.7% of CD45+ cells are CD3+ and 5.9% are CD19+. CD19+ CD5+ cells are the deficient B cells. 43.6% of CD45+ cells are CD8+ with an inverted CD4/CD8 ratio (0.6). There is a relative increase in TCR (alpha beta)+CD3+ CD4− CD8− T lymphocytes (26% of TCR alpha beta+CD3+ cells and 5% of CD45+ leukocytes).
   k. Has been treated with immunosuppression including prednisone (20 mg), IgG-pro-IgA, Flonase nasal spray and topical steroids and Symbicort. Also treated with Neupogen.
4. Affected Child
   a. 3+ diabetes autoantibodies (anti-GAD, MIAA, ICA, negative ZnT8 and ICA512/IA-2) normal OGTT
   b. Ear infections treated with tubes at 1 yr.
   c. Eczema in the winter
5. Unaffected Daughter (15)
   a. Allergies, but otherwise healthy
6. Affected Son (4)
   a. Eczema in winter
   b. Positive test for HSV
   c. Insulin dependent diabetes within the first year of life, C-peptide<0.1 at presentation, anti-GAD ab+ (>30 (nl<1 U/ml) 1 yr after dx but negative at dx, ICA512 Ab+(1.3 (nl<1.0)) 1 yr after dx but negative at dx
7. Unaffected Daughter (9)
   a. Asthma Genetic Testing to Identify IL2RA Mutations Initial genetic testing of the proband using an in-house targeted next-generation sequencing multi-gene panel of over 40 genes known to be involved in monogenic forms of diabetes was negative. Subsequent exome sequencing in the trio pf proband and parents revealed the causative compound heterozygous mutations in the IL2RA gene. Two siblings carry only one mutation, but the other two with both mutations have evidence for autoimmunity: an older male sibling was found (at 4 or 5 years of age) to have positive diabetes autoantibodies in the absence of hyperglycemia and an older female sibling was diagnosed with autoimmune mediated pancytopenia at age 11 years. CD25 expression was markedly reduced in the three compound heterozygous children.

Clinical Phenotyping of IL2RA Patients

The CD25-deficient children have an almost complete loss of IL2-RA cell surface expression on T cells and therefore virtually no detectable CD3+CD4+CD25hiCD127lo Tregs in their blood, whereas family relatives carrying heterozygous IL2RA mutation display decreased CD25 expression on their Tregs (FIG. 34). However, frequencies of CD3+CD4+CD127loFOXP3+ T cells in CD25-deficient subjects resemble those in HD and CD25+/− individuals, thereby suggesting that Tregs may develop in the absence of IL2-Ra function (FIG. 34). Using a strategy to isolate Tregs without CD25 expression, we found that CD3+CD4+CD127loCD45RO+ TIGIT+ Treg-enriched cells from CD25-deficient subjects showed a defective ability to suppress the proliferation of responder T cells (Tresps) as compared to HD counterparts (FIG. 34). In contrast, Tregs from relatives with a single heterozygous IL2RA mutation could inhibit Tresp proliferation, although with suboptimum capacity (FIG. 34). Hence, correcting functional IL2-Ra expression on the surface of FOXP3$^+$ T cells from these patients may represent a valuable approach for developing an ex vivo gene therapy.

Results

Human T cells can be purified from blood, engineered ex vivo, and then returned to circulation through autologous transplantation. Engineered T cells are being developed to treat cancer and infectious diseases (Fesnak et al. "Engineered T cells: the promise and challenges of cancer immunotherapy," *Nat. Rev. Cancer* 16, 566-581 (2016); and Esensten et al. "Engineering Therapeutic T Cells: From Synthetic Biology to Clinical Trials," *Annu. Rev. Pathol.* 12, 305-330 (2017)).

These cell-based treatments depend on the ability to genetically reprogram T cells, for example to enhance their ability to recognize and attack specific antigens (Roybal et al. "Synthetic Immunology: Hacking Immune Cells to Expand Their Therapeutic Capabilities," *Annu. Rev. Immunol.* 35, 229-253 (2017). Cell-based therapies involving modified regulatory T cells (Tregs) designed to suppress inflammation are being developed for autoimmune diseases and organ transplantation (Bluestone et al. "Type 1 diabetes immunotherapy using polyclonal regulatory T cells," *Sci. Transl. Med.* 7, 315ra189 (2015).

A variety of approaches have been used to modify the genomes of primary human T cells. Long DNA sequences (multiple kilobases) can be inserted using lentiviral vectors, but the integration sites are non-targeted (Verhoeyen et al. in Methods in Molecular Biology (2009), pp. 97-114). Lentiviruses have been the primary means to introduce gene constructs such as chimeric antigen receptors (CARs) (Kalos et al., "T cells with chimeric antigen receptors have potent antitumor effects and can establish memory in patients with advanced leukemia" *Sci. Transl. Med.* 3, 95ra73 (2011). To knock out specific endogenous genes, sequence specific nucleases such as Cas9, TALEN or zinc-finger nuclease (ZFN) can be electroporated into T cells (Schumann et al., "Generation of knock-in primary human T cells using Cas9 ribo nucleoproteins," *Proceedings of the National Academy of Sciences.* 112, 10437-10442 (2015); and Perez et al. "Establishment of HIV-1 resistance in CD4+ T cells by genome editing using zinc-finger nucleases," *Nat. Biotechnol.* 26, 808-816 (2008)) generating double-stranded breaks that result in a non-random spectrum of insertions and deletion mutations through non-homologous end-joining (NHEJ) (van Overbeek et al., "DNA Repair Profiling Reveals Nonrandom Outcomes at Cas9-Mediated Breaks," *Mol. Cell.* 63, 633-646 (2016). Co-delivery of small (<200 bp) chemically synthesized ssDNA oligos (ssODNs) that have homology to the sequences flanking a specific nuclease cleavage site has been used to modify short DNA sequences via homology directed repair (Schumann et al. (2015)).

The targeted integration of much longer DNA sequences would enable more diverse applications. This has recently been achieved by electroporation of a sequence-specific nuclease followed by infection with an integrase-deficient adeno-associated vector (AAV) containing an HDR template (Sather et al., "Efficient modification of CCR5 in primary human hematopoietic cells using a megaTAL nuclease and AAV donor template," *Sci. Transl. Med.* 7, 307ra156 (2015); and Hubbard et al. "Targeted gene editing restores regulated CD40L function in X-linked hyper-IgM syndrome." *Blood* 127, 2513-2522 (2016)). This electroporation and infection approach has enabled novel therapeutic T cell engineering strategies (Eyquem et al., "Targeting a CAR to the TRAC locus with CRISPR/Cas9 enhances tumour rejection," *Nature* 543, 113-117 (2017)) but causes off-target integrations, necessitates a potentially undesirable viral infection, and is limited in throughput due to challenges in viral production.

Cell culture conditions, concentrations of Cas9 RNPs and HDR templates and electroporation parameters were tested to develop methods for high-efficiency non-viral genome targeting. Conditions where high concentrations of Cas9 RNPs and long DNA templates (>1 Kb) could be co-delivered into multiple loci in primary human T cells with limited effects on cell viability were identified.

Non-viral targeting could be used to correct a pathogenic mutation that causes Treg dysfunction and monogenic autoimmune disease. Described herein is a family where two children have developed early onset autoimmune disease and a third has autoantibodies suggesting a very high risk of type 1 diabetes (T1D) and identified the causal loss-of-function mutations in IL2RA through exome sequencing. IL2RA is critical for regulatory T cell function and immune homeostasis. With the non-viral CRISPR genome targeting methods provided herein, efficient mutation correction, which restored cell surface expression of IL2RA along with functional downstream signaling, was achieved. Non-viral genome targeting in primary human immune cells will enable functional studies and correction of mutations in cells from patients. Cell therapies coupled with improved gene targeting (non-viral templates, high efficiency and specific-ity, and long targeting constructs) hold enormous promise for treatment of autoimmune diseases as well as immune deficiencies, infectious diseases, organ transplantation and cancer immunotherapy.

Development of Non-Viral Human T Cell Genome Targeting

A major limitation for genome targeting in human T cells has been that DNA delivery leads to cell death (Cornu et al., "Refining strategies to translate genome editing to the clinic," *Nat. Med.* 23, 415-423 (2017)). While the introduction of short single-stranded oligodeoxynucleotide (ssODN) HDR templates did not cause significant loss of viability in T cells, larger linear dsDNA templates led to extensive toxicity (Y. Zhao et al., "High-Efficiency Transfection of Primary Human and Mouse T Lymphocytes Using RNA Electroporation," *Mol. Ther.* 13, 151-159 (2006); and Hornung et al. "Intracellular DNA recognition," I10, 123-130 (2010)).

As shown herein, long (>1 kb) linear dsDNA templates were less toxic when they were co-electroporated with a CRISPR-Cas9 ribonucleoprotein (Cas9 RNP) (FIG. 10). This suggested that co-delivery of an appropriate mixture of Cas9 RNPs and long dsDNA would enable HDR and preserve cell viability.

Figure 11F:
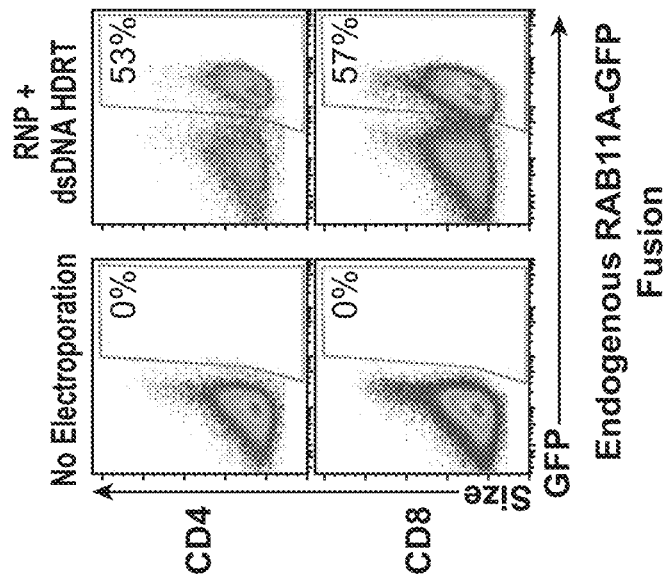
Figure 11E:
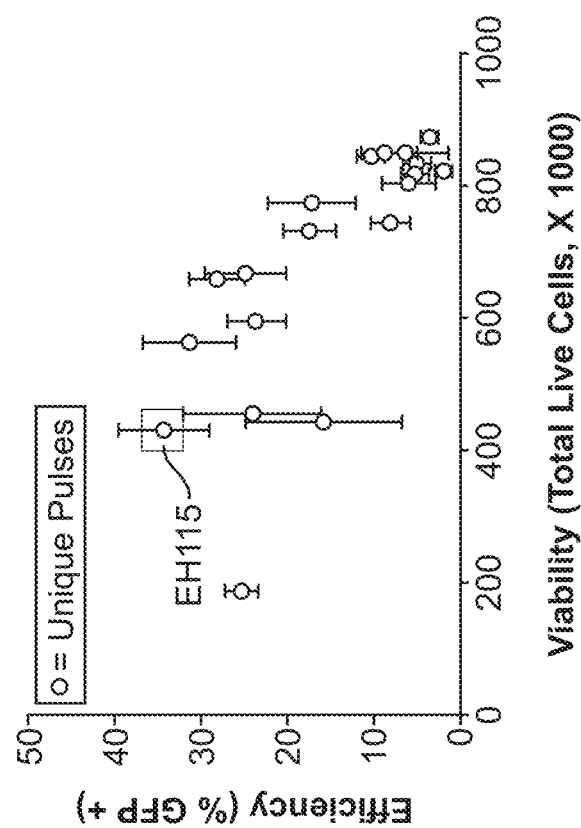
Figure 12A:
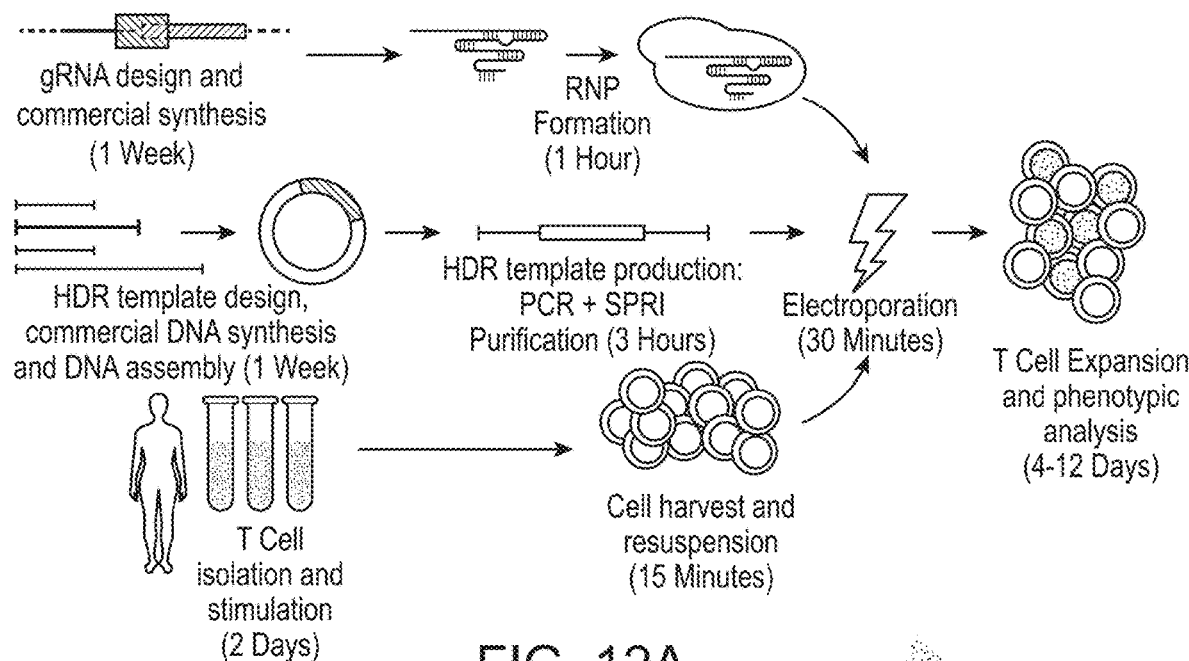
FIGS. 12A-B show non-viral gene targeting enables rapid and efficient genetic engineering in primary human T cells. (A) Diagrammatic timeline of non-viral gene targeting. Approximately one week is required to design, order from commercial suppliers, and assemble any novel combination of genomic editing reagents (gRNA along with homology directed repair template). Two days prior to electroporation, primary human T cells isolated from blood or various other sources (FIG. 15) are stimulated. dsDNA HDR templates can be made easily by PCR followed by a SPRI purification to achieve a highly concentrated product suitable for electroporation. On the day of electroporation, the gRNA complexed to an RNP, the HDR template, and harvested stimulated T cells are mixed and electroporated, a process taking approximately one and a half hours. After electroporation, engineered T cells can be readily expanded for an additional two weeks. (B) Viability is used to refer to the percentage of live cells relative to an equivalent population that went through all protocol steps except for the actual electroporation (No electroporation control). The trough in live cells after electroporation was empirically determined to come two days following, and all viability measures have been recorded at that time point unless otherwise noted. The term efficiency is used to refer to the percentage of live cells in culture expressing the "knocked in" exogenous sequence (such as GFP). Finally, the total number of cells positive for the desired integration was calculated by multiplying the efficiency by the absolute cell count. Methodological changes that maximized efficiency often were not always optimal for the total number of positive cells, and vice-versa.
Figure 12B:
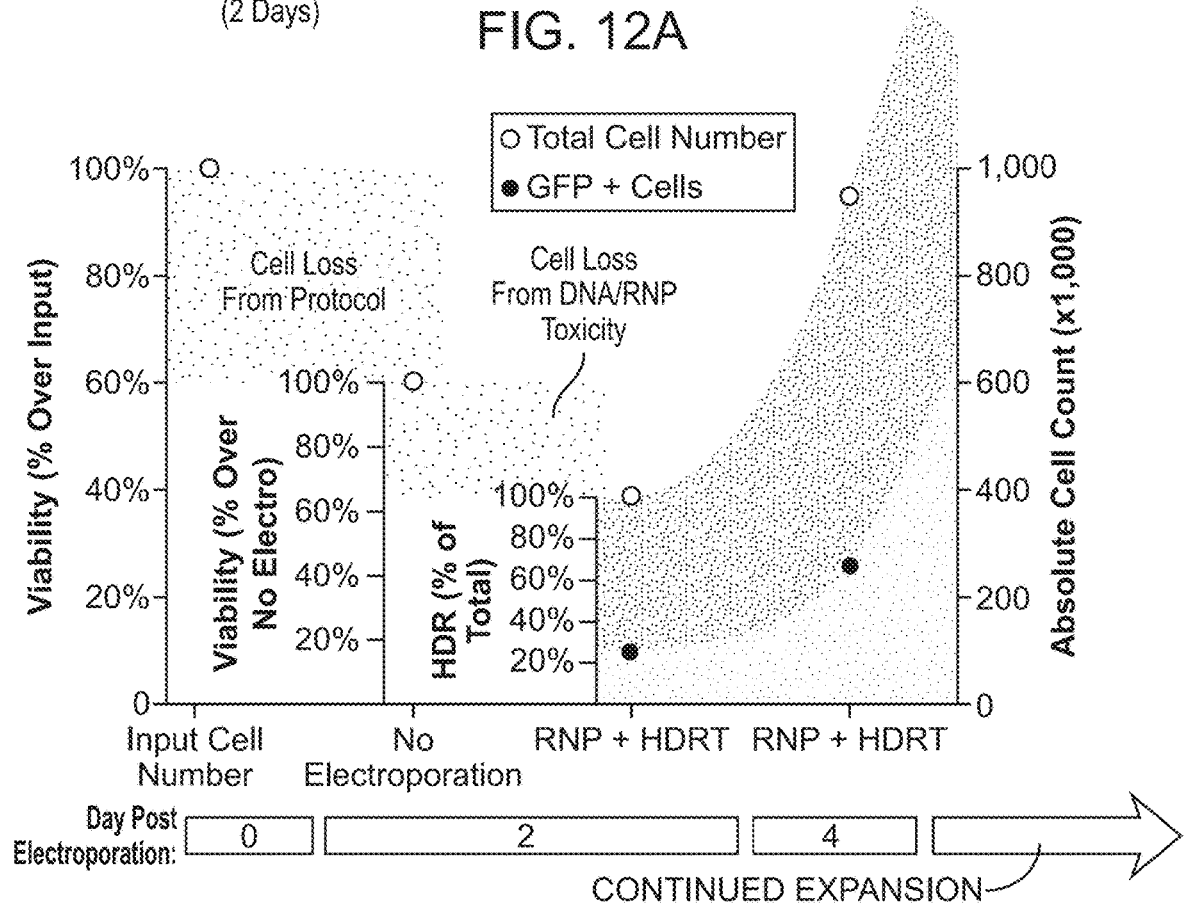
Figure 16A:
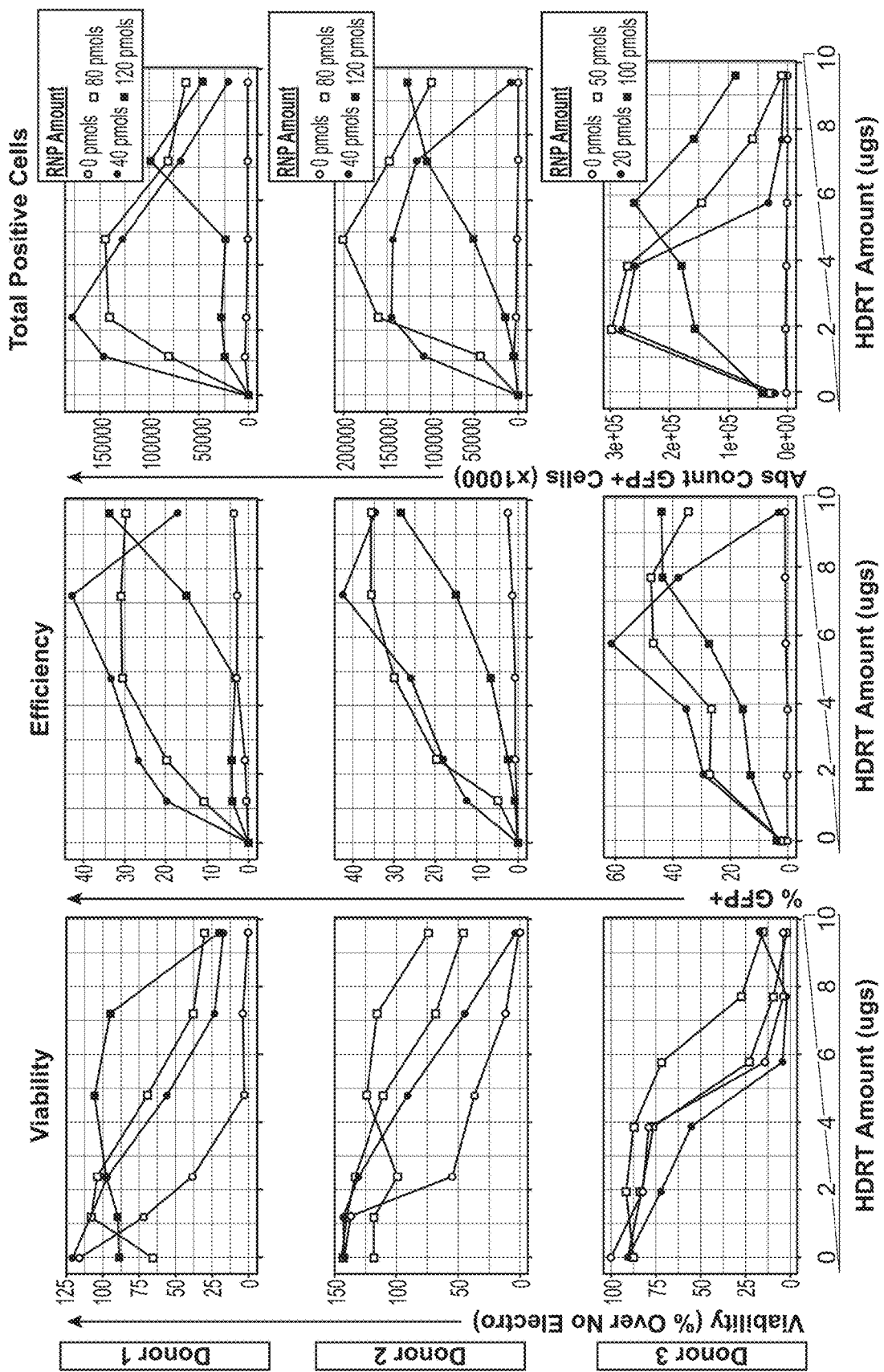
FIGS. 16A-B show optimization of RNP and HDR template formulations for non-viral gene targeting. (A) Across three donors, a consistent trend appeared that electroporation of increasing amounts of dsDNA HDR template (RAB11A-GFP) gradually reduced cell viability, while also increasing efficiency, but that intermediate concentrations tested of both HDR template and RNP gave the greatest total number of GFP+ cells. (B) Further targeted optimization series in three additional donors yielded an optimal formulation of 4 ugs of HDR template electroporated concurrently with 50 pmols of RNP. Efficiency of GFP insertion and the absolute count of total GFP+ cells was performed 4 days following electroporation. Multiple dots per graph (B) represent technical replicates.
Figure 16B:
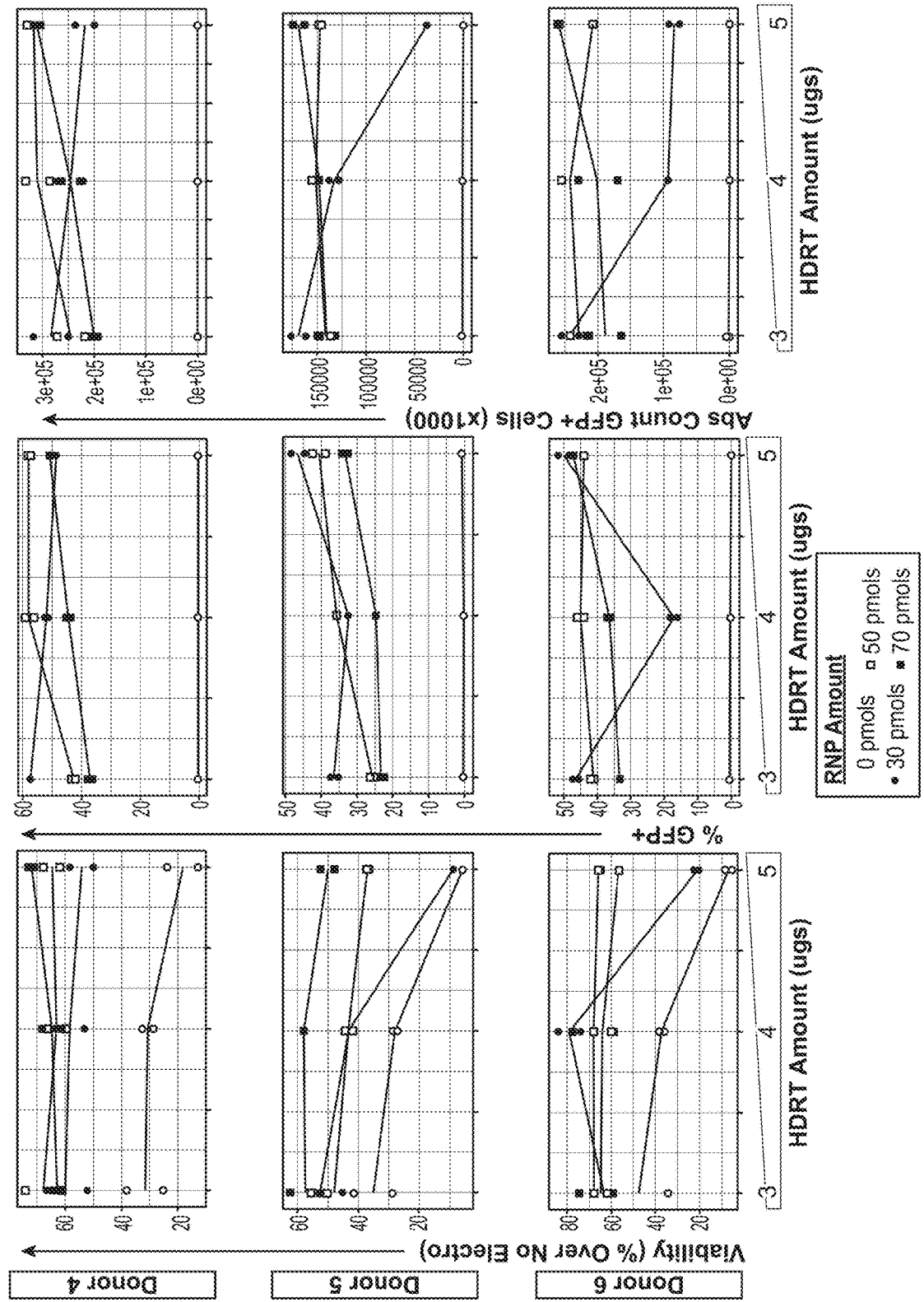
Figure 17A:
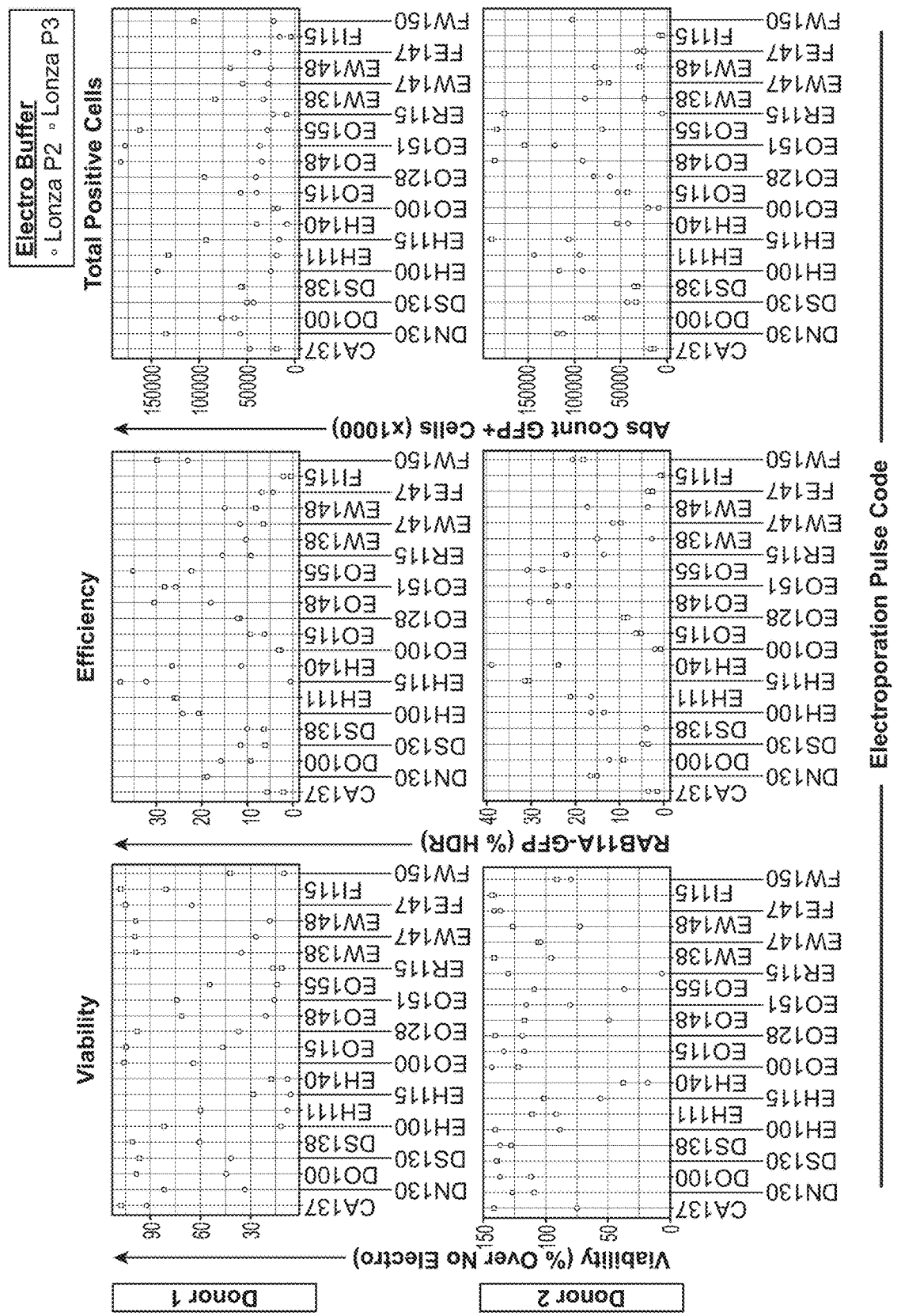
FIGS. 17A-C show optimization of electroporation parameters for delivery of large non-viral HDR templates. (A) Raw data shown here is summarized in FIG. 11E. Systematic variation of electroporation conditions on a Lonza 4D nucleofector. The ultimately chosen pulse code, EH115, was consistently the most efficient code when using the electroporation buffer Lonza P3. Other alternative codes, such as EO-148 optimized for total positive cells. (B) Confirmatory testing of a subset of electroporation conditions also identified pulse code EO-155 in OMEM buffer as a moderate efficiency but high total positive cell combination. (C) Electroporating a total volume (RNP+HDRT+Cells) of 24 uL made a large contribution to cell viability and maintained high efficiency. Electroporation volumes above 24 uL commonly cause electroporation failures. Efficiency of dsDNA RAB11A-GFP insertion (A, C) or dsDNA BATF-GFP insertion (B) and the absolute count of total GFP+ cells was performed 4 days following electroporation.
Figure 17B:
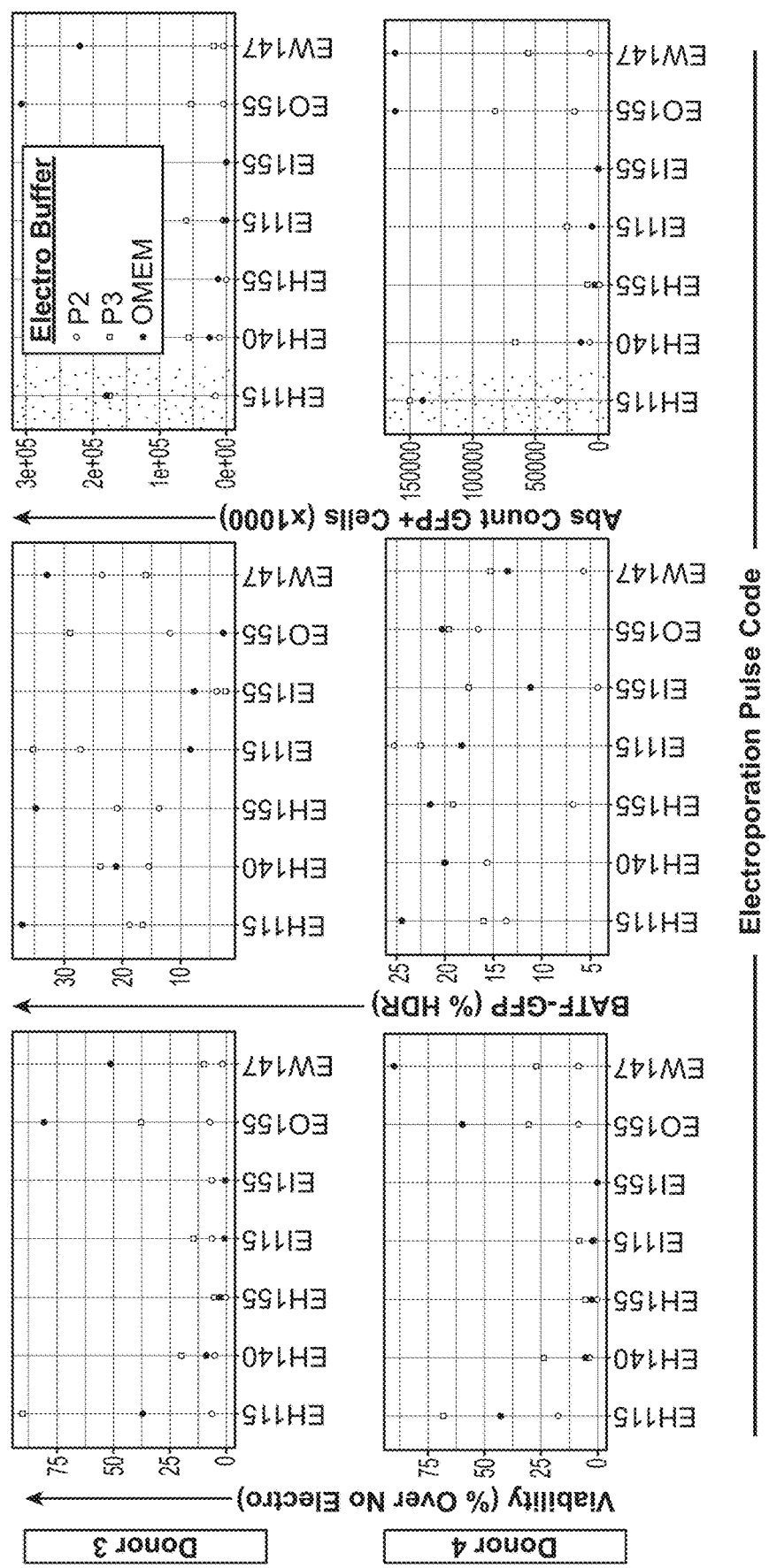
Figure 17C:
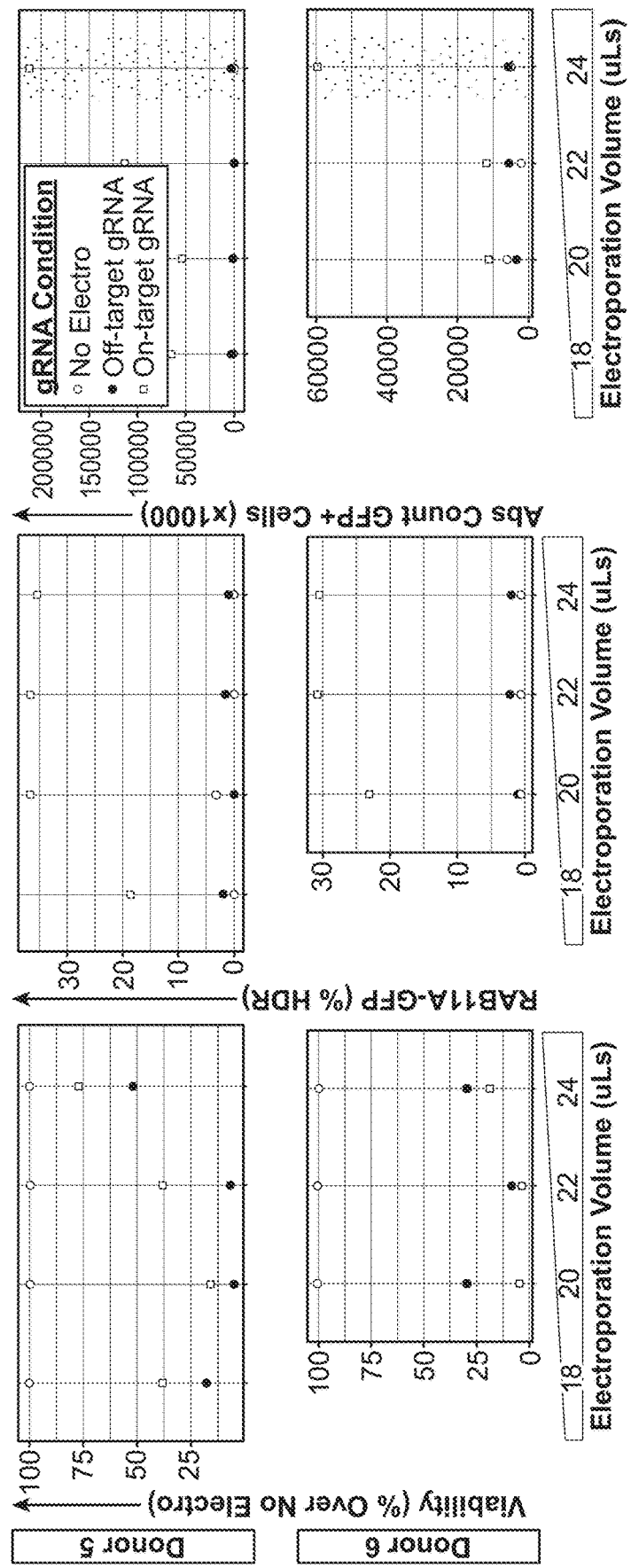

Non-viral genome targeting was optimized in primary human T cells. The protocol was adjusted for efficiency of target integration, cell viability, and the total number of integration-positive cells (FIG. 11A and FIG. 12). Cas9 RNPs were electroporated along with a dsDNA HDR template designed to introduce an N-terminal GFP-fusion to the housekeeping gene RAB11A (FIG. 11B). High-throughput flow cytometry performed 3-5 days after electroporation was used to monitor integration and cell viability. First, stimulation and cytokine treatments, both before and after electroporation, that markedly increased rates of gene targeting (FIG. 11C and FIGS. 13 and 14) were identified. These conditions allowed efficient targeting in fresh or frozen primary T cells isolated from a variety of sources (FIG. 15). Varying ratios of Cas9 RNP and HDR template concentrations were tested at different amounts in these well-stimulated T cells, (FIG. 11D and FIG. 16), and appropriate concentrations were identified that enabled efficient gene targeting. Finally, electroporation conditions to maximize gene targeting while preserving high levels of cell viability (FIG. 11E and FIG. 17) were tested. Non-viral gene targeting could achieve introduction of a GFP fusion to the endogenous RAB11A housekeeping gene in over 50% of cells in both primary human CD4+ and CD8+ T cells (FIG. 11F).

Rapid and Combinatorial Gene Targeting Applications

Figure 18A:
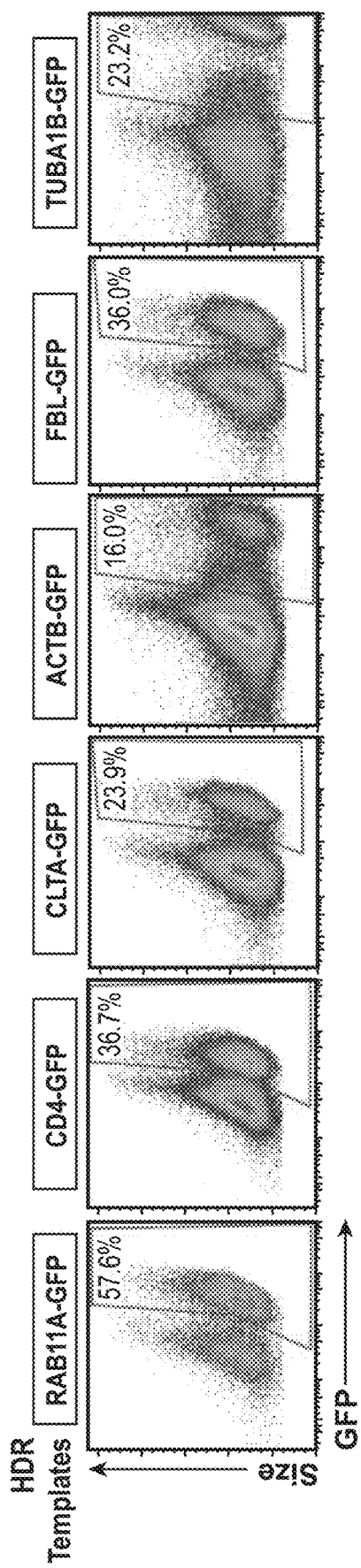
FIGS. 18A-D show the diverse applications of non-viral gene targeting in primary human T cells. (A) High efficiency genome targeting with GFP-fusion constructs could be achieved in multiple endogenous genes in primary human T cells using non-viral HDR templates and corresponding RNPs. (B) Confocal microscopy of living, primary human T cells 7 days after electroporation of the indicated HDR template confirmed the specificity of fusion-protein targeting. Scale bar in each image is 5 um. (C) Non-viral targeting of GFP-fusion constructs to the RAB11A and CD4 genes in bulk human primary T cells. RAB11A-fusions were GFP positive in both CD4+ and CD8+ cells, whereas CD4+-fusions were only positive in CD4$^+$ T cells (representative flow cytometry above, quantification below). (D) Primary human T cells were engineered to express GFP fused to the endogenous transcription factor, BATF. At 11 Days post electroporation, nuclei were isolated and CUT&RUN was performed. GFP-BATF and total BATF chromatin interaction sites were identified using anti-GFP or anti-BATF antibodies. Flow cytometry to assay viability and efficiency was performed at 4 days after electroporation (A, C, D). Displayed data is representative of at least two different donors.
Figure 18B:
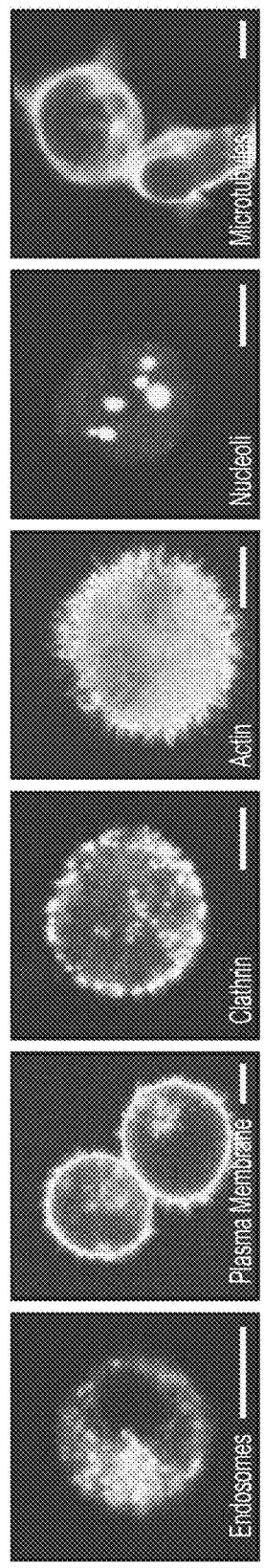
Figure 18C:
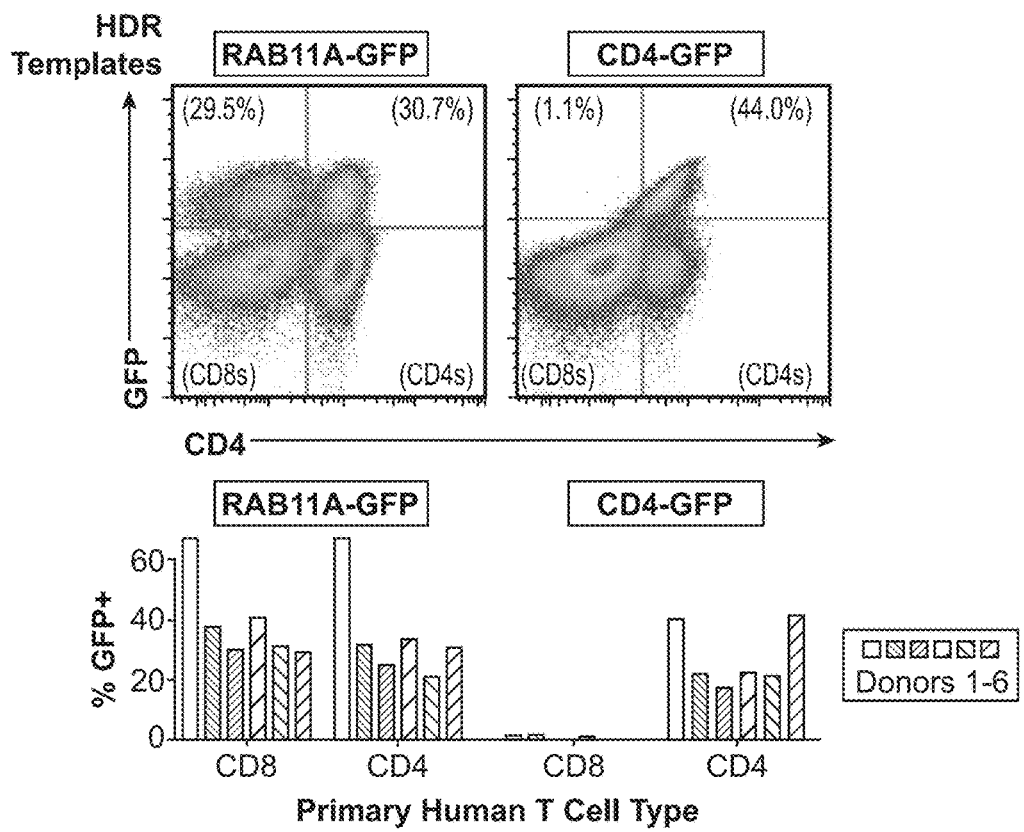
Figure 18D:
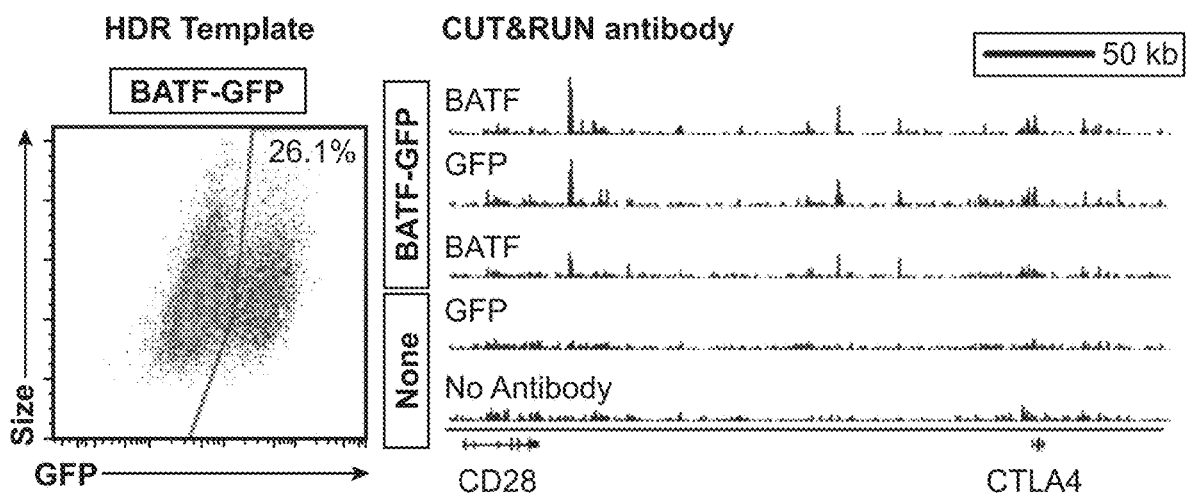
Figure 19A:
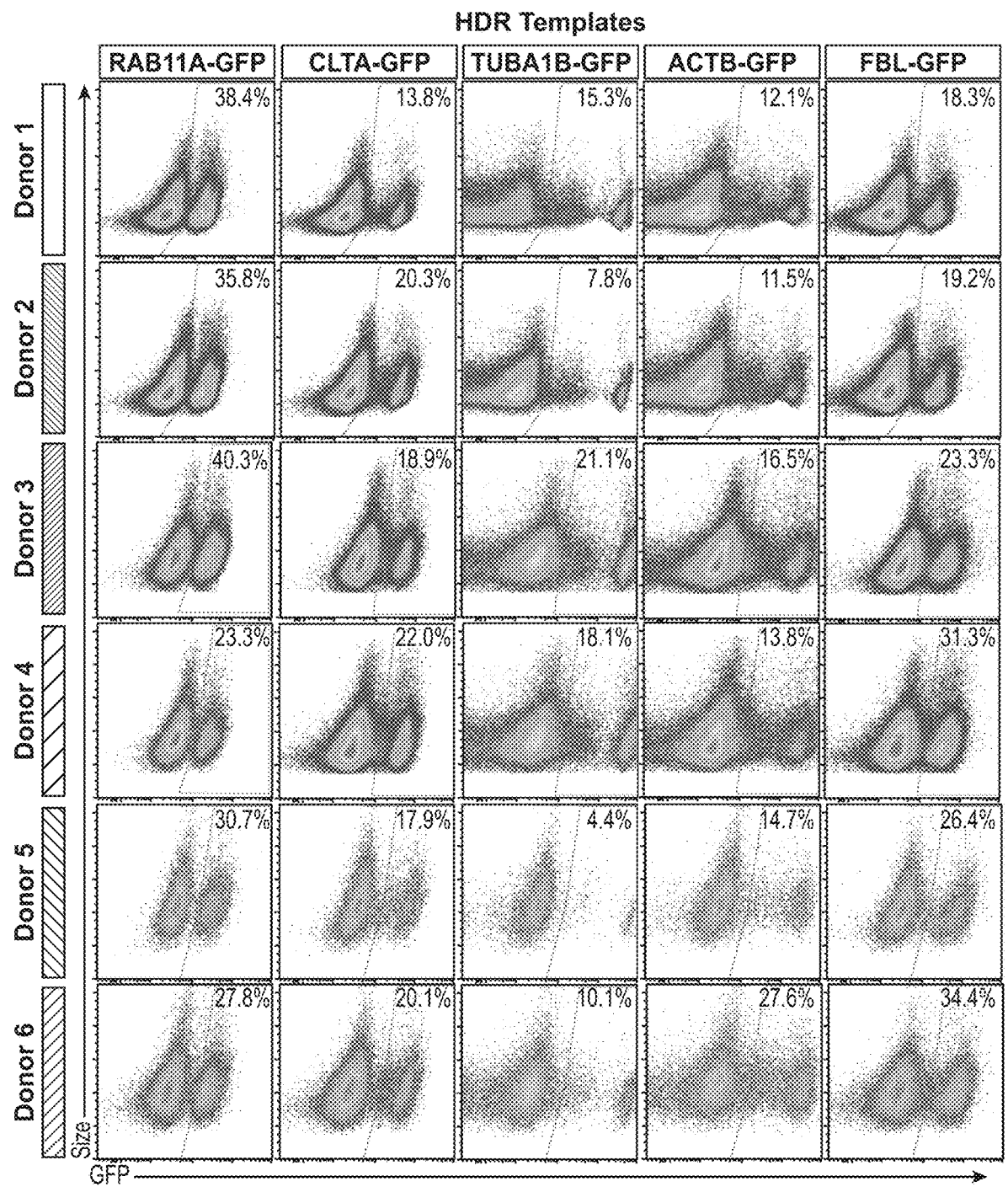
FIGS. 19A-B show reproducible non-viral gene targeting across target loci. (A) Four days after electroporation of one of five different GFP templates along with a corresponding RNP into primary CD3+CD8+ T cells from six healthy donors, GFP expression is observed across both templates and donors. Note the consistency in GFP expression levels within GFP positive cells across donors for each of the five loci (higher in TUBA1B and ACTB, lower in RAB11A and FBL tags). (B) Graphical summary of the percentage of GFP insertion in (A).
Figure 19B:
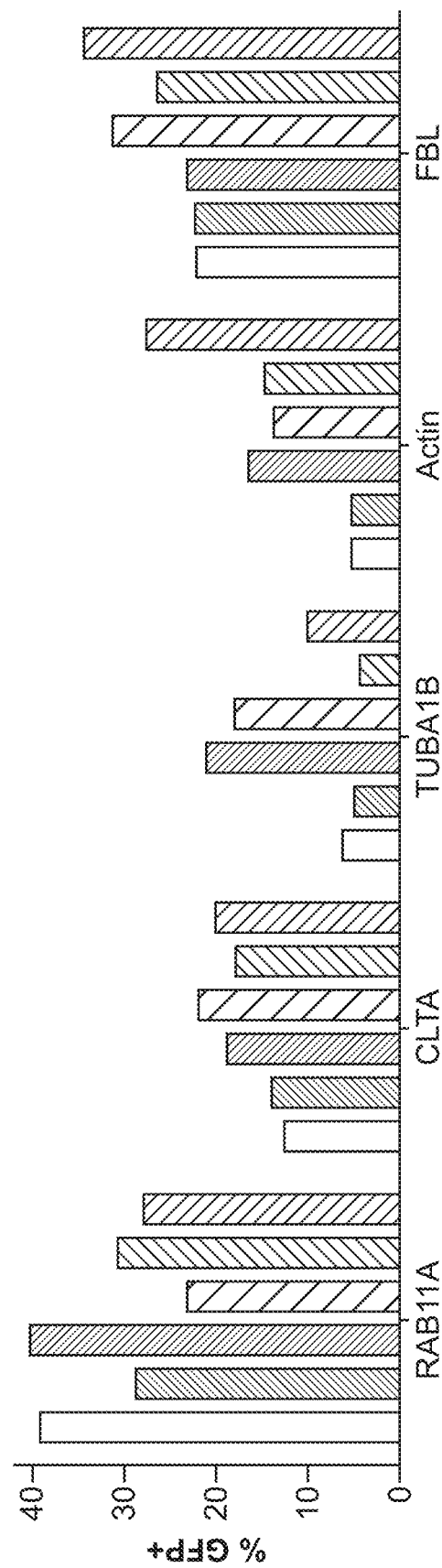
Figure 20A:
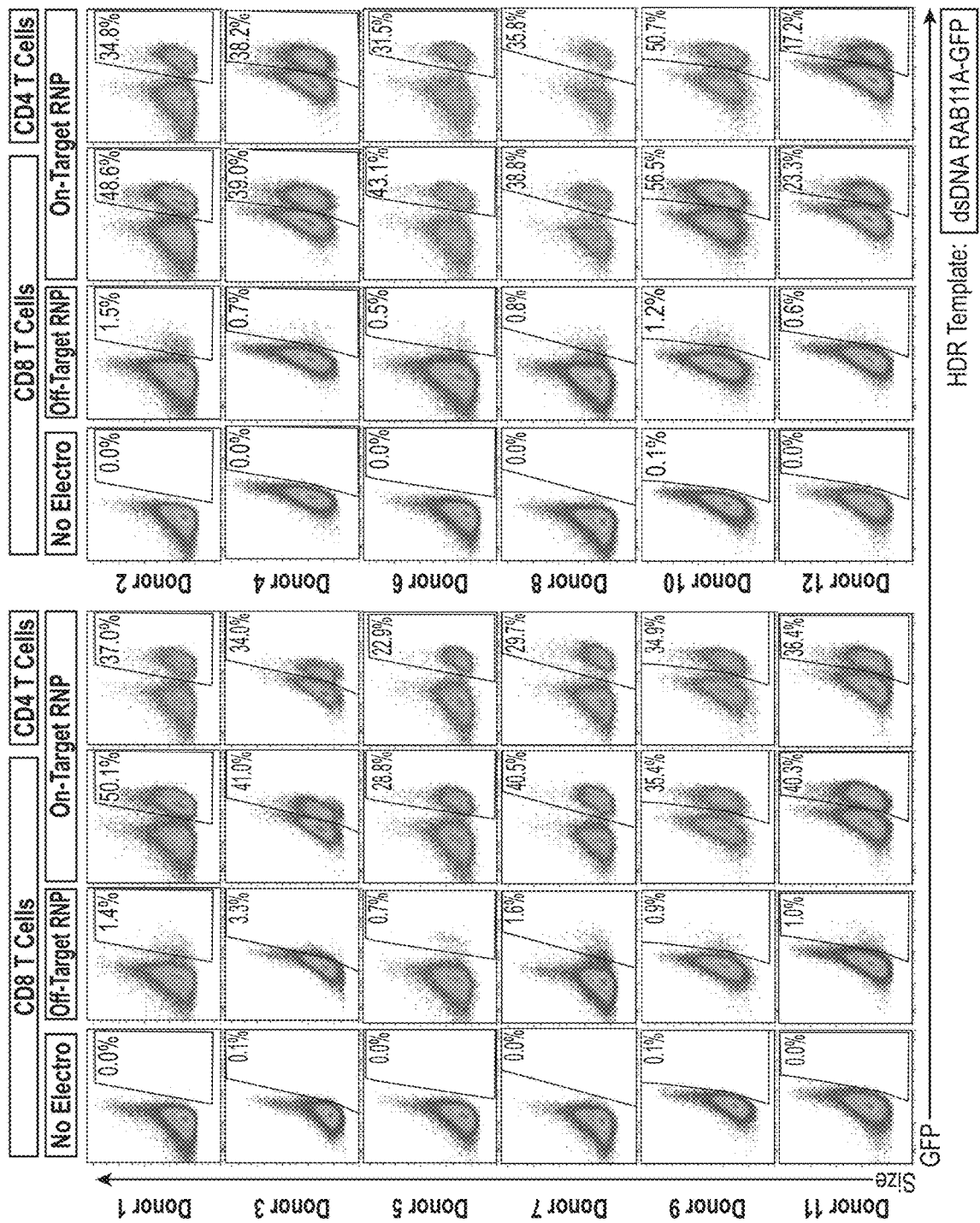
FIGS. 20A-B show reproducible non-viral gene targeting in a cohort of healthy donors. (A) A constant dsDNA RAB11A-GFP HDR template and RNP was electroporated using the optimized conditions developed for non-viral gene targeting in cells obtained from a cohort of twelve healthy donors. While there was significant variability in GFP insertion percentage among individual donors, all achieved robust integration of GFP (range 22% to 57% in CD8+ T cells). Some GFP expression was seen in cells electroporated with the dsDNA RAB11A-GFP HDR template with an off-target RNP targeting CXCR4 compared to no-electroporation controls. (B) Summary graph of GFP insertion percentages in (A). Across the 12 healthy donor cohort slightly higher rates of in GFP expression was seen in CD3+CD8+ T cells (mean 42.0%) compared to CD3+CD4+ T cells (mean 35.2%).
Figure 20B:
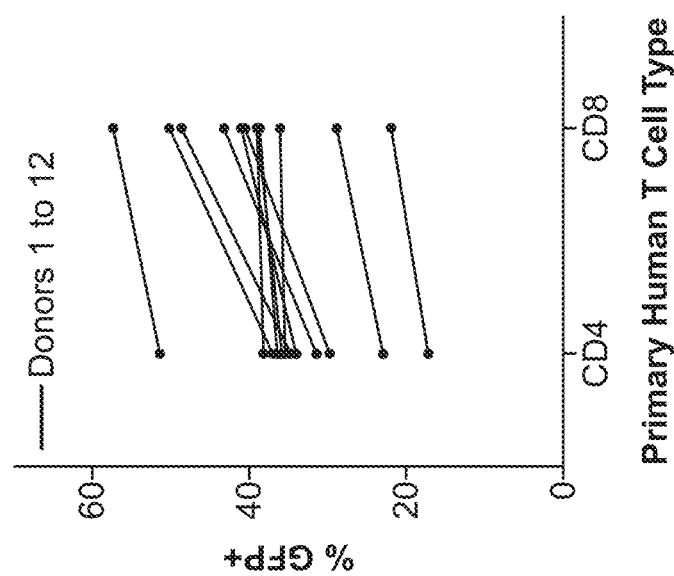

The simplicity and speed of non-viral gene targeting application of the methods provided herein across genomic sites and human blood donors (FIG. 18 and FIG. 12). Constructs encoding GFP-fusions with homologous flanking sequences were efficiently and reproducibly targeted to a variety of sites throughout the genome (FIG. 18A and FIG. 19). These targeted GFP fusions labeled a variety of subcellular structures (Leonetti et al. "A scalable strategy for high-throughput GFP tagging of endogenous human proteins," *Proc. Natl. Acad. Sci. U.S.A* 113, E3501-8 (2016)). Confocal microscopy confirmed the specificity of the fusion proteins produced by targeting diverse genes, and also demonstrated that targeting endogenous genes with GFP enabled imaging of protein localization in living human T cells (FIG. 18B). In cells from a cohort of a dozen healthy human donors, targeting GFP integrations into diverse genes proved highly reproducible in primary human T cells (FIGS.

19 and 20). The specificity of the targeted integrations and the cell-type specific expression pattern of the tagged genes was confirmed further by tagging the endogenously-encoded CD4 surface receptor with GFP. A linear relationship between CD4 and GFP expression specifically in tagged CD4+ T cells but not in CD8+ T cells (FIG. 18C) was observed. Taken together, these findings establish that non-viral genome targeting can be used to modify endogenous genes by inserting large DNA sequences into targeted sites in the genome.

Figure 21:
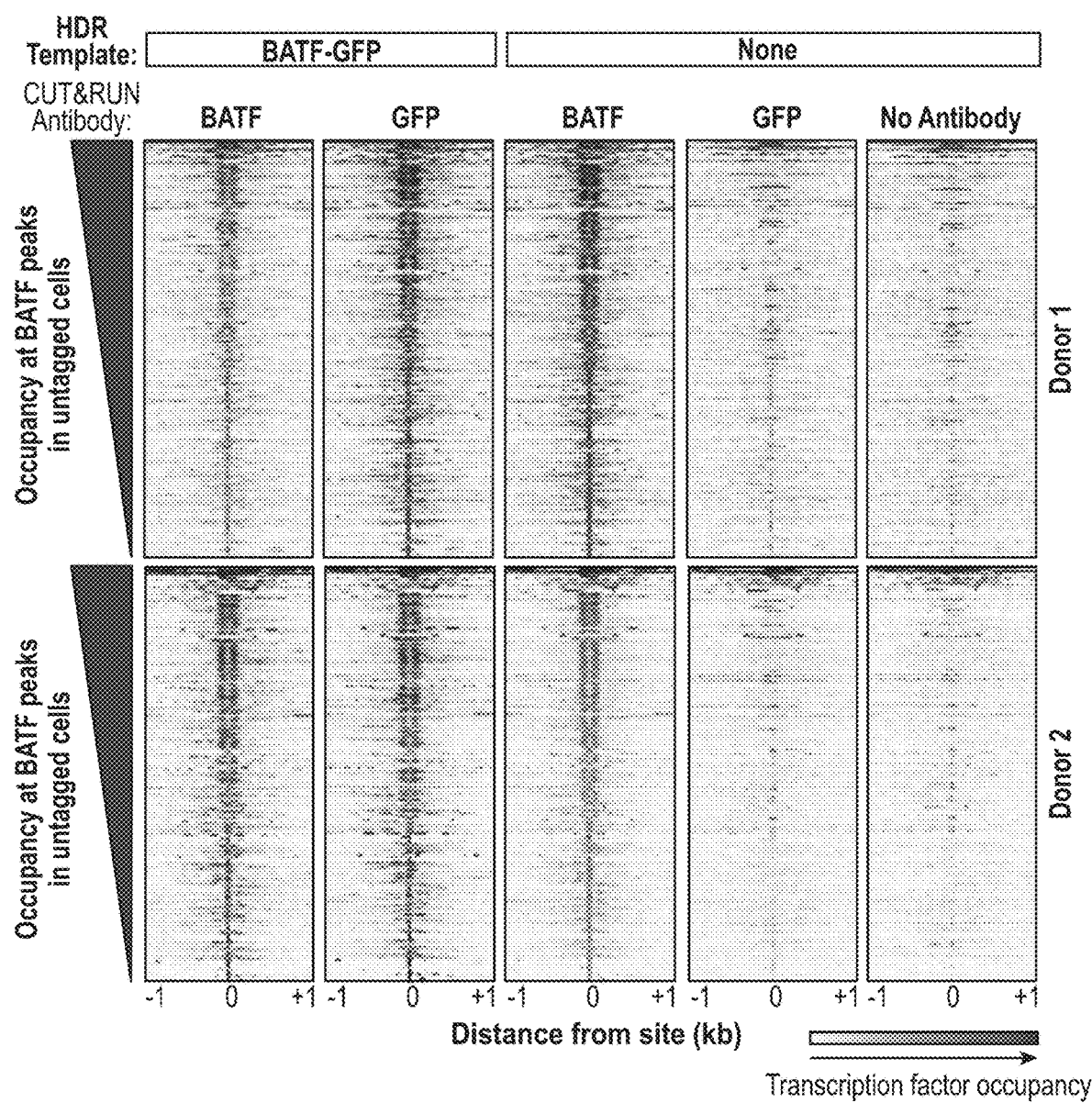
FIG. 21 shows endogenous tagging of transcription factor BATF for analysis of chromatin occupancy. Anti-BATF, anti-GFP, and no antibody heatmaps of CUT&RUN data obtained from primary human T cell populations electroporated with GFP-BATF fusion HDR template (untagged cells were not electroporated). Aligned CUT&RUN binding profiles for each sample were centered on BATF CUT&RUN peaks in untagged cells and ordered by BATF peak intensity in untagged cells.

Fusion tags not only permitted imaging of endogenous proteins, but also could be used for biochemical targeting of specific proteins. For example, ChIP-Seq, and more recently CUT & RUN (Skene and Henikoff, "An efficient targeted nuclease strategy for high resolution mapping of DNA binding sites," Elife 6(2017), doi:10.7554/eLife.21856), are widely used to map transcription factor binding sites; however these assays are often limited by availability of effective and specific antibodies. As a proof-of-principle anti-GFP antibodies were used to perform CUT & RUN in primary T cells where the endogenous gene encoding BATF, a critical TF, had been targeted to generate a GFP-fusion. Binding sites identified with anti-GFP CUT & RUN closely matched the sites identified with anti-BATF antibody (FIG. 18D and FIG. 21).

Figure 22A:
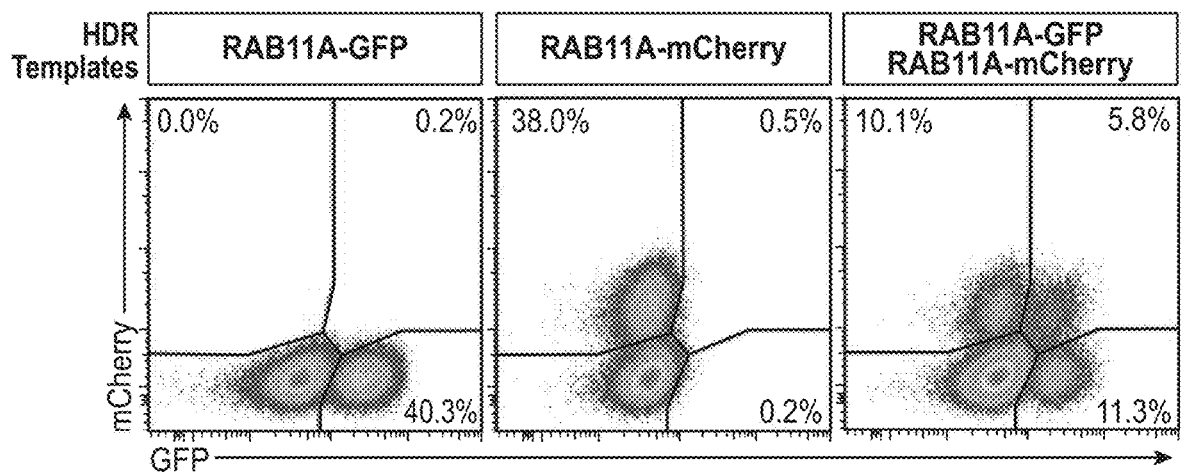
FIGS. 22A-E show combinatorial non-viral gene targeting. (A) Simultaneous electroporation of HDR templates to create RAB11A-GFP and/or RAB11A-mCherry fusions in primary human T cells. A distinct population of dual GFP+ mCherry+ cells was found when both templates are introduced concurrently, consistent with bi-allelic targeting. (B) The potential genotypes for individual cells in the quadrants are defined by expression of the two fluorophores. The observed level of bi-allelic integrations is higher in cells that acquire at least one integration than expected by chance (FIG. 23). Individual points represent replicates where the combination of the genes encoding the fluorescent proteins was varied (GFP+mCherry, GFP+BFP, mCherry+BFP) as was the amount of HDR template (3 to 6 ugs). (C-D) Multiplexed integration of HDR Templates at two separate genomic loci in the same primary human T cells. 2 ugs of each template (4 ugs total per electroporation) were electroporated together with 25 pmols of each RNP (50 pmols total). Cells positive for integration at one site (e.g. GFP+) were much more likely to have an integration at the second site (e.g. also be mCherry+) than cells lacking the first integration. (E) Simultaneous non-viral gene targeting of large insertions to three distinct genomic loci. 1.5 ugs of each template (4.5 ugs total) were electroporated together with 20 pmols of each corresponding RNP (60 pmols total). Similarly to two site multiplexing, cells positive for a single integration (mCherry+ in Q-II and GFP+ in Q-III) were more likely to have a second integration (BFP+) compared to those without (Q-I). Cells positive for two integrations (GFP+ and mCherry+, Q-IV) are even more likely to have an integration of the third gene (BFP+). Below is a bar graph quantification of cells that are single, double and triple positive for fluorophores. All fluorescent readouts were performed 4 days post-electroporation. Displayed data are representative of at least two different donors except panel E (one donor).
Figure 22B:
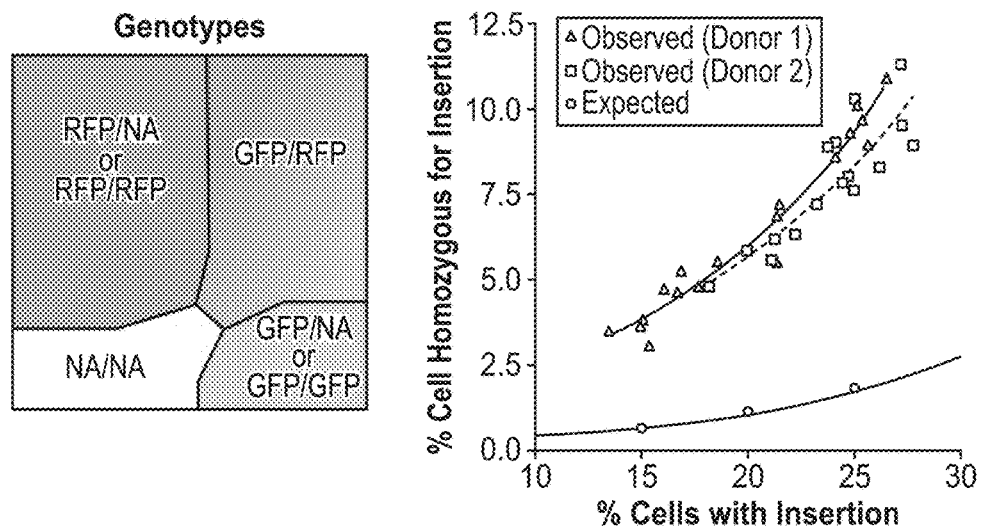
Figure 23C:
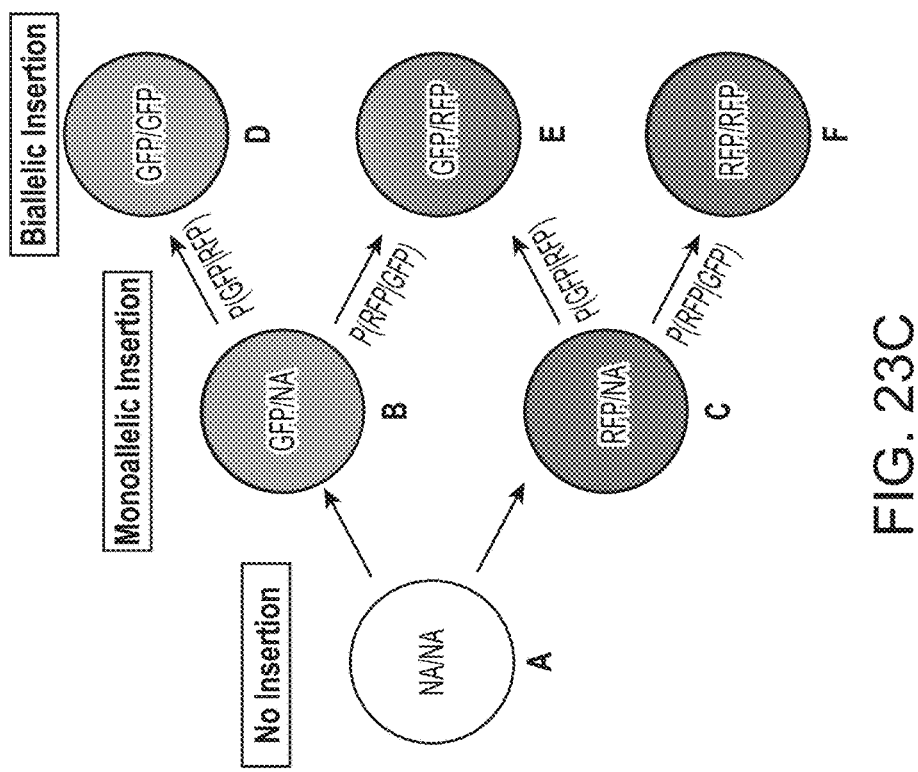
Figure 23A:
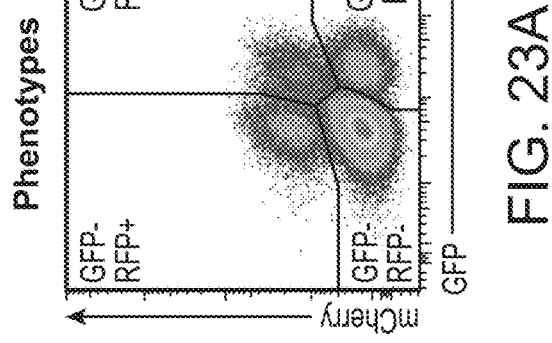
Figure 23B:
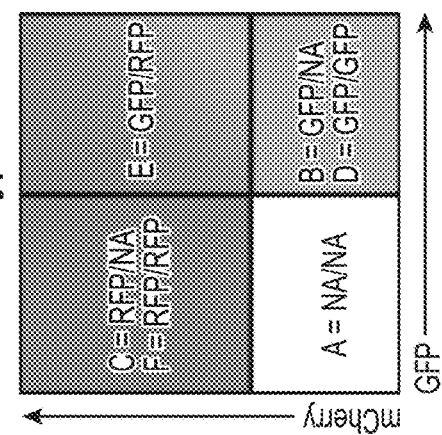

Targeting two alleles of the same gene with two distinct fluorophores would provide a way to quantify and enrich cells with bi-allelic gene modifications. Two distinct fluorescent proteins targeting the same site at the RAB11A gene (FIG. 22A and FIG. 23) were introduced and showed that >5% of cells had successful bi-allelic integrations. Importantly, the number of cells that express both fluorescent proteins underestimates the percentage of cells with bi-allelic integrations because some cells will have received either GFP or mCherry on both alleles. A model was constructed to account for homozygous integrations of the same fluorescent protein (FIG. 22B, FIG. 23). This model estimates that there were bi-allelic integrations in the RAB11A gene in up to ~10% of cells. This suggests that cells with one RAB11A integration are more likely to have also undergone a second targeted integration, and this effect was observed across three genomic loci (FIG. 23). Co-delivery of three fluorescent-tags targeting the RAB11A locus demonstrated very low rates of cells that express all three fluorophores, consistent with low rates of off-target integrations in these experiments (FIG. 23G). In summary, using multiple non-viral constructs to targeting the same locus allows identification of bi-allelic genome editing in human T cells.

Figure 22C:
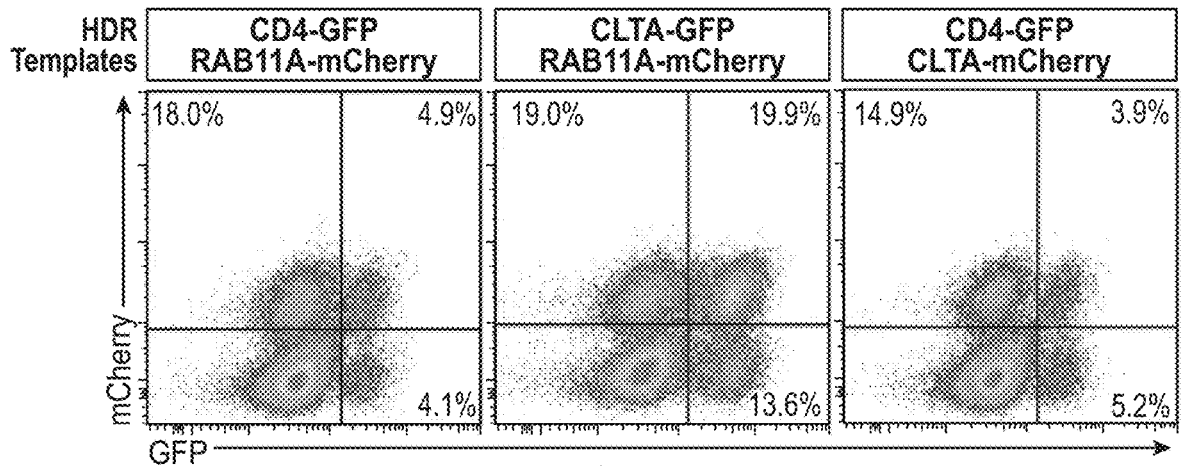
Figure 22D:
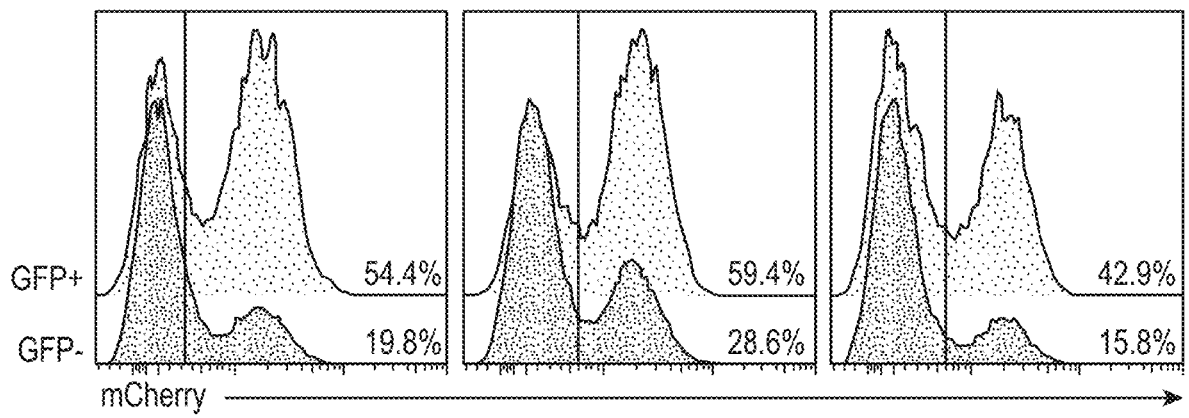
Figure 22E:
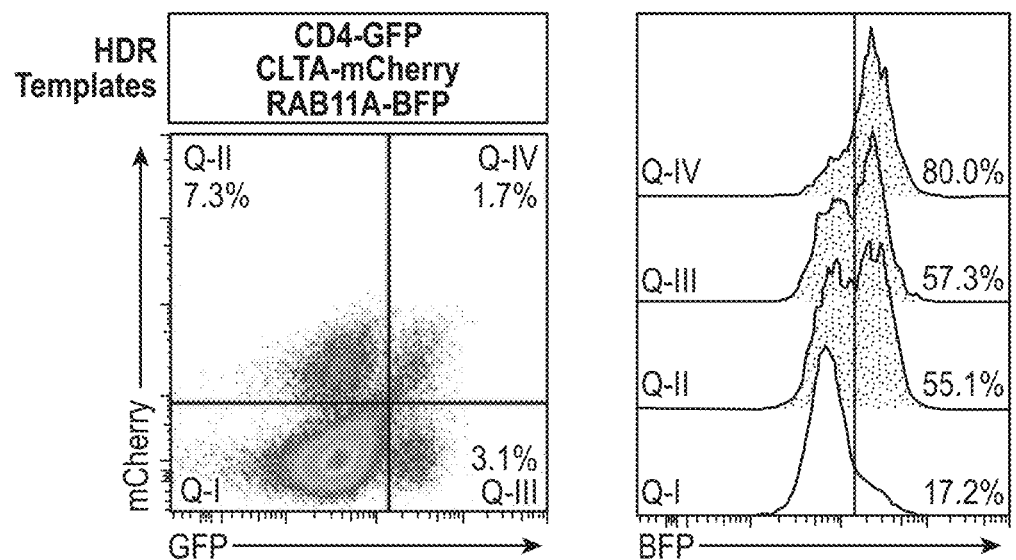
Figure 22E:
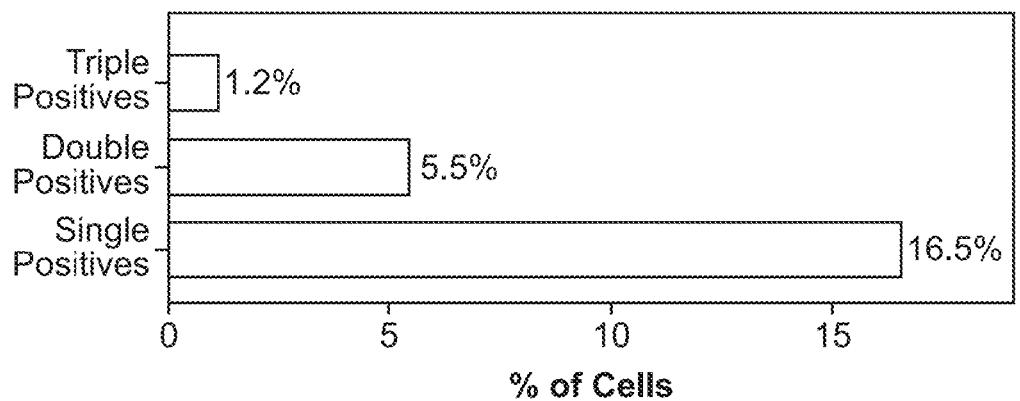
Figure 24A:
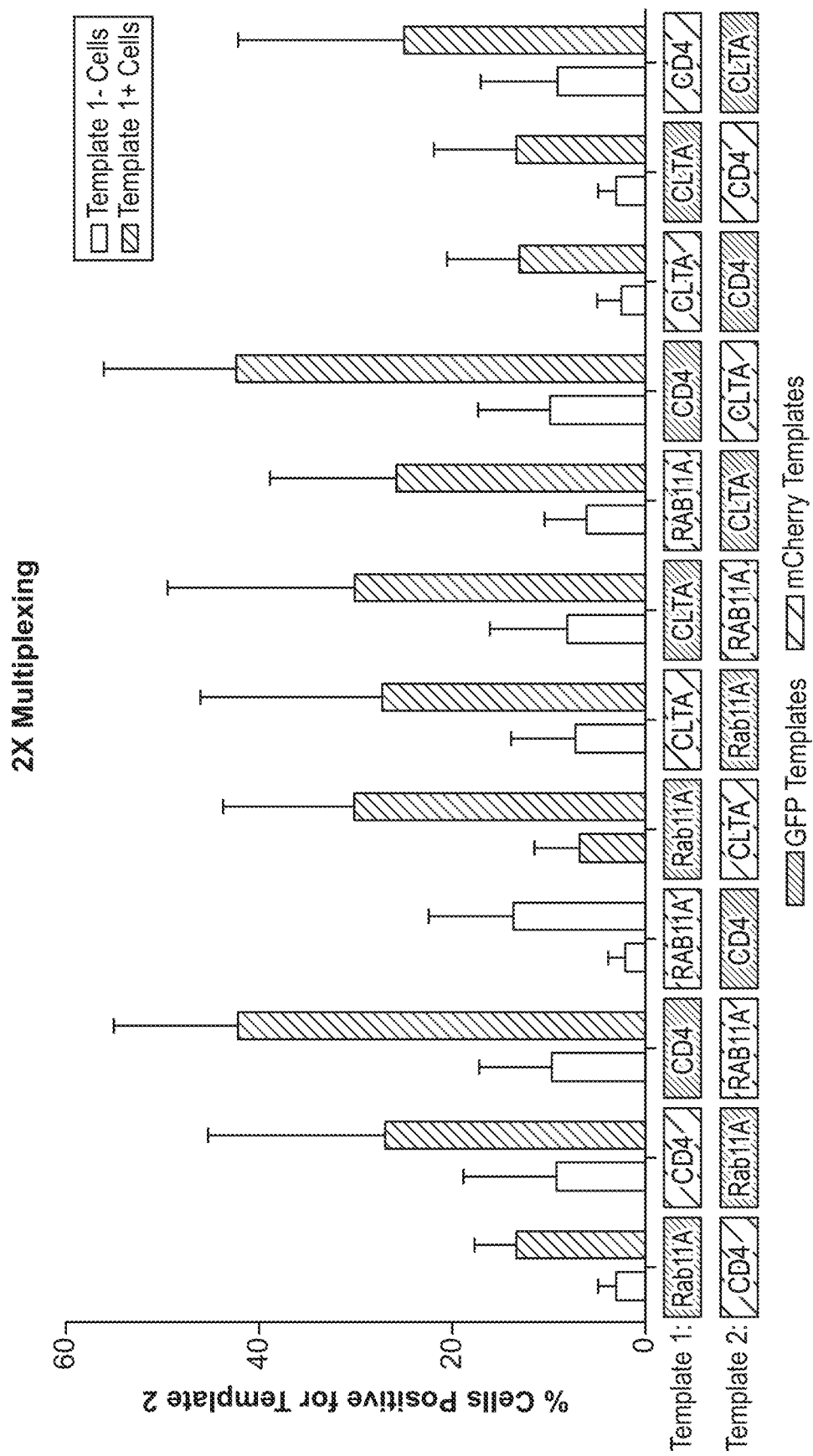
FIGS. 24A-B show multiplexed integrations showing that acquisition of HDR integration at one locus increases likelihood of HDR at additional loci. (A) Two HDR template permutations from a set of six dsDNA HDR templates (targeting RAB11A, CD4, and CLTA; each site with GFP or RFP) were electroporated into CD3+ T cells isolated from healthy human donors. Four days after electroporation of the indicated two HDR templates along with their two respective on-target RNPs, the percentage of cells positive for each template was analyzed when gating on cells either positive or negative for the other template. Not only was two-template multiplexing possible across a variety of template combinations, but gating on cells positive for one template (Template 1+ Cells,) yielded an enriched population of cells more likely to be positive for the second template compared to cells negative for the first (Template 1− Cells, Black). 2 ugs of each template, along with 30 pmols of each associated RNP, were electroporated for dual multiplexing experiments. (B) Electroporation of an additional template allows for 3 site multiplexing using a variety of HDR template combinations. Cells positive for the third template can be further enriched by gating on cells positive for both other templates when compared to single positive cells. Displayed data are means+standard deviation from multiple technical replicates from two healthy human donors.
Figure 24B:
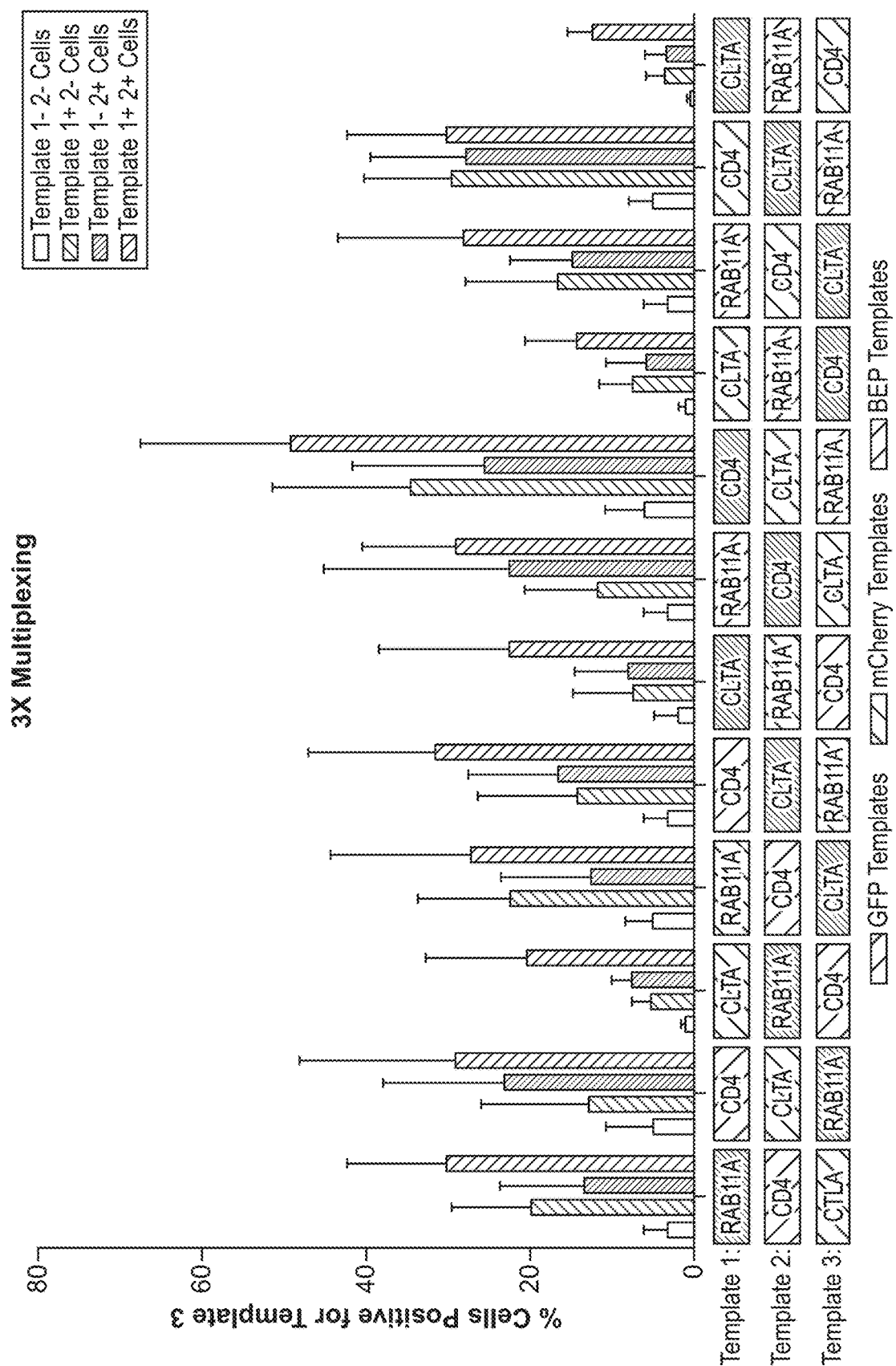

Multiplex editing of combinatorial sets of genomic sites would offer expanded research and therapeutic applications. Whether multiple non-viral HDR templates could be co-delivered with multiple RNPs to generate primary cells with more than one modified locus was tested. It was found that, not only is multiplexed gene targeting possible (FIG. 22C), but cells with two modifications were enriched by gating on the cells that had one modification (FIG. 22D and FIG. 24) (Agudelo et al., "Marker-free coselection for CRISPR-driven genome editing in human cells," Nat. Methods. 14, 615-620 (2017)). Triple gene targeting was also achieved and could significantly enrich for cells that had a third modification by gating on the cells with two targeted insertions (FIG. 22E and FIG. 24). Overall, non-viral gene targeting can be used to enable complex genetic modifications of primary T cells that could be used for a variety of research and therapeutic applications.

D10A Nickase and ssDNA HDR Templates Reduce Off-Target Integrations

Figure 27A:
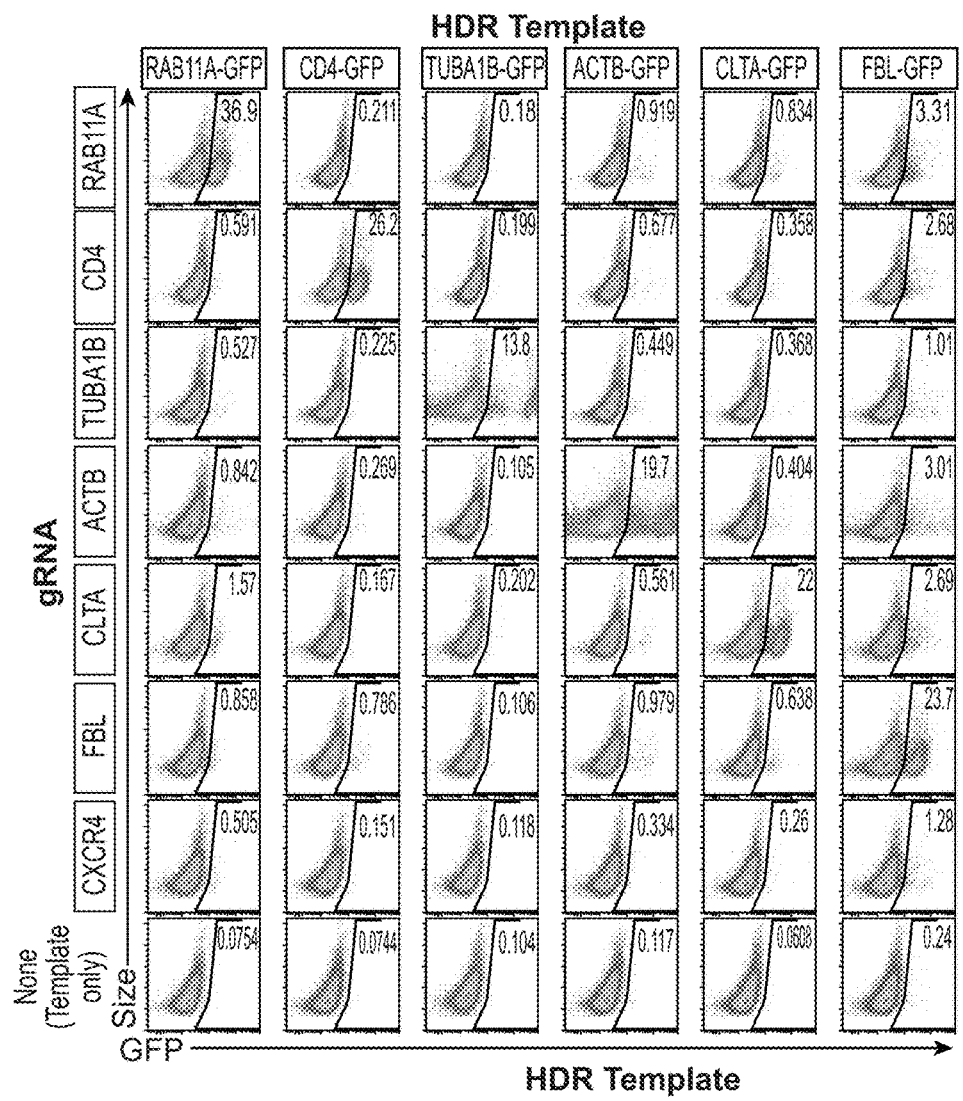
FIGS. 27A-B show GFP expression across a HDR template versus gRNA matrix. (A) GFP expression was analyzed in CD3+CD4+ primary human T cells from a healthy donor 7 days following electroporation of a matrix of dsDNA HDR templates and their corresponding gRNAs, along with a CXCR4 gRNA and a no RNP control. As expected with a dsDNA template, off-target integrations were seen across combinations, but for all gRNAs and HDR templates the highest GFP expression was seen in the on-target condition. (B) Heat map summary of flow cytometry data in (A). One HDR template, a C-terminal GFP fusion tag into the nuclear factor FBL, had consistently higher off-target expression across gRNAs.
Figure 27B:
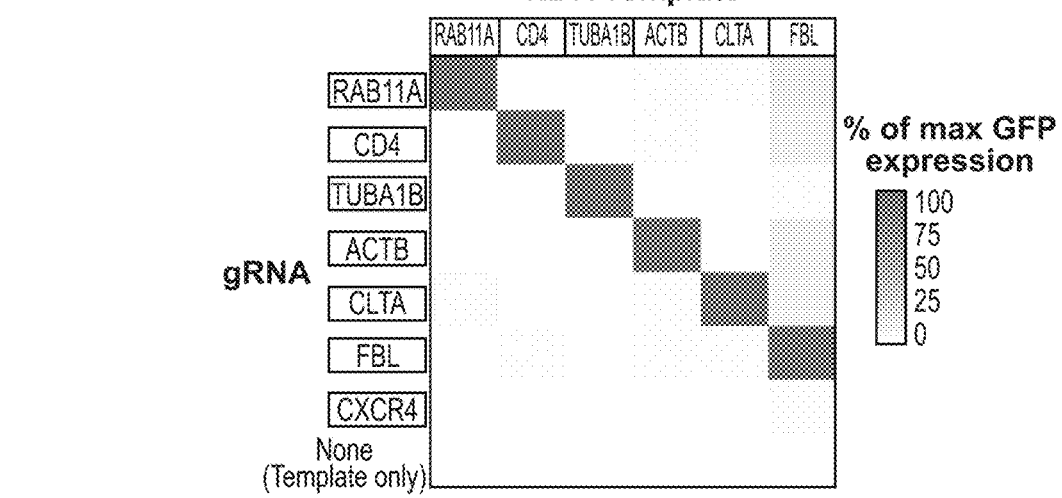

One of the major concerns using HDR templates, especially for therapeutic applications, is the potential for off-target integrations. This has been observed even when integrase-deficient AAVs were used as donor templates (Dever et al., "CRISPR/Cas9 β-globin gene targeting in human haematopoietic stem cells," Nature 539, 384-389 (2016)). Similar evidence of functional off-target integrations using a linear dsDNA template for non-viral gene targeting was found here. Double-stranded DNA templates can integrate in an HDR-independent manner at sites of naturally occurring dsDNA breaks (Murnane et al. "Recombination events during integration of transfected DNA into normal human cells," Nucleic Acids Res. 18, 2733-2738 (1990)), as well as at the specific dsDNA breaks induced by targeted nucleases such as Cas9, an effect called Homology-Independent Targeted Integration ((Auer et al. "Highly efficient CRISPR/Cas9-mediated knock-in in zebrafish by homology-independent DNA repair," Genome Res. 24, 142-153 (2014); and Suzuki et al. "In vivo genome editing via CRISPR/Cas9 mediated homology-independent targeted integration," Nature 540, 144-149 (2016)). Unintended non-homologous integrations using an N-terminal GFP-RAB11A fusion construct which contained the endogenous RAB11A promoter sequence within its 5' homology arm were looked for; this construct can drive GFP expression at off-target integration sites (FIG. 25A and FIG. 26). It was found that functional off-target integrations were present in cells from different biological donors (FIG. 25B), and were seen in experiments with different target sequences and HDR templates (FIGS. 26 and 27). Off-target integrations must be minimized in cells destined for therapeutic use to ensure that integrated sequences remain under proper endogenous regulation and that off-target sites are not disrupted.

Figure 28A:
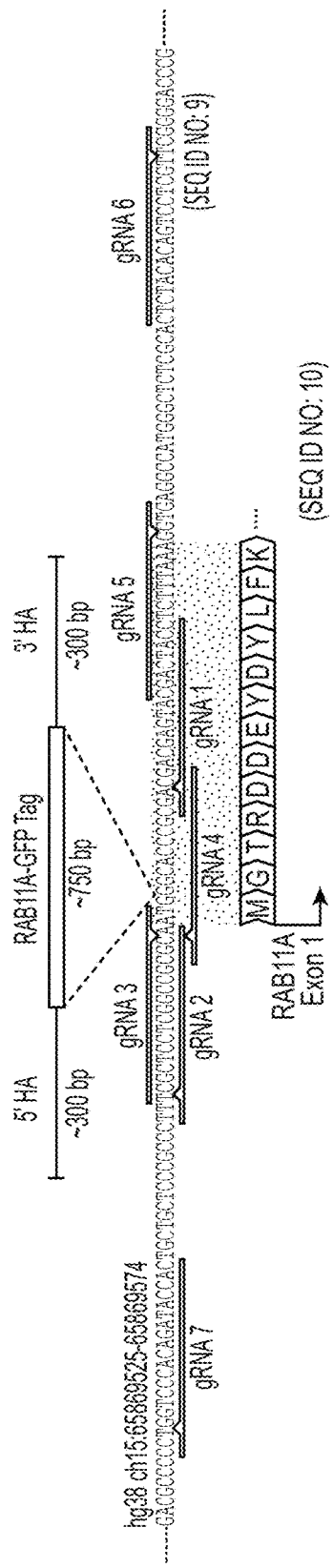
Figure 28B:
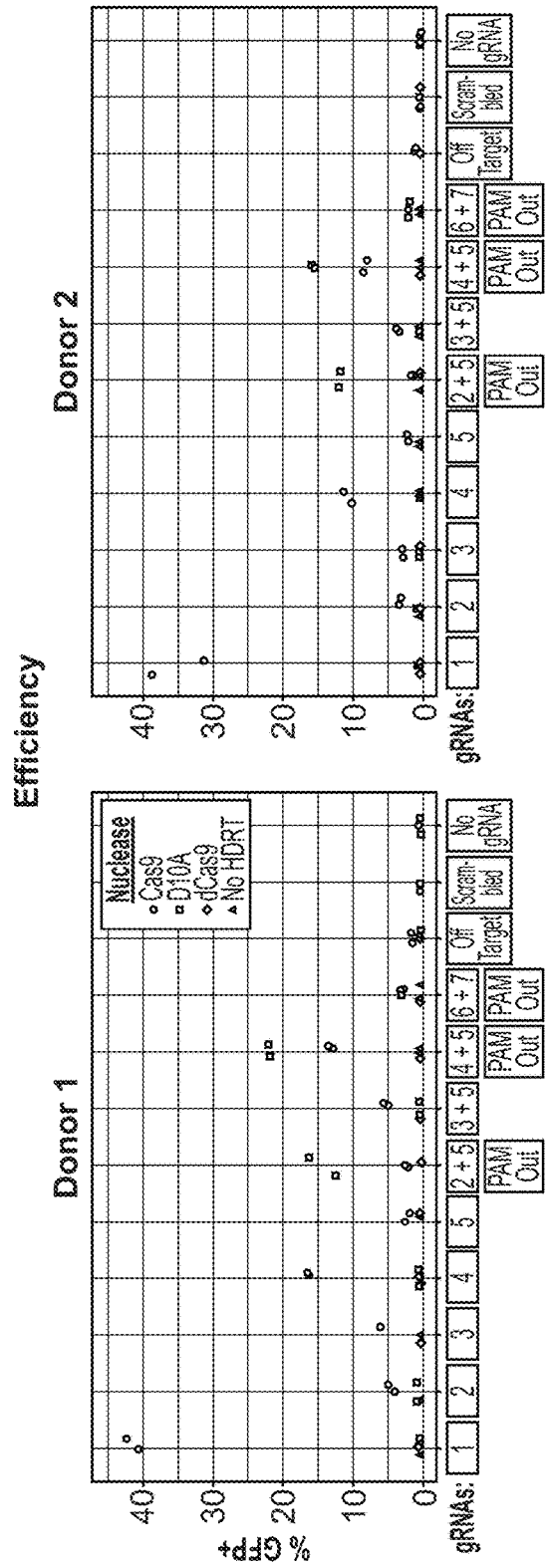
Figure 29D:
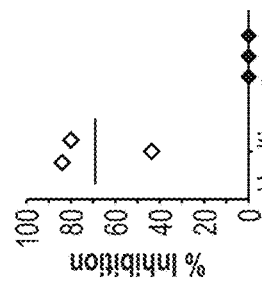
Figure 29E:
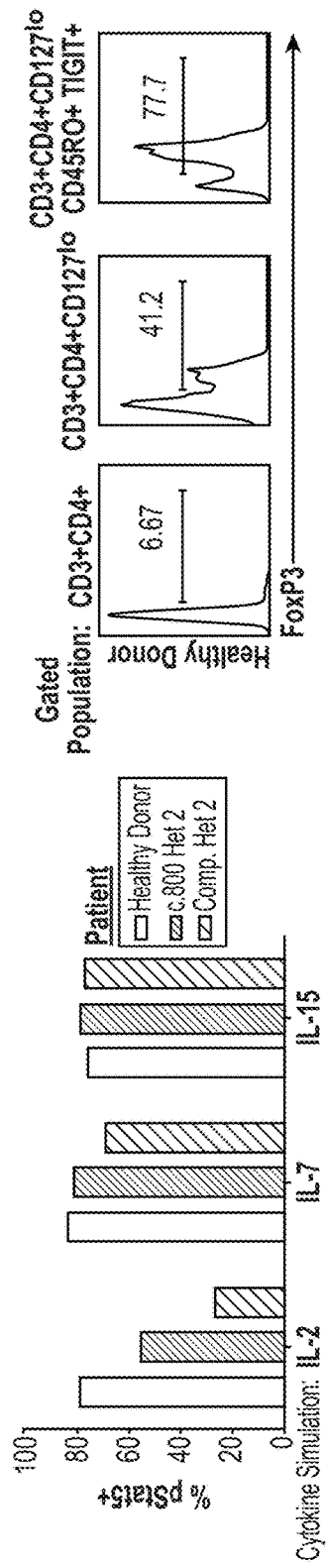
Figure 29F:
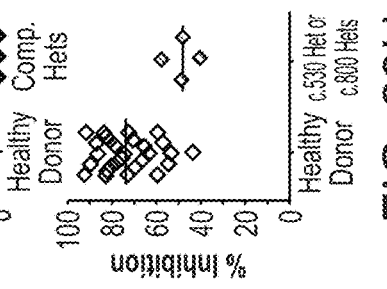
Figure 29G:
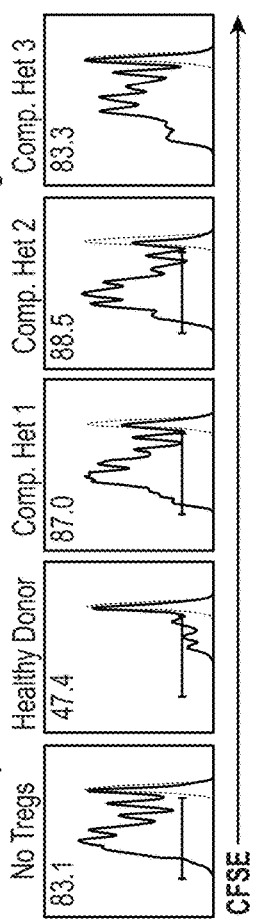
Figure 29H:
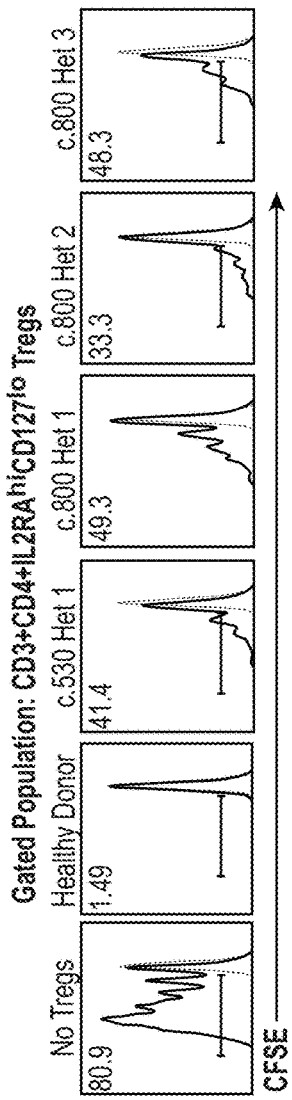

To reduce off-target integrations caused by off-target Cas9 cutting, non-viral gene targeting was performed using the D10A Cas9 nickase variant. This variant requires that two gRNAs bind and cleave in close proximity to produce a double strand break, thus reducing the number of off-target dsDNA breaks (Miyaoka et al., "Systematic quantification of HDR and NHEJ reveals effects of locus, nuclease, and cell type on genome-editing,"Sci. Rep. 6 (2016), doi:10.1038/srep23549; Vriend et al., "Distinct genetic control of homologous recombination repair of Cas9-induced double-strand breaks, nicks and paired nicks," Nucleic Acids Res. 44, 5204-5217 (2016); and Bothmer et al., "Characterization of the interplay between DNA repair and CRISPR/Cas9-induced DNA lesions at an endogenous locus," Nat. Commun. 8, 13905 (2017)). A series of gRNA combinations at the RAB11A locus for GFP integration were tested, a set of "PAM-Out" guides that showed efficient introduction of GFP when using the D10A nickase (FIG. 28) were found. As expected, use of D10A with a single off-target guide showed markedly reduced functional off-target integrations when compared to Cas9, equivalent to the level seen when nuclease-incompetent dCas9 was used (FIG. 25C).

Even using the D10A nickase, dsDNA HDR templates still gave rise to rare but observable off-target integrations (comparable to the rate observed with no Cas9 nuclease), perhaps at naturally occurring dsDNA breaks (FIGS. 25A and C). It was reasoned that the remaining off-target integrations could be eliminated by replacing the dsDNA HDR templates with long ssDNA HDR templates, which cannot integrate non-specifically at double strand breaks (Quadros et al., "Easi-CRISPR: a robust method for one-step generation of mice carrying conditional and insertion alleles using long ssDNA donors and CRISPR ribonucleoproteins," *Genome Biol.* 18, 92 (2017); and Leonetti et al. world wide web at biorxiv.org/content/early/2017/08/21/178905).

Figures 25E, 25F:
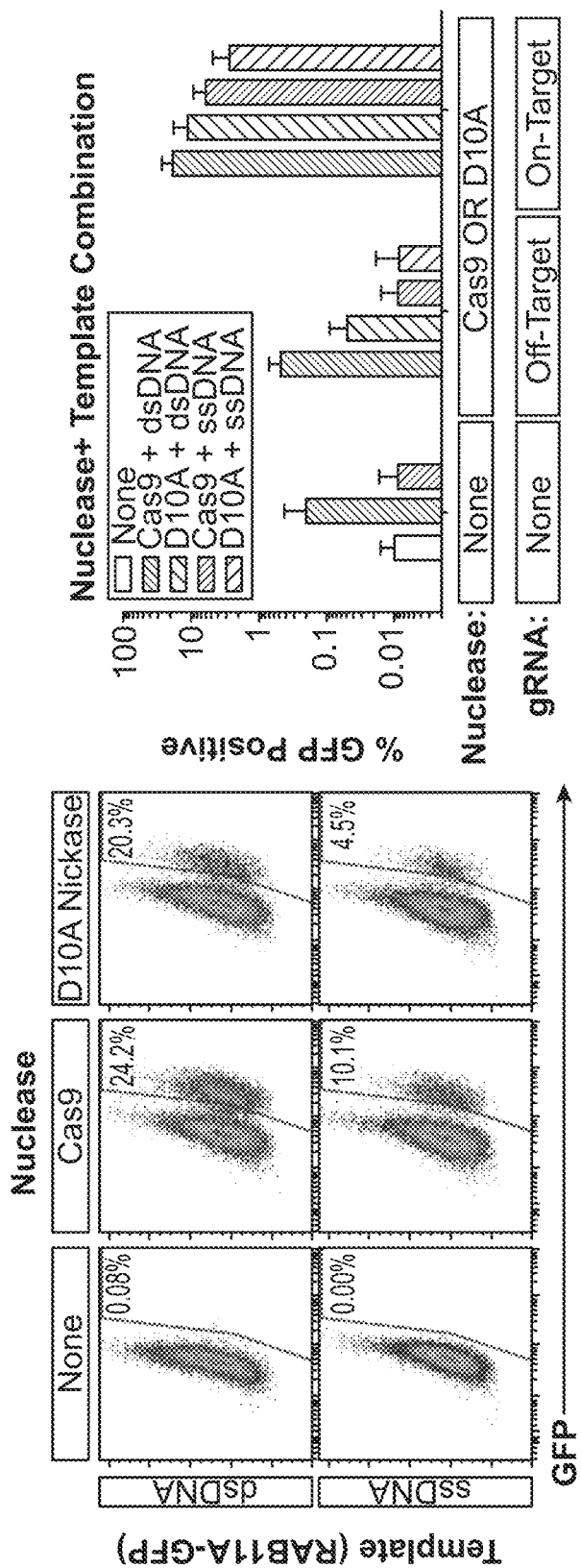

To test this hypothesis, ssDNA HDR templates were generated with two methods that produce the large amounts of long ssDNA required for electroporation (FIG. 35). ssDNA HDR templates reduced functional off-target integrations approximately 100-fold, while maintaining efficient on-target integration (FIG. 25D). It was possible to use D10A Cas9 nickase with ssDNA templates. In these experiments, although on-target integration rates were reduced, non-specific integrations were reduced to background levels seen without template (FIGS. 25E and F). For sites where potential off-target activity is a concern, D10A Cas9 nickase and ssDNA HDR templates can be employed to reduce the rates of integration arising from off-target induced double strand breaks and naturally occurring breaks respectively, which may make this an attractive method for therapeutic modification of patient T cells.

Therapeutic Mutation Correction by Non-Viral Gene Targeting

Application of non-viral gene targeting to correct the mutations that cause monogenic immune dysregulation in T cells from patients was pursued. A family with monogenic primary immune dysregulation with autoimmune disease caused by recessive loss-of-function mutations in the gene encoding the IL-2 alpha receptor (IL2RA), also known as CD25 (Sharfe et al. "Human immune disorder arising from mutation of the alpha chain of the interleukin-2 receptor," *Proc. Natl. Acad. Sci. U.S.A* 94, 3168-3171 (1997); Caudy et al. "CD25 deficiency causes an immune dysregulation, polyendocrinopathy, enteropathy, X-linked—like syndrome, and defective IL-10 expression from CD4 lymphocytes," *J. Allergy Clin. Immunol.* 119, 482-487 (2007); and Goudy et al., "Human IL2RA null mutation mediates immunodeficiency with lymphoproliferation and autoimmunity," *Clin. Immunol.* 146, 248-261 (2013)) was identified. IL2RA is essential for Tregs and immune homeostasis (Sakaguchi et al. "Immunologic self-tolerance maintained by activated T cells expressing IL-2 receptor alpha-chains (CD25). Breakdown of a single mechanism of self-tolerance causes various autoimmune diseases," *J. Immunol.* 155, 1151-1164 (1995); and Rudensky et al. "Regulatory T cells and Foxp3," *Immunol. Rev.* 241, 260-268 (2011)), and the children in the family who are compound heterozygotes with two loss-of-function mutations have pleiotropic autoimmune manifestations (Table 1). One is affected by neonatal-onset type 1 diabetes (T1D) and another has developed recalcitrant autoimmune cytopenias during childhood. All three IL2RA-deficient family members demonstrated pathologic serum autoantibodies. The IL2RA-deficient children have an almost complete loss of IL2RA cell surface expression and therefore virtually no detectable CD3+CD4+ CD25hiCD127lo Tregs in their blood, whereas family relatives carrying heterozygous IL2RA mutations display decreased IL2RA expression on their Tregs (FIG. 30). However, frequencies of CD3+CD4+CD127loFOXP3+ T cells in the IL2RA-deficient subjects resemble those in healthy donors (HD) and heterozygous family members, suggesting that Treg-like cells develop and persist despite the IL2RA mutations. Using a strategy to isolate Tregs without CD25 expression, it was found that CD3+CD4+ CD127loCD45RO+ TIGIT+ Treg-enriched cells from CD25-deficient subjects showed a defective ability to suppress the proliferation of responder T cells (Tresps) as compared to HD counterparts (FIG. 29). In contrast, Tregs from relatives with a single heterozygous IL2RA mutation could inhibit Tresp proliferation, albeit with suboptimum capacity (FIG. 29). Hence, correcting functional IL2RA expression on the surface of FOXP3+ T cells from these patients may represent a valuable approach for developing an ex vivo gene therapy.

TABLE 1

| Patient | Sex | IL2RA Mutation Status | Autoimmune Disease Phenotype | Clinical History | Autoantibodies |
|---|---|---|---|---|---|
| c.530 Het 1 (Mother) | F | c.530A>G/ WT | None | Childhood ear infections | None |
| c.800 Het 1 (Father) | M | c.800delA/ WT | None | No medical issues | None |
| c.800 Het 2 | F | c.800delA/ WT | None | Allergies | None |
| c.800 Het 3 | F | c.800delA/ WT | None | No medical issues | None |
| Comp Het 1 | M | c.530A>G/ c.800delA | Type 1 Diabetes | Insulin dependent diabetes in first year of life | anti-GAD, ICA512 |
| Comp Het 2 | M | c.530A>G/ c.800delA | Diabetes Auto-antibodies | Ear infections; Eczema | anti-GAD, MIAA, ICA |
| Comp Het 3 | F | c.530A>G/ c.800delA | Immune Thrombocytopenia Purpura; Autoimmune Neutropenia | Ear infections; Hemolytic anemia; Nummular dermatitis; Hypercellular bone marrow with inverted CD4/CD8 ratio; Mouth ulcers | anti-platelet |

Figure 30D:
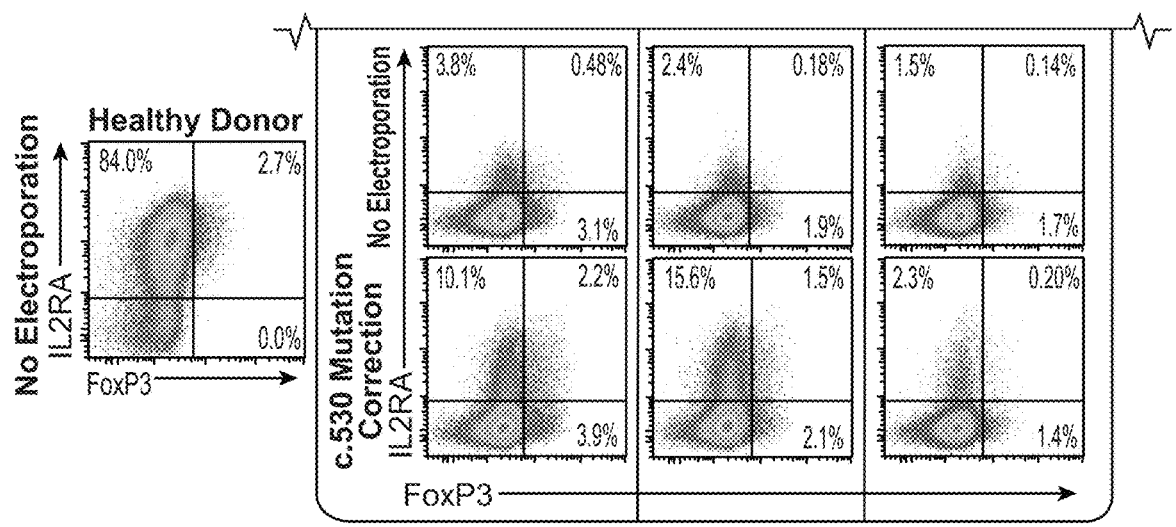
Figures 31A, 31B:
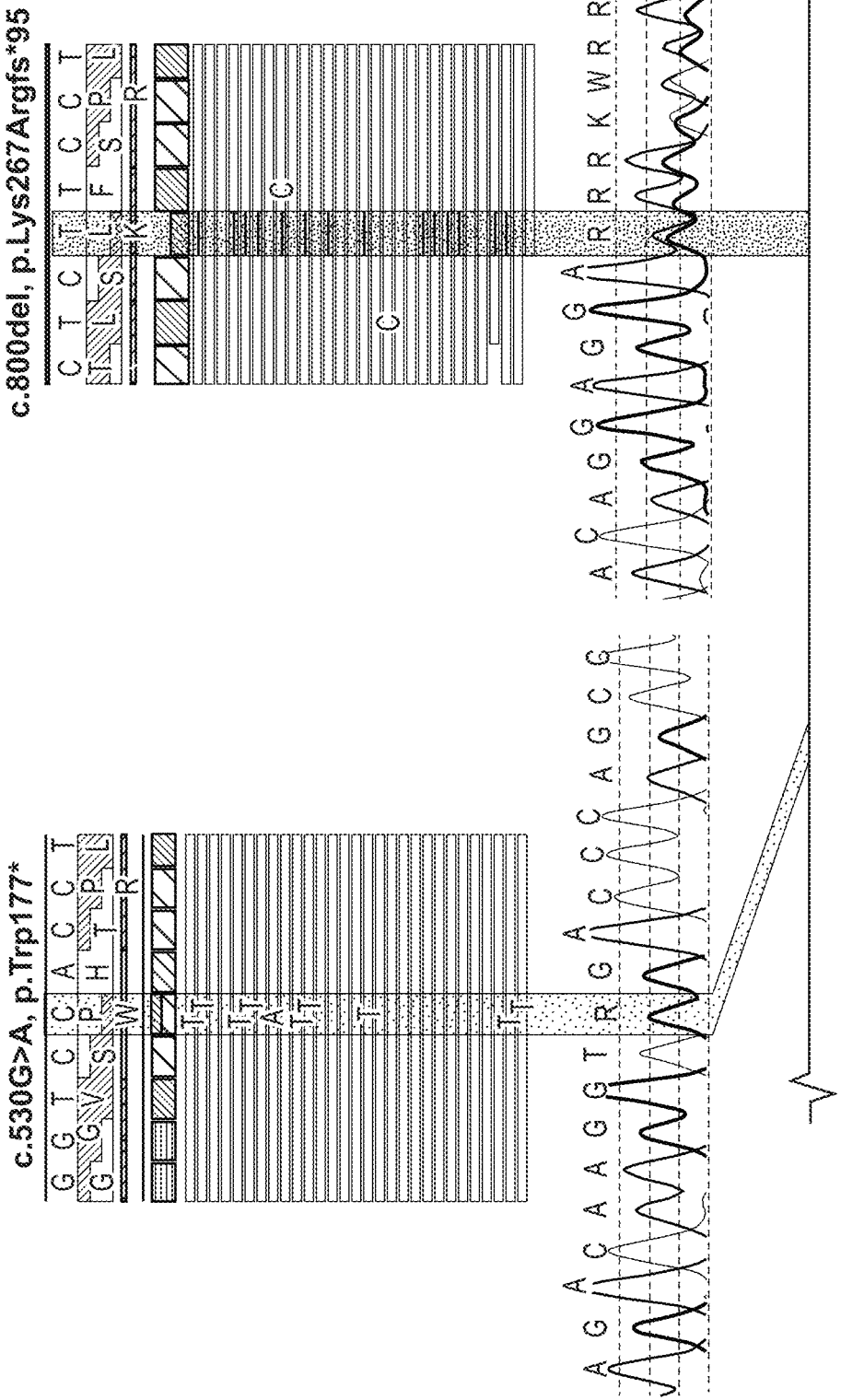
FIGS. 31A-D show identification of compound heterozygous mutations in IL2RA and design of corrective CRISPR-Cas9 genome targeting reagents. (A) Initial genetic testing of the proband using an in-house targeted next-generation sequencing multi-gene panel of over 40 genes known to be involved in monogenic forms of diabetes was negative. Subsequent exome sequencing in the trio of proband and parents revealed two causative mutations in the IL2RA gene. The mother possessed a single heterozygous mutation (c.530G>A) in exon 4 of IL2RA (SEQ ID NO: 1) (AGACAAGGTRGACCCAGCC), resulting in a premature stop codon. (B) The father possessed a single heterozygous mutation (c.800delA) in exon 8 of IL2RA (SEQ ID NO: 2 (ACAGGAGGARRRKWRRARAA), resulting in a frameshift mutation resulting in a 95 amino acid long run-on. Sanger sequencing confirmed that the proband was a compound heterozygote for both mutations. (C) A linear depiction of the IL2RA protein annotated with approximate locations of the two identified IL2RA mutations. SD1, sushi domain 1; SD2, sushi domain 2; TM, transmembrane; C, cytoplasmic. (D) The genomic sequences including the specified mutations ((SEQ ID NO: 3)(CAAAATGACC-CACGGGAAGACAAGGTAGACCC) for c.530G>A allele and SEQ ID NO: 4 (GACTTTGTTACACCACTACAG-GAGGAGAGTA) for c.800delA Allele)) were used to design CRISPR-Cas9 genome targeting reagents to correct the two IL2RA mutations. A gRNA was designed to cut adjacent to the site of each mutation, 8 bps away for c.530 mutation, and 7 bps away for c.800. For each mutation, an HDR template ((SEQ ID NO: 5) (ACAAGATGGACCC) for c.530 mutation and (SEQ ID NO: 6)(AGGAGAAAGAGTA for c.800)) was designed including the corrected sequence as well as a silent mutation in a degenerate base to disrupt the PAM sequence ("NGG") for each guide RNA. The corrected allele+silent PAM disruption sequence for c.530 (CAAAATGACCCACGGGAAGACAAGATGGACCC) (SEQ ID NO: 7) and c.800 (SEQ ID NO: 8) (GACTTTGT-TACACCACTACAGGAGAAAGAGTA) are shown. Displayed genomic regions (not to scale) for c.530 mutation site (hg38 ch10:6021526-6021557) and c800 mutation site (hg38 ch10:6012886-6012917). Both ssODN HDR Templates (ssDNA with 60 bp homology arms), and large dsDNA or ssDNA HDR Templates (as displayed, with ~300 bp homology arms) were used.
Figures 31C, 31D:
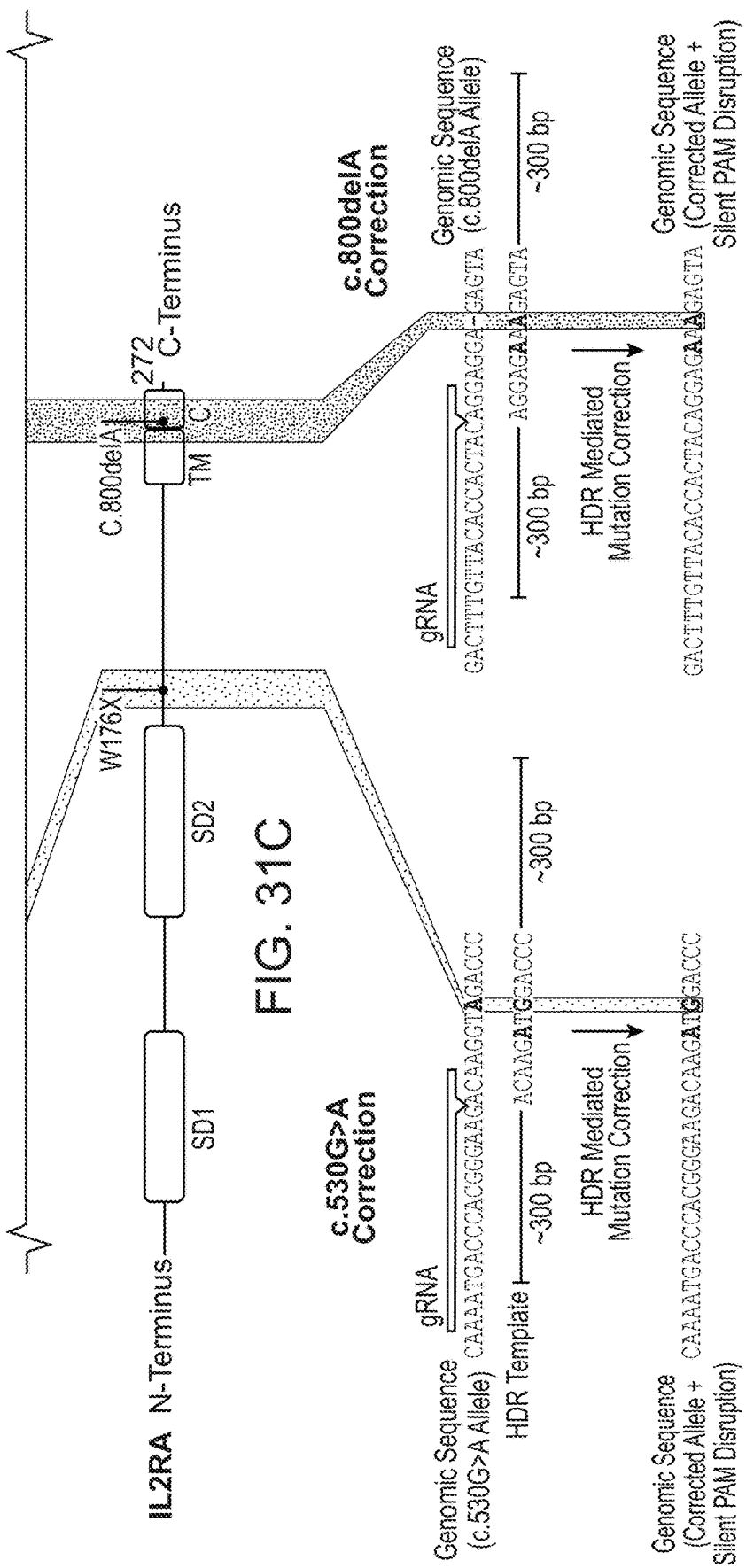
Figure 32A:
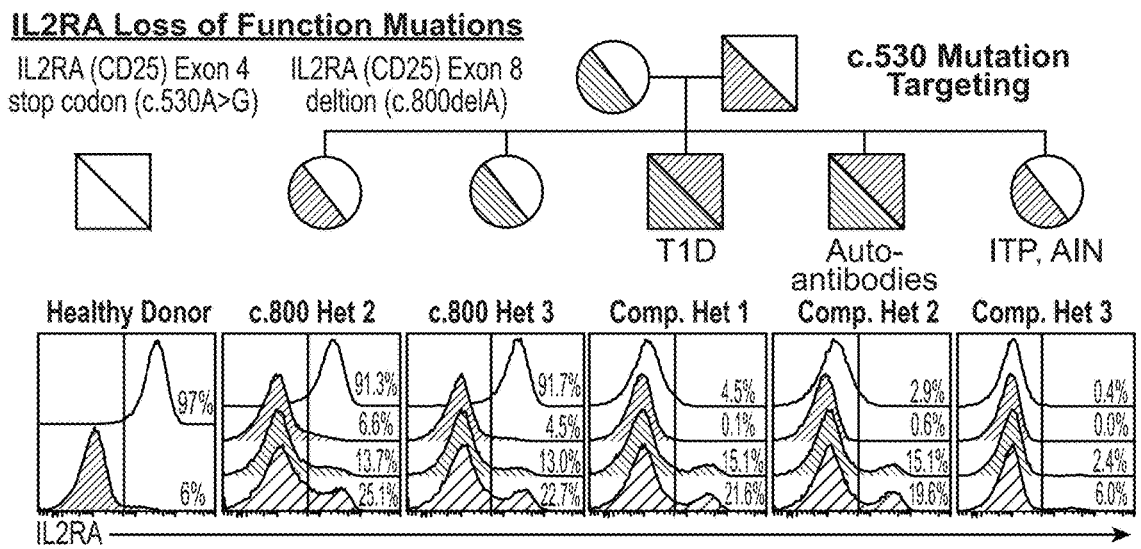
FIGS. 32A-C show HDR mediated correction of IL2RA c.530A>G loss of function mutation. (A) Unlike the gRNA targeting the c.800delA mutation at the C-terminus of IL2RA, the gRNA targeting the c.530A>G mutation (causing a stop codon in an interior exon) results in substantial (~90%) knockdown of IL2RA in a healthy donor and single heterozygotes (c.800 Het 2 and 3) 2 days following electroporation of the RNP alone (Blue) into CD3+ T cells. While starting from a very small IL2RA+ percentage, knockdown was also observed in all three compound heterozygotes, potentially as some small amount of protein can be surface expressed off of the c.800delA allele. This reduced CD25 expression can be partially rescued by inclusion of an ssODN HDR template and even more substantially rescued using a large dsDNA HDR template. Both template types contained the corrected sequence, a silent mutation to remove the gRNA's PAM sequence, and either 60 bp (ssODNs) or ~300 bp (large dsDNA) homology arms (FIG. 32). Unlike targeting of the c.800delA mutation for correction, CD25 surface expression in T cells from the compound heterozygotes is only seen when an HDR template is included. In all three compound heterozygotes, the dsDNA HDR template yielded greater percentages of CD25+ cells. (B) Increased pStat5 signaling in response to IL-2 stimulation (200 U/mL) 7 days following electroporation in CD3+ T cells from compound heterozygote patients undergoing HDR-mediated mutation correction compared to no electroporation or RNP only controls. (C) Similarly, increased proportions of CD25+ FoxP3+ cells are seen 9 days following electroporation in the HDR correction conditions in compound heterozygote patients. Lower percentages of correction were seen when targeting the c.530 mutation for HDR correction in compound heterozygote 3, potentially due altered cell-state associated with the patient's disease or the patient's immunosuppressive drug regimen. Electroporations were performed according to optimized non-viral genome targeting protocol set forth in the examples. For ssODN electroporations, 100 pmols in 1 uL $H_2O$ were electroporated.
Figure 32B:
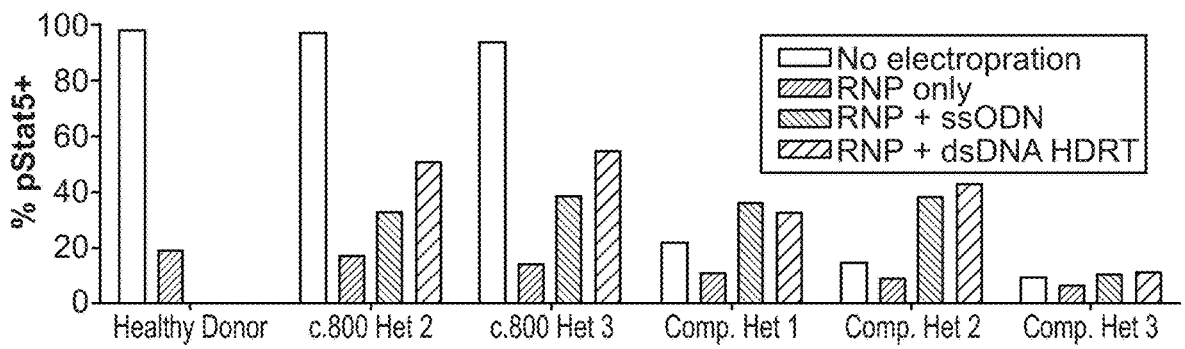
Figure 32C:
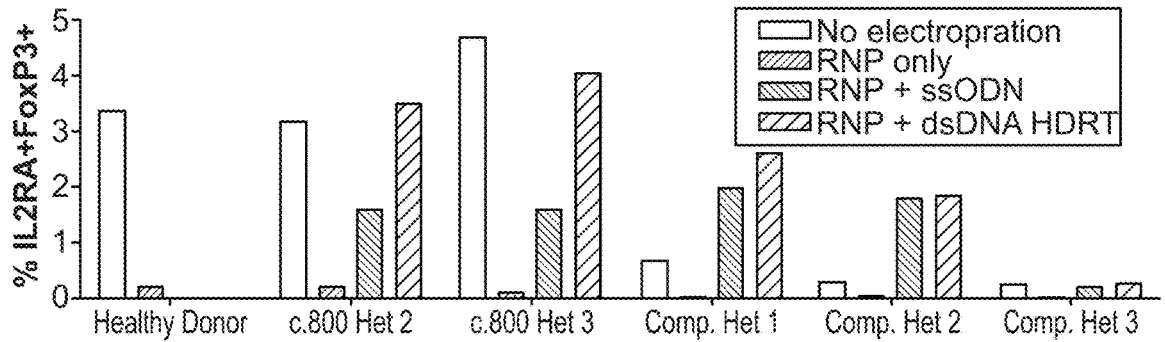
Figure 33A:
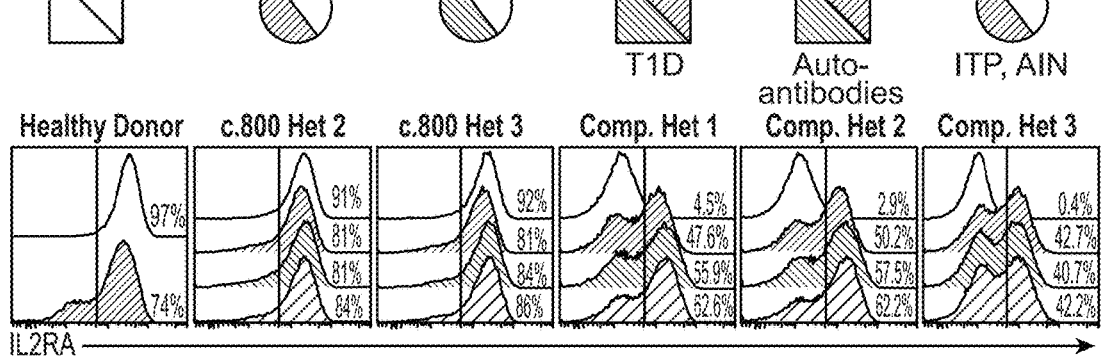
FIGS. 33A-C show non-HDR mediated correction of IL2RA c.800delA frameshift loss of function mutation. (A) Histograms of CD25 surface expression in CD3+ T cells in all children from a family carrying two loss-of-function IL2RA mutations, including three compound heterozygotes that express minimal amounts of IL2RA on their surface (No electroporation, Grey). Two days following electroporation of an RNP containing a gRNA against the site of one of the two mutations, a one base pair deletion in the final exon of IL2RA (c.800delA) causing a run-on past the normal stop codon, CD3+ T cells from a healthy donor and single hets (c.800 Het 2 and 3) show slight increase in CD25– cells (RNP only, Blue). Low knock-out is potentially due to the gRNA targeting the C-terminus of the protein where small indels may cause less pronounced loss of surface protein expression. Surprisingly, the RNP alone resulted in CD25 surface expression in almost 50% of edited T cells in all three compound heterozygotes. Increases in the percent of cells with CD25 correction compared to RNP only could be achieved by inclusion of an ssODN HDR template sequence with the mutation correction (RNP+ssODN, Purple), and further increased when using a longer dsDNA HDR template to correct the mutation (RNP+dsDNA HDRT, Green) (FIG. 32). (B) Phospho Stat5 signaling in response to high dose IL-2 stimulation (200 U/mL) in edited CD3+ T cells following 7 days of expansion post-electroporation. Increased numbers of pStat5+ cells correlated with increases in CD25 surface expression (A). (C) Following 9 days of expansion post-electroporation, intracellular FoxP3 staining reveals a dramatically increased proportion of CD25+ FoxP3+ cells in CD3+ T cells compared to no electroporation controls, approaching the proportion of CD25+ FoxP3+ cells seen in a healthy donor similarly cultured. Electroporations were performed according to optimized non-viral genome targeting protocol (Examples). For ssODN electroporations, 100 pmols in 1 uL H2O were electroporated.
Figure 33B:
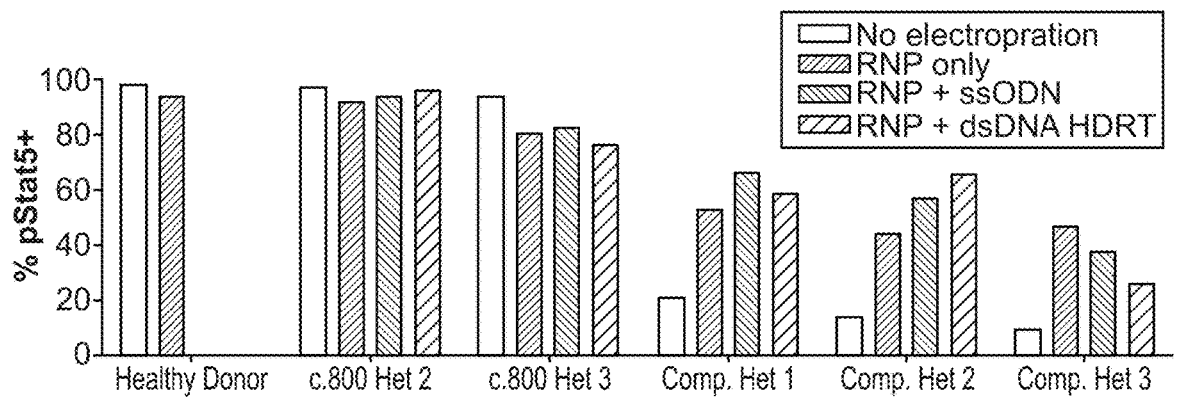
Figure 33C:
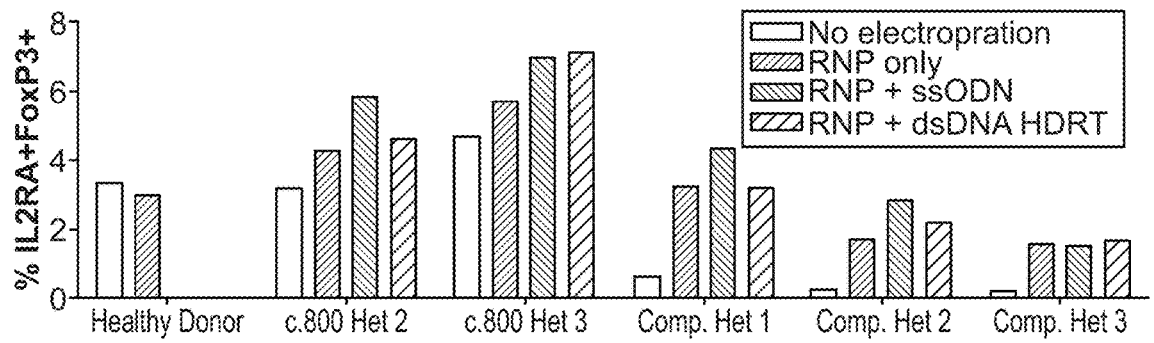
Figure 35A:
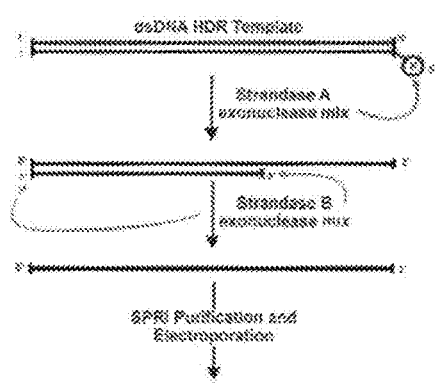
FIGS. 35A-D show multiple methods to produce long ssDNA HDR templates. (A) If a large enough amount of long single stranded DNA sequence could be produced for electroporation, off-target integrations could be reduced without overly compromising on-target efficiency. One method involves a two-step selective exonuclease digestion that specifically degrades one strand of a PCR product that has been labeled by 5' phosphorylation, easily added onto a PCR primer prior to amplification. (B) A second ssDNA production method based on sequential in-vitro transcription (IVT) and reverse transcription (RT) reaction was also applied. A PCR product with a short T7 promoter appended serves as an IVT template to produce a ssRNA product. Following annealing of an RT primer and reverse transcription, an RNA/DNA hybrid is formed which can be easily transformed into a long ssDNA template by incubation in sodium hydroxide (selectively degrades RNA strand). (C) At 2 days post-electroporation, viability in CD3+ T cells electroporated with only a ssDNA template was higher than those electroporated with only a dsDNA template (FIG. 11). (D) A ssDNA RAB11A-GFP HDR template showed high efficiency GFP integration similar to dsDNA templates, and maintained high efficiency integrations at higher molar amounts of template, potentially due to increased viability (C) as well as less mass per mole of DNA template. Individual points represent at least two healthy donors (C, D).
Figure 35B:
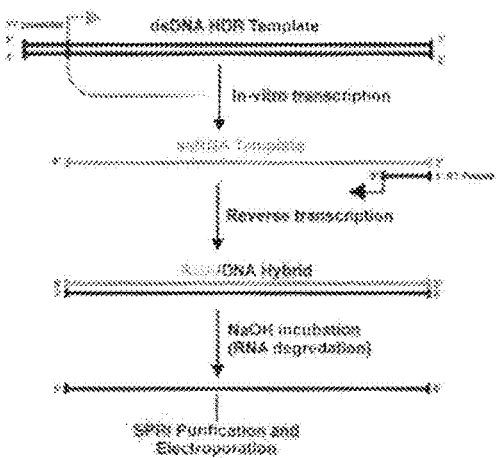
Figure 35C:
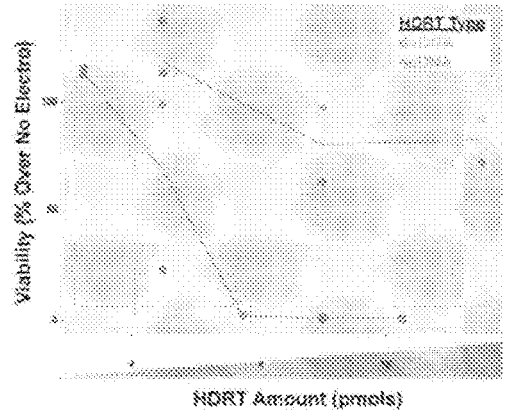
Figure 35D:
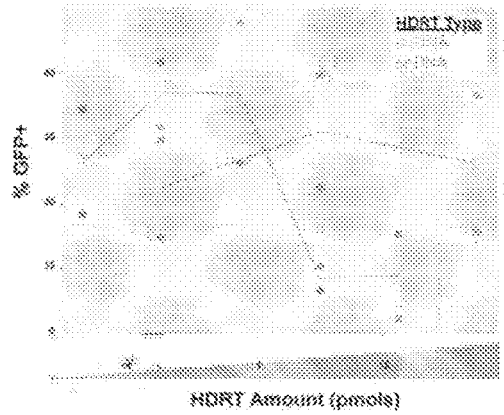

Whole exome sequencing revealed that the IL2RA deficient children harbored compound heterozygous mutations in IL2RA (FIG. 30A and FIG. 31). One mutation at c.530A>G creates a premature stop codon. Improvements in cell culture and electroporation methodologies made it possible to efficiently correct the mutation using ~120 bp chemically synthesized ssDNA HDR templates (FIG. 32). Rates were even higher using a longer dsDNA template (FIG. 30B and FIGS. 32 and 33). The corrected patient-derived T cells expressed IL2RA on their surface. Although correction was successful in all three siblings, lower rates of IL2RA expression were seen in compound het 3, which could be due to altered cell-state associated with the patient's disease or the fact she was on the only sibling treated with immunosuppression (Table 1 and FIG. 34). The second mutation, c.800delA, causes a frameshift in the reading frame of the final IL2RA exon resulting in misreading of the portion of the gene encoded in the final exon as well as run-on translation past the normal stop codon. This frameshift could be ameliorated even without an HDR template (FIG. 33). At this site, genomic cutting caused by a Cas9 RNP alone was sufficient to cause productive cell surface expression of IL2RA, likely by restoring the correct frame with insertion/deletion mutations (FIG. 33). Taken together, these data show how distinct mutations can be corrected in patient T cells with HDR template-dependent and non-HDR template-dependent repair mechanisms.

One potential therapeutic strategy for patients from this family with monogenic Treg defects would be ex vivo T cell gene correction followed by transfusion of autologous corrected Tregs. Treg cells produced by targeted correction could limit some of the potential risks of hematopoietic stem cell transplantation. Whether correcting one of the IL2RA mutations led to productive signaling and whether or not correction occurred in a meaningful fraction of FOXP3+ Tregs was tested. Following correction of the c.530A>G mutation, cells were able to functionally signal through IL2RA, the high-affinity IL-2 receptor. In response to IL-2 treatment, the modified cells demonstrated increased STAT5 phosphorylation, a hallmark of productive signaling (FIG. 31C and FIGS. 33 and 34). In addition, flow cytometry confirmed that a fraction of IL2RA corrected cells expressed FOXP3, a critical transcriptional factor in Tregs (FIG. 30D and FIGS. 32 and 33).

Figure 30E:
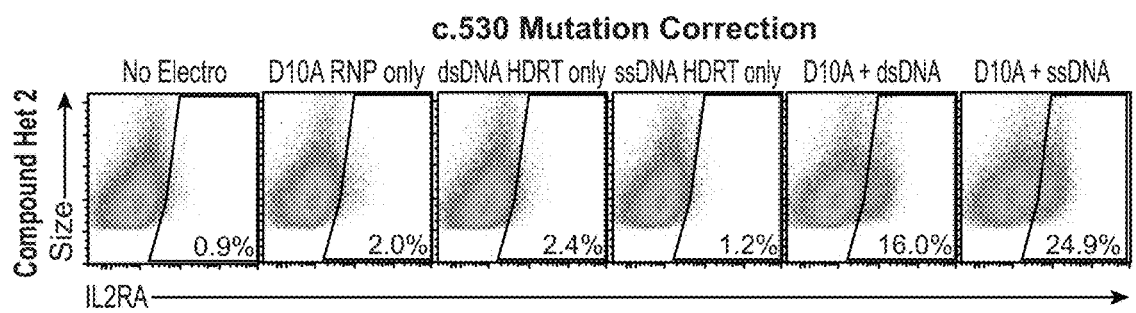

The endogenous gene encoding IL2RA is under tight control by multiple cis-regulatory elements that constitute a super-enhancer (Farh et al., "Genetic and epigenetic fine mapping of causal autoimmune disease variants," *Nature* 518, 337-343 (2015); and Simeonov et al. "Discovery of Stimulation-Responsive Immune Enhancers with Unbiased CRISPR Activation," *Nature* 549 (7670): 111-115 (2017). Therefore, therapeutic correction of IL2RA is likely to depend on specific repair of the gene in its endogenous genomic locus. Given that GFP insertions with Cas9 and dsDNA showed that there is a potential for non-specific integrations of dsDNA, we used D10A Cas9 nickase and a long ssDNA template to specifically repair the c.530A>G patient mutation. Using these reagents is was possible to specifically and selectively correct the mutant gene in ~20% of the T cells from the patient (FIG. 30E).

Non-viral gene targeting enables efficient insertion of defined sequences throughout the genome of primary human T cells. These insertions can range from the introduction or correction of single base pair mutations, to integration of large functional sequences and tags at endogenous loci, and multiplexed integrations throughout the genome are possible. For therapeutic applications of engineered T cells, off-target integrations can be significantly reduced by using D10A Cas9 nickase and a ssDNA HDR template. The methods and results provided herein will enable the accelerated development of engineered T cell therapies and the treatment of genetic disease.

What is claimed is:

1. An isolated viable, primary human immune cell comprising a complex comprising a ribonucleoprotein complex (RNP) and a DNA template, wherein the RNP comprises a nuclease domain and a guide RNA, wherein the size of the DNA template is greater than or equal to 300 base pairs (bp) in size, and wherein the 5' and 3' ends of the DNA template comprise nucleotide sequences that are homologous to genomic sequences flanking an insertion site in the genome of the primary cell, and wherein the primary cell does not comprise a viral vector for delivery of the DNA template.

2. The cell of claim 1, wherein the size of the DNA template is greater than or equal to 1 kilobase (kb).

3. The cell of claim 1, wherein the size of the DNA template is greater than or equal to 1.5 kb.

4. The cell of claim 1, wherein the size of the DNA template is 300 bp to 5 kb.

5. The cell of claim 1, wherein the DNA template is a double-stranded DNA template.

6. The cell of claim 1, wherein the DNA template is a linear DNA template.

7. The cell of claim 1, wherein the primary human immune cell is a primary human T cell.

8. The cell of claim 1, wherein the DNA template comprises a gene.

9. The cell of claim 1, wherein the DNA template encodes a chimeric antigen receptor (CAR).

10. An isolated population of cells, wherein at least 10% of the cells in the population are a cell of claim 1.

11. A method of editing a primary human immune cell, comprising:
    a. providing a complex comprising a ribonucleoprotein (RNP) and a DNA template, wherein the RNP comprises a nuclease domain and a guide RNA, wherein the size of the DNA template is greater than or equal to 300 bp in size and wherein the 5' and 3' ends of the DNA template comprise nucleotide sequences that are homologous to genomic sequences flanking an insertion site in the genome of the primary immune cell;
    b. non-virally introducing the complex into the primary immune cell, wherein the guide RNA specifically hybridizes to a target region of the genome of the primary immune cell, and wherein the nuclease domain cleaves the target region to create the insertion site in the genome of the primary immune cell; and
    c. editing the primary immune cell via insertion of the DNA template into the insertion site in the genome of the primary immune cell.

12. The method of claim 11, wherein non-virally introducing comprises electroporation.

13. The method of claim 11, wherein the size of the DNA template is greater than or equal to 1 kb.

14. The method of claim 11, wherein the size of the DNA template is greater than or equal to 1.5 kb.

15. The method of claim 11, wherein the size of the DNA template is 300 bp to 5 kb.

16. The method of claim 11, wherein the DNA template is a double-stranded DNA template.

17. The method of claim 11, wherein the DNA template is a linear DNA template.

18. The method of claim 11, wherein the primary human immune cell is a primary human T cell.

19. The method of claim 11, wherein the DNA template comprises a gene.

20. The method of claim 11, wherein the DNA template encodes a chimeric antigen receptor (CAR).

* * * * *